(12) United States Patent
Watanabe et al.

(10) Patent No.: US 7,985,885 B2
(45) Date of Patent: Jul. 26, 2011

(54) TERPHENYLENE DERIVATIVE, TETRAHALOTERPHENYL DERIVATIVE, AND PROCESSES FOR PRODUCING BOTH

(75) Inventors: Makoto Watanabe, Yokkaichi (JP); Tomokazu Ohashi, Yokkaichi (JP); Toshihide Yamamoto, Yokkaichi (JP)

(73) Assignee: Tosoh Corporation, Shunan-shi (JP)

( * ) Notice: Subject to any disclaimer, the term of this patent is extended or adjusted under 35 U.S.C. 154(b) by 649 days.

(21) Appl. No.: 11/910,759

(22) PCT Filed: Mar. 28, 2006

(86) PCT No.: PCT/JP2006/306352
§ 371 (c)(1),
(2), (4) Date: Oct. 5, 2007

(87) PCT Pub. No.: WO2006/109569
PCT Pub. Date: Oct. 19, 2006

(65) Prior Publication Data
US 2009/0023957 A1    Jan. 22, 2009

(30) Foreign Application Priority Data

Apr. 8, 2005 (JP) ............................... 2005-112774
Apr. 8, 2005 (JP) ............................... 2005-112775
Apr. 8, 2005 (JP) ............................... 2005-112776
Dec. 20, 2005 (JP) ............................... 2005-366667
Dec. 20, 2005 (JP) ............................... 2005-366668

(51) Int. Cl.
*C07C 13/465* (2006.01)
*C07C 22/00* (2006.01)

(52) U.S. Cl. .......................................... 585/27; 570/183
(58) Field of Classification Search .................. 585/27; 570/183
See application file for complete search history.

(56) References Cited

FOREIGN PATENT DOCUMENTS

| | | |
|---|---|---|
| JP | 2003-104916 A | 4/2003 |
| JP | 2004-256497 A | 9/2004 |
| JP | 2005-255531 A | 9/2005 |
| JP | 2006-111854 A | 4/2006 |
| WO | 03/016599 A1 | 2/2003 |

OTHER PUBLICATIONS

Bong et al., Synthesis of syn and anti doublebent phenylene, (Organic Letters (2004), 6 (13), 2249-2252).*
Hagen Klauk et al., "High-mobility polymer gate dielectric pentacene thin film transistors", Journal of Applied Physics, Nov. 1, 2002, pp. 5259-5263, vol. 92, No. 9, American Institute of Physics.
Henning Sirringhaus et al., "Integrated Optoelectronic Devices Based on Conjugated Polymers", Science, Jun. 12, 1998, pp. 1741-1744, vol. 280.
Youichi Sakamoto et al., "Perfluoropentacene: High-Performance p-n Junctions and Complementary Circuits with Pentacene", J. Am. Chem. Soc., 2004, pp. 8138-8140, vol. 126, American Chemical Society.
Bruce C. Berris et al., "A New Approach to the Construction of Biphenylenes by the Cobalt-Catalyzed Cocyclization of o-Diethynylbenzenes with Alkynes. Application to an Iterative Approach to [3]Phenylene, the First Member of a Novel Class of Benzocyclobutadienoid Hydrocarbons", J. Am. Chem. Soc., 1985, pp. 5670-5687, vol. 107, American Chemical Society.
M. Hirthammer et al., "Bis(trimethylsilyl)- and 8,9-Tetrakis(trimethylsilyl)[4]phenylene", J. Am. Chem. Soc., 1986, pp. 2481-2482, vol. 108, American Chemical Society.
Von Luis Blanco et al., "2,3,9,10-Tetrakis(trimethylsily)[5]phenylen durch regiospezifische cobaltkatalysierte Cocyclisierung von 1,6-Bis(triisopropylsily)-1,3,5-hexatriin", Angew. Chem., 1987, pp. 1276-1277, No. 12.
Edited by CSJ: The Chemical Society of Japan, "Jikken Kagaku Koza 13", Dai 5 Han, 2004, pp. 96-107, Maruzen Co., Ltd.

\* cited by examiner

*Primary Examiner* — Jafar Parsa
(74) *Attorney, Agent, or Firm* — Sughrue Mion, PLLC

(57) ABSTRACT

An object of the present invention relates to provision of a terphenylene derivative having excellent oxidation resistance and capable of forming a semiconductor active phase by a coating process and an oxidation-resistant organic semiconductor material using the same, as well as an organic thin film. The invention relates to production of a terphenylene derivative represented by the formula (1) by tetralithiating a tetrahaloterphenyl derivative with a lithiating agent and subsequently treating the resulting compound with a copper compound:

[ka 1]

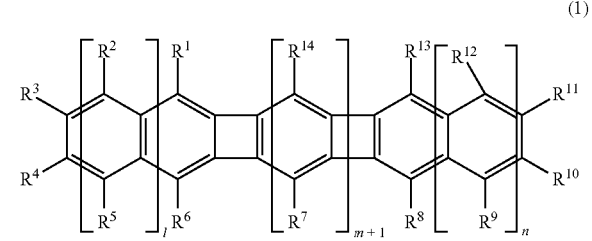

(1)

wherein $R^1$ to $R^{14}$ are the same or different and each represents a hydrogen atom, a fluorine atom, a chlorine atom, an aryl group having 4 to 30 carbon atoms, an alkynyl group having 3 to 20 carbon atoms, an alkenyl group having 2 to 30 carbon atoms, an alkyl group having 1 to 20 carbon atoms or a halogenated alkyl group having 1 to 20 carbon atoms, or a diarylamino group having 8 to carbon atoms; and l, m, and n each represents an integer of 0 or 1.

9 Claims, 1 Drawing Sheet

TERPHENYLENE DERIVATIVE, TETRAHALOTERPHENYL DERIVATIVE, AND PROCESSES FOR PRODUCING BOTH

TECHNICAL FIELD

The present invention relates to a terphenylene derivative capable of development to electronic materials such as an organic semiconductor, a use thereof, and a process for producing the same. Furthermore, the invention relates to a tetrahaloterphenyl derivative which is a precursor compound of the terphenylene derivative, and a process for producing the same.

BACKGROUND ART

Recently, organic semiconductor devices represented by an organic thin-film transistor have attracted attention owing to characteristics such as saving of energy, low costs, and flexibility which inorganic semiconductor devices lack. The organic thin-film transistor is composed of several kinds of materials such as an organic semiconductor active phase, a substrate, an insulating phase, and electrodes. Of these, an organic semiconductor active phase in charge of carrier movement of charges plays a primary role in the device. The performance of the semiconductor device is affected by the carrier mobility of an organic material constituting the organic semiconductor active phase.

As processes for preparing the organic semiconductor active phase, there are generally known a vacuum deposition process which is carried out by vaporizing an organic material at a high temperature under vacuum and a coating process wherein an organic material is dissolved in a suitable solvent and the solution is applied. The coating can be also carried out using a printing technology without using high-temperature and high-vacuum conditions. Since a significant reduction of production costs of the device preparation can be achieved by printing, the coating process is a preferable process from an economical viewpoint. However, hitherto, there is a problem that it is increasingly difficult to form the semiconductor active phase from a material by the coating process as the performance of the material increases as an organic semiconductor.

For example, it has been reported that a crystalline material such as pentacene has a high carrier mobility equal to amorphous silicon and exhibits excellent semiconductor device properties (see Non-Patent Document 1). Also, there has been reported an attempt to produce the device by the coating process through dissolution of a polyacene such as pentacene (see Patent Document 1). However, since pentacene has a low solubility owing to its strong cohesiveness, high-temperature heating or the like conditions are necessary for applying the coating process. Furthermore, since a solution of pentacene is extremely easily oxidized with oxygen, the application involves difficulty from processing and economical viewpoints. Moreover, a self-assembling material such as poly(3-hexylthiophene) is soluble in a solvent and device preparation by coating has been reported. However, since the carrier mobility is one figure lower than that of a crystalline compound (see Non-Patent Document 2), there is a problem that the resulting organic semiconductor device shows a low performance.

Moreover, these organic semiconductor materials are known to show p-type semiconductor properties. For constructing an energy-saving circuit, both of p-type and n-type conductors are necessary. It is known that replacement of hydrogen of a p-type organic semiconductor material with fluorine affords a material showing n-type semiconductor properties. For example, perfluoropentacene shows n-type semiconductor properties. (see Non-Patent Document 3). However, there is a problem that a special fluorinating agent is required and also the yield in fluorination is low.

Moreover, unsubstituted terphenylene is a rigid rod-like molecule and is known to have a structure resembling pentacene but is unstable. Furthermore, a synthetic process thereof has a large number of steps and involves a step including a photoreaction, so that it is industrially not a preferable process for production (see Non-Patent Document 4).

Non-Patent Document 1: "Journal of Applied Physics", (USA), 2002, vol. 92, pp. 5259-5263

Non-Patent Document 2: "Science", (USA), 1998, vol. 280, pp. 1741-1744

Non-Patent Document 3: "Journal of American Chemical Society", (USA), 2004, vol. 126, pp. 8138-8140

Non-Patent Document 4: "Journal of American Chemical Society", (USA), 1985, vol. 107, 5670-5687

Patent Document 1: WO2003/016599 pamphlet

DISCLOSURE OF THE INVENTION

Problems that the Invention is to Solve

Thus, in view of the problems of the above conventional technologies, an object of the invention is to provide a terphenylene derivative having excellent oxidation resistance and capable of forming a semiconductor active phase by a coating process and an oxidation-resistant organic semiconductor material using the same, as well as an organic thin film. Furthermore, another object of the invention is to provide a tetrahaloterphenyl derivative useful as a starting material for the terphenylene derivative and a process for producing the same.

Means for Solving the Problems

As a result of the extensive studies for solving the above problems, the present inventors have found a novel terphenylene derivative of the invention. In addition, since the terphenylene derivative is excellent in oxidation resistance and application of a coating process is possible, so that a crystalline thin film can be easily and steadily prepared. Thus, they have found an oxidation-resistant organic semiconductor material comprising the terphenylene derivative and a thin film thereof and hence they have accomplished the invention.

Furthermore, the inventors have found a novel precursor compound, i.e., a specific tetrahaloterphenyl derivative capable of effectively producing the terphenylene derivative and have found a process for efficiently producing such a tetrahaloterphenyl derivative and hence they have accomplished the invention.

ADVANTAGE OF THE INVENTION

There are provided a terphenylene derivative having an excellent oxidation resistance and capable of forming a semiconductor active phase by a coating process and a use thereof. Furthermore, according to the production process of the invention, a terphenylene derivative to which fluorine atom(s) are introduced can be produced and thus an organic semiconductor material can be provided.

BEST MODE FOR CARRYING OUT THE INVENTION

Figure 1:
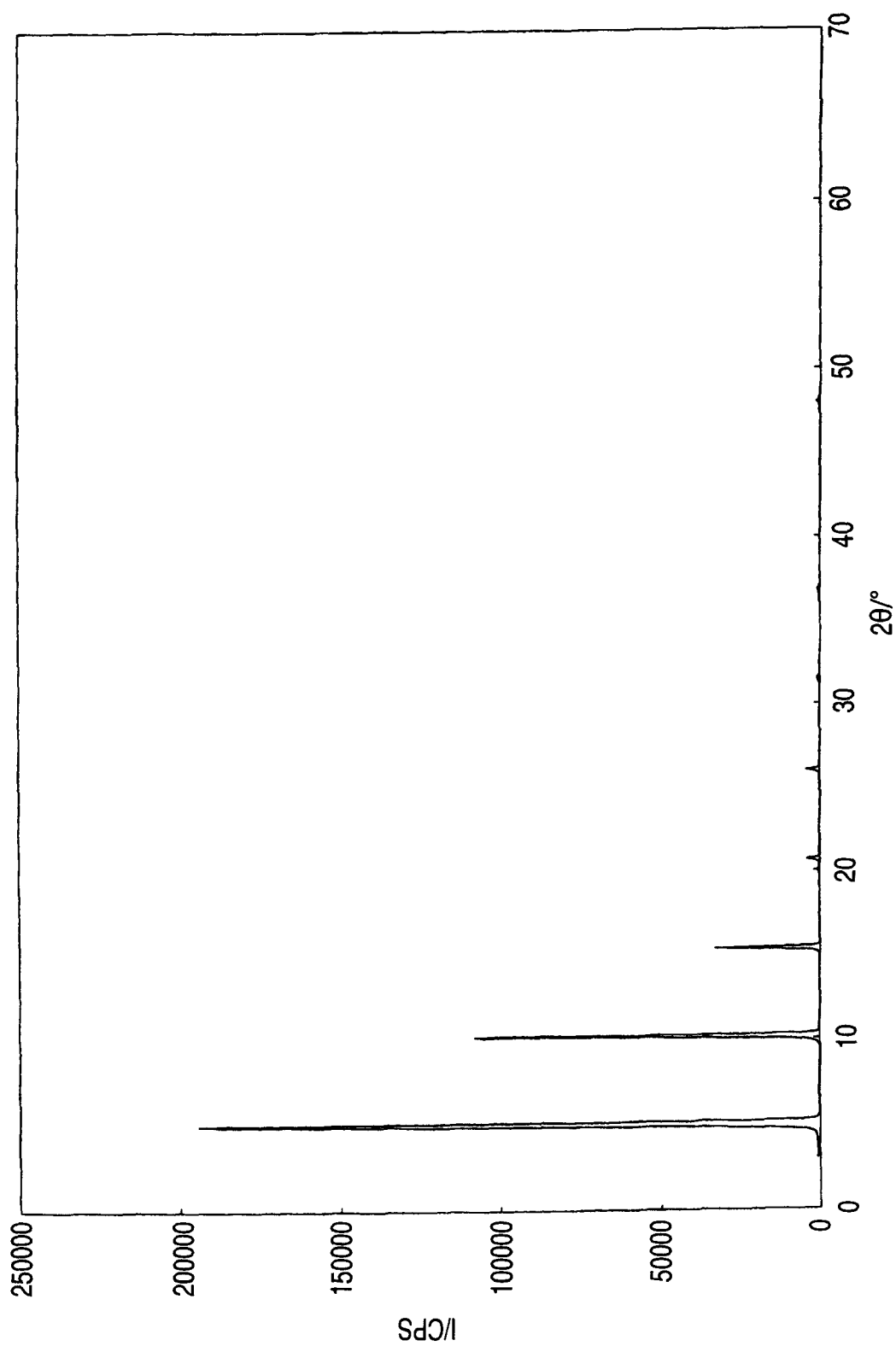
FIG. 1 is a graph showing a result of X-ray diffraction measurement of the thin film prepared in Example 7.

The following will explain the present invention in detail. The description will be performed on a terphenylene derivative and the process for producing the same, a tetrahaloterphenyl derivative and a process for producing the same, and an oxidation-resistant organic semiconductor material comprising the terphenylene derivative and a thin film thereof, in this order.

(Terphenylene Derivative)

The terphenylene derivative is represented by the following formula (1).

[ka 1]

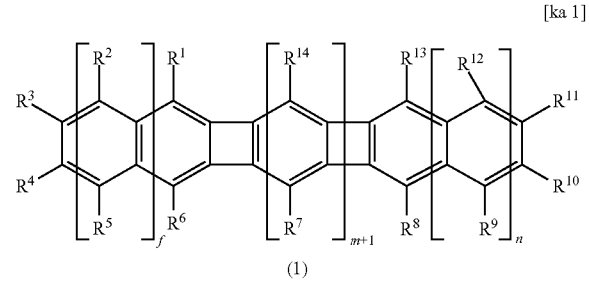

(1)

wherein $R^1$ to $R^{14}$ are the same or different and each represents a hydrogen atom, a fluorine atom, a chlorine atom, an aryl group having 4 to 30 carbon atoms, an alkynyl group having 3 to 20 carbon atoms, an alkenyl group having 2 to 30 carbon atoms, an alkyl group having 1 to 20 carbon atoms or a halogenated alkyl group having 1 to 20 carbon atoms, or a diarylamino group having 8 to 30 carbon atoms; any two or more of $R^1$ to $R^6$ may be combined with each other and any two or more of $R^8$ to $R^{13}$ may be combined with each other; and l, m, and n each represents an integer of 0 or 1; when l=0, m=0, and n=0, when l=1, m=0, and n=0, or when l=0, m=1, and n=0, at least one of the substituents $R^1$ to $R^{14}$ is not a hydrogen atom.

In the formula (1) of the invention, in the case where any two or more of $R^1$ to $R^6$ are combined with each other, the combination of the substituents $R^3$ and $R^4$ may be mentioned as a preferable combination. Also, an unsaturated ring formation may be mentioned as a preferable combination form in the case where any two or more thereof may be combined with each other. In the case where any two or more of $R^8$ to $R^{13}$ are combined with each other, the combination of the substituents $R^{10}$ and $R^{11}$ may be mentioned as a preferable combination. Also, an unsaturated ring formation may be mentioned as a preferable combination form in the case where any two or more thereof may be combined with each other. Furthermore, in the case where any two or more of $R^1$ to $R^6$ may be combined with each other and any two or more of $R^8$ to $R^{13}$ may be combined with each other, these combinations may be formed either in both cases at the same time or in only any one case thereof.

In the values of l, m, and n of the formula (1) of the invention, as preferable combinations, there may be mentioned a case where m is 0, a case where m and l are both 0, a case wherein m, l, and n are all 0, a case where l and n are both 1, and a case where l is 1 and m is 0.

The ring structure of the terphenylene derivative represented by the formula (1) of the invention is not particularly limited and may be any structure wherein both ends of the ring structure are symmetrical or asymmetrical. The structure where both ends of the ring structure are symmetrical means a case where l and n are the same values and the substituents disposed at the corresponding positions of the left and right ring structures are coincident, that is, a case where $R^1$=$R^{13}$, $R^2$=$R^{12}$, $R^3$=$R^{11}$, $R^4$=$R^{10}$, $R^5$=$R^9$, and $R^6$=$R^8$. On the other hand, the structure wherein both ends of the ring structure are asymmetrical includes, for example, a case where l is different from n, a case where l and n are the same but the substituents disposed at the corresponding positions of the left and right ring structures are not coincident, and the like cases.

The following will further describe the substituents of the formula (1) of the invention.

In the substituents $R^1$ to $R^{14}$, the aryl group having 4 to 30 carbon atoms is not particularly limited and examples thereof may include a phenyl group, a p-tolyl group, a p-(n-octyl)phenyl group, a m-(n-octyl)phenyl group, a p-fluorophenyl group, a pentafluorophenyl group, a p-(trifluoromethyl)phenyl group, a p-(n-perfluorooctyl)phenyl group, a 2-thienyl group, a 5-(n-hexyl)-2-thienyl group, a 2,2'-bithienyl-5-group, a biphenyl group, a perfluorobiphenyl group, a 1-naphthyl group, a 2-naphthyl group, a 1-perfluoronaphthyl group, an anthracenyl group, a 2-fluorenyl group, a 9,9-dimethyl-2-fluorenyl group, a 1-biphenyleno group, a 2-biphenyleno group, a terphenyl group, a 2-pyridyl group, a tetrafluoropyridyl group, a bipyridyl group, a (diphenylamino)phenyl group, a (diphenylamino)biphenyl group, and the like.

In the substituents $R^1$ to $R^{14}$, the alkynyl group having 3 to 20 carbon atoms is an alkynyl group containing no silyl group and examples thereof may include a methylethynyl group, an isopropylethynyl group, a tert-butylethynyl group, an (n-octyl)ethynyl group, a trifluoromethylethynyl group, a phenylethynyl group, a {4-(n-octyl)phenyl}ethynyl group, a naphthylethynyl group, an anthracenylethynyl group, a biphenylethynyl group, a terphenylethynyl group, a benzylethynyl group, a biphenylenoethynyl group, a perfluorophenylethynyl group, a {p-(trifluoromethyl)phenyl}ethynyl group, an (n-perfluorooctyl)ethynyl group, a {4-(n-perfluorooctyl)phenyl}ethynyl group, and the like.

In the substituents $R^1$ to $R^{14}$, alkenyl group having 2 to 30 carbon atoms is not particularly limited and examples thereof may include an ethenyl group, a methylethenyl group, an isopropylethenyl group, a tert-butylethenyl group, an (n-octyl)ethenyl group, a (trifluoromethyl)ethenyl group, a phenylethenyl group, a {4-(n-octyl)phenyl}ethenyl group, a naphthylethenyl group, an anthracenylethenyl group, a perfluorophenylethenyl group, a {p-(trifluoromethyl)phenyl}ethenyl group, an (n-perfluorooctyl)ethenyl group, a biphenylethenyl group, a terphenylethenyl group, a benzylethenyl group, a biphenylenoethenyl group, a phenyl(methyl)ethenyl group, a (trimethylsilyl)ethenyl group, a (triethylsilyl)ethenyl group, a (triisopropylsilyl)ethenyl group, and the like. In this connection, in the case where a trans-form and a cis-form are present in the alkenyl group having 2 to 30 carbon atoms, it may be either the trans-form or the cis-form and may be a mixture thereof in any ratio.

In the substituents $R^1$ to $R^{14}$, the alkyl group having 1 to 20 carbon atoms is not particularly limited and examples thereof may include a methyl group, an ethyl group, a propyl group, an n-butyl group, an isobutyl group, a t-butyl group, a neopentyl group, an octyl group, a dodecyl group, and the like; the halogenated alkyl group having 1 to 20 carbon atoms is not particularly limited and examples thereof may include a trifluoromethyl group, a trifluoroethyl group, a perfluorooctyl group, and the like.

In the substituents $R^1$ to $R^{14}$, the diarylamino group having 8 to 30 carbon atoms is not particularly limited and examples thereof may include a diphenylamino group, a phenyl(3-methylphenyl)amino group, a di(3-methylphenyl)amino group, a di{4-(n-octyl)phenyl}amino group, a di(3-trifluoromethylphenyl)amino group, a (1-naphthyl)phenylamino group, a (2-naphthyl)phenylamino group, a di(1-naphthyl)amino group, a phenyl(2-fluorenyl)amino group, a phenyl (9,9-dimethyl-2-fluorenyl)amino group, a bis(2-fluorenyl)amino group, a di(2-thienyl)amino group, a phenyl (2-thienyl)amino groups a bis{2-(1-phenyl)pyrrolyl}amino group, a {2-(1-phenyl)pyrrolyl}phenylamino group, a 9-carbazolyl group, and the like.

Among the combined substituents formed in the cases where any two or more of $R^1$ to $R^6$ may be combined with each other and in the case where any two or more of $R^8$ to $R^{13}$ may be combined with each other, the following are mentioned as the unsaturated ring groups which are examples of preferable substituents.

Examples of the unsaturated rings may include benzene rings which may have substituent(s), tetraphenylene rings which may have substituent(s), cyclohexene rings which may have substituent(s), thiophene rings which may have substituent(s), and pyrrole rings which may have substituent(s), and the like. Examples of the benzene rings which may have substituent(s) may include a benzene ring, a dimethylbenzene ring, a diphenylbenzene ring, a naphthalene ring, a methylnaphthalene ring, a phenylnaphthalene ring, a triphenylene ring, and the like. Examples of the tetraphenylene rings which may have substituent(s) may be include a tetraphenylene ring, a phenyltetraphenylene ring, and the like. Examples of the cyclohexene rings which may have substituent(s) may include a cyclohexene ring, a phenylcyclohexene ring, and the like. Examples of the thiophene rings which may have substituent(s) may include a thiophene ring, a methylthiophene ring, an (n-octyl)thiophene ring, a phenylthiophene ring, and the like. Examples of the pyrrole rings which may have substituent(s) may include a pyrrole ring, a methylpyrrole ring, a phenylpyrrole ring, an indole ring, and the like.

The unsaturated ring is preferably a benzene ring which may have substituent(s) or a thiophene ring which may have substituent(s), and is particularly preferably a benzene ring or a thiophene ring.

With regard to the terphenylene derivative represented by the formula (1) of the invention, from the viewpoint that the terphenylene derivative and an oxidation-resistant organic semiconductor material comprising the terphenylene derivative and a thin film thereof exhibit high oxidation-resistance and carrier mobility, the following may be mentioned as examples of combinations of preferable substituents:

(1) an example wherein the substituents $R^1$ to $R^{14}$ are the same or different and each represents at least one substituent selected from the group consisting of a hydrogen atom, a fluorine atom, an aryl group having 4 to 30 carbon atoms, an alkynyl group having 3 to 20 carbon atoms, and an alkyl group having 1 to 20 carbon atoms and at least one of the substituents $R^1$ to $R^{14}$ is not a hydrogen atom;

(2) an example wherein the substituents $R^3$, $R^4$, $R^{10}$, and $R^{11}$ are the same or different and each represents at least one substituent selected from the group consisting of an aryl group having 4 to 30 carbon atoms, an alkynyl group having 3 to 20 carbon atoms, an alkenyl group having 2 to 30 carbon atoms, an alkyl group having 1 to 20 carbon atoms or a halogenated alkyl group having 1 to 20 carbon atoms, and a diarylamino group having 8 to 30 carbon atoms and the substituents $R^1$, $R^2$, $R^5$ to $R^9$, and $R^{12}$ to $R^{14}$ are the same or different and each represents at least one substituent selected from the group consisting of a hydrogen atom, a fluorine atom, and a chlorine atom;

(3) an example wherein the substituents $R^3$, $R^4$, $R^{10}$, and $R^{11}$ are the same or different and each represents at least one substituent selected from the group consisting of an aryl group having 4 to 30 carbon atoms, an alkynyl group having 3 to 20 carbon atoms, an alkyl group having 1 to 20 carbon atoms or a halogenated alkyl group having 1 to 20 carbon atoms and the substituents $R^1$, $R^2$, $R^5$ to $R^9$, and $R^{12}$ to $R^{14}$ are the same or different and each represents at least one substituent selected from the group consisting of a hydrogen atom and a fluorine atom;

(4) any of an example wherein m is C, an example wherein m and l are both 0, and an example wherein m, l, and n are all 0 in the formula (1);

(5) an example wherein any two or more of the substituents $R^1$ to $R^6$ may be combined with each other and any two or more of the substituents $R^8$ to $R^{13}$ may be combined with each other, or an example wherein any two or more are combined with each other in only any one of the substituent combinations of the substituents $R^1$ to $R^6$ and the substituents $R^8$ to $R^{13}$.

(6) an example wherein the combination of any two or more of the substituents $R^1$ to $R^6$ is a combination of the substituents $R^3$ and $R^4$ and the combination of any two or more of the substituents $R^8$ to $R^{13}$ is a combination of the substituents $R^{10}$ and $R^{11}$ in the above (5).

(7) an example wherein the combined substituent is an unsaturated ring in the above example (5) or (6); and (8) an example which satisfies any of the above (5) to (7) in any example of the above (1) to (4).

The terphenylene derivative represented by the formula (1) of the invention is not particularly limited so far as the terphenylene derivative and an oxidation-resistant organic semiconductor comprising the terphenylene derivative and a thin film thereof exhibit high oxidation-resistance and carrier mobility and the following compounds may be mentioned, for example.

[ka 2]

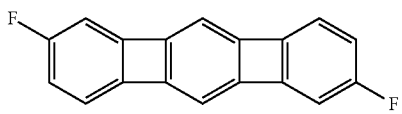 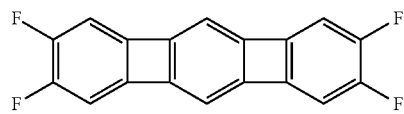

-continued
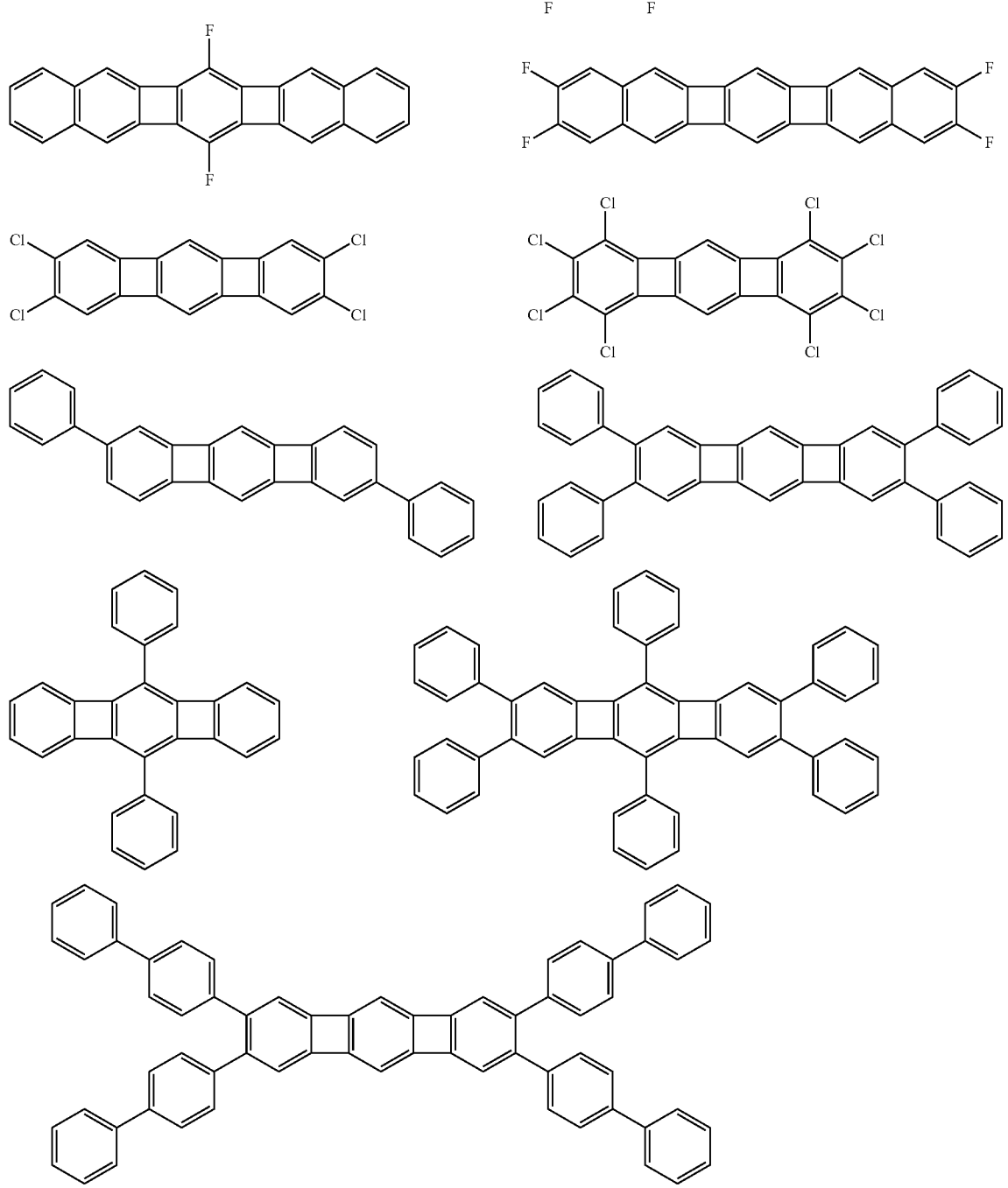

-continued
[ka 3]
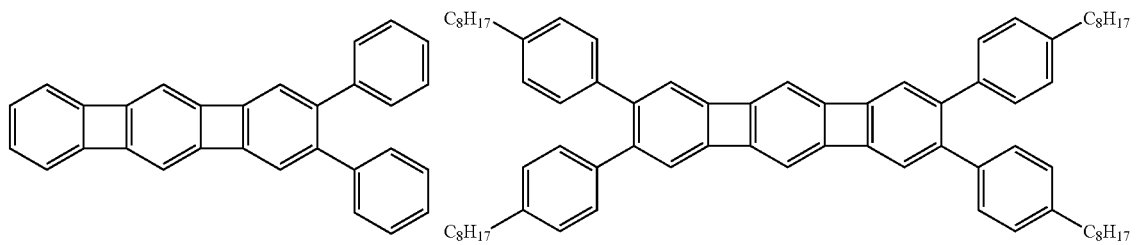
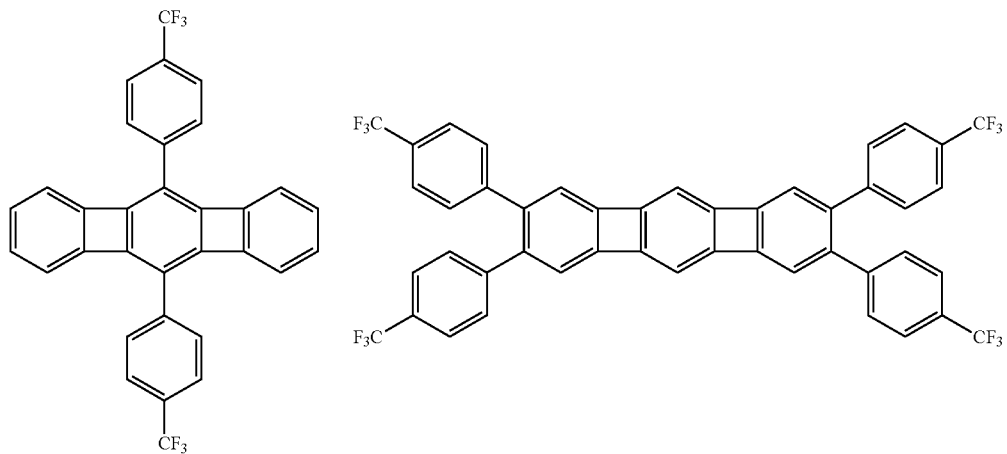
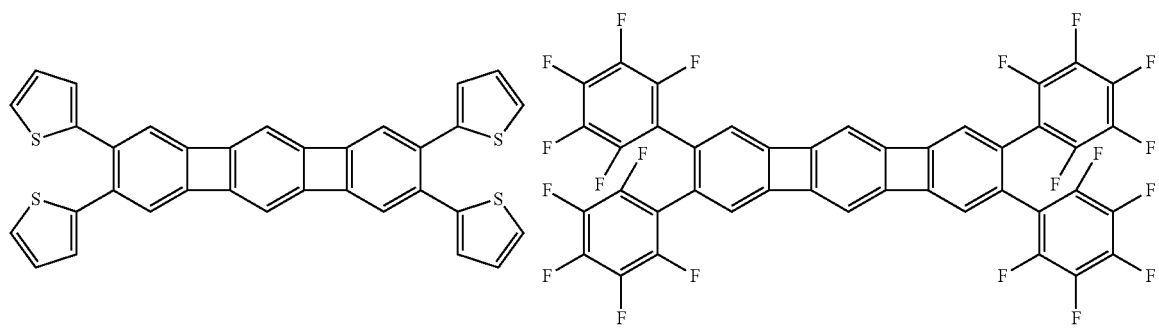
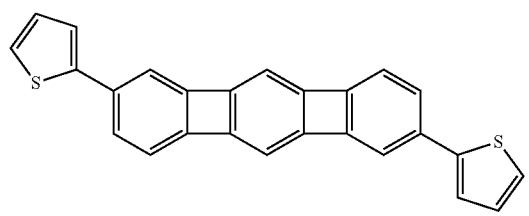
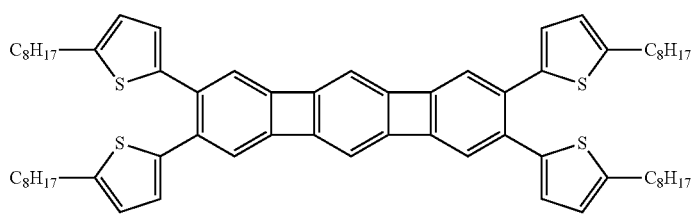
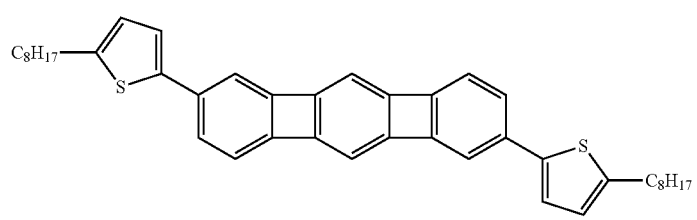

-continued
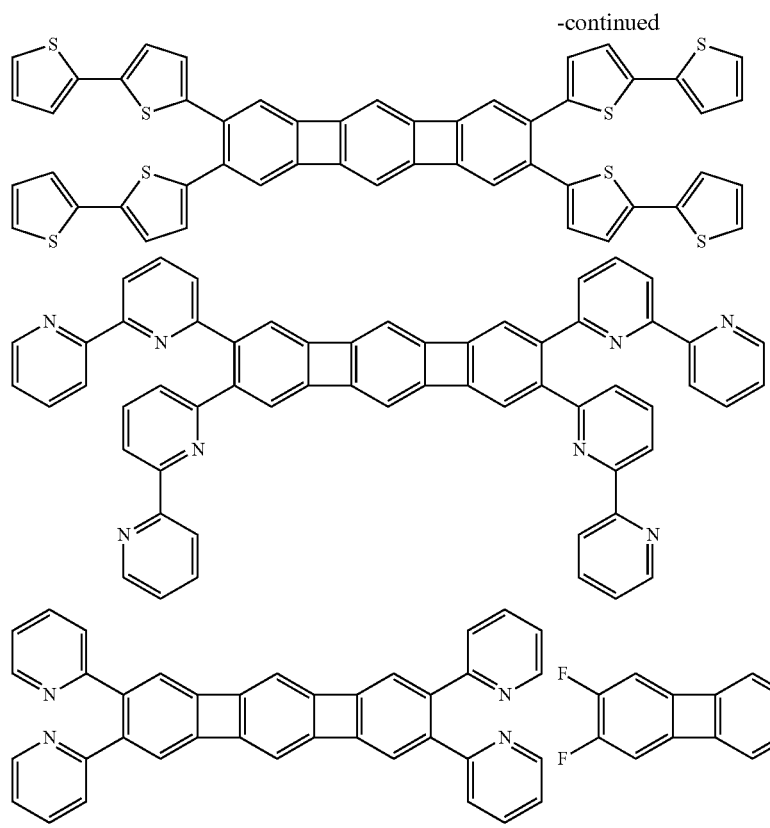
[ka 4]
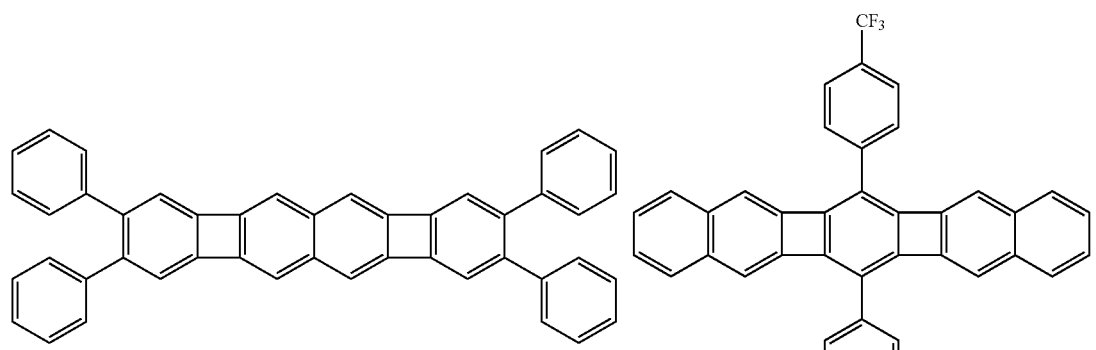
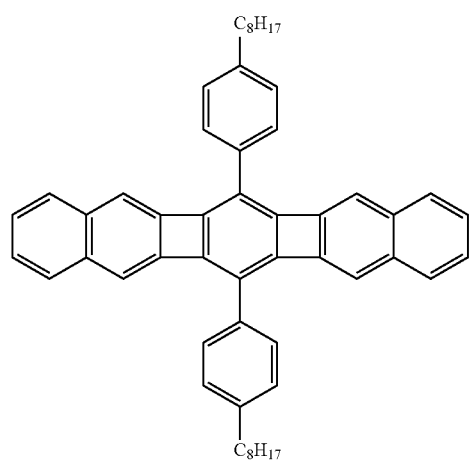

-continued
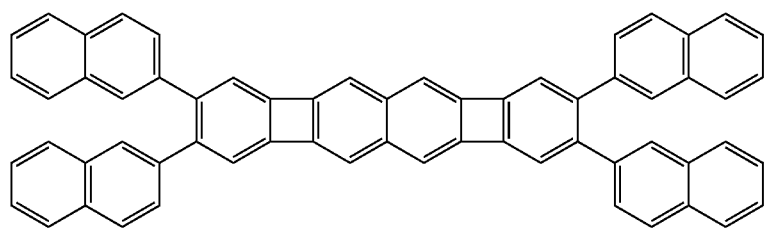
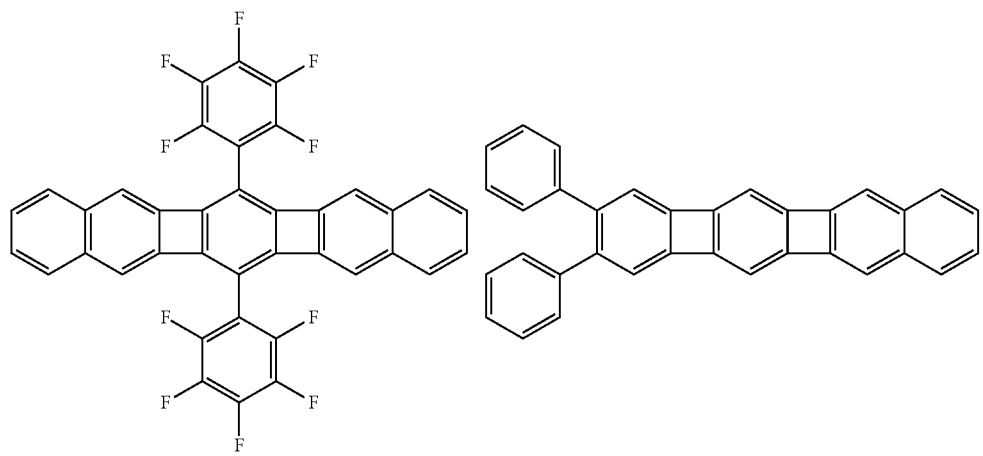
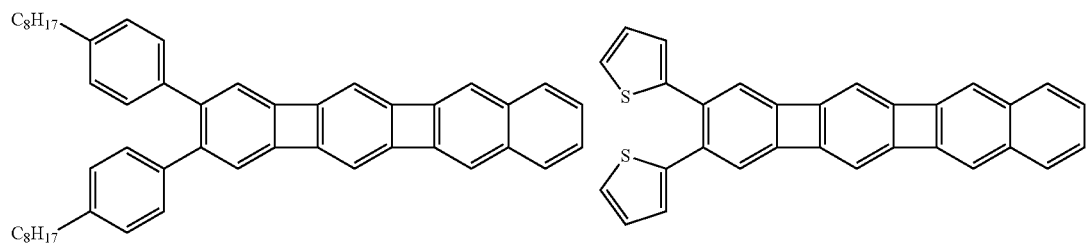
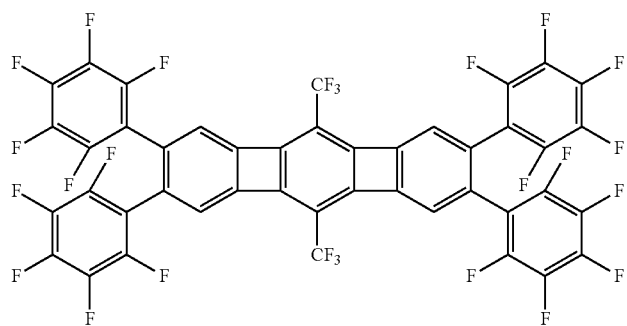
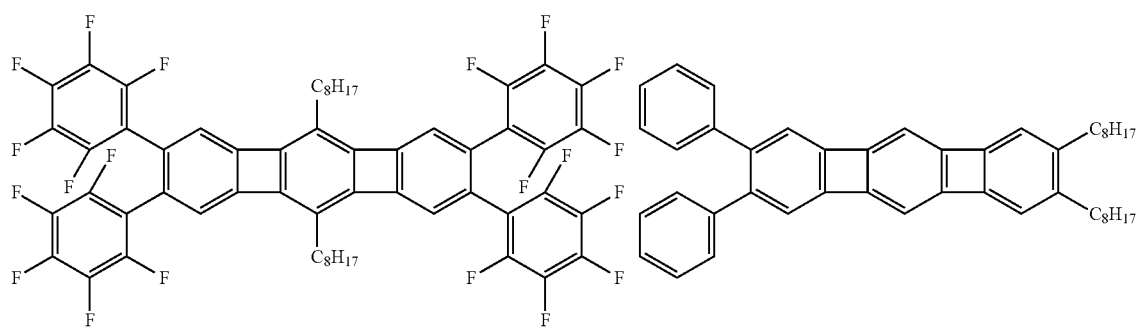

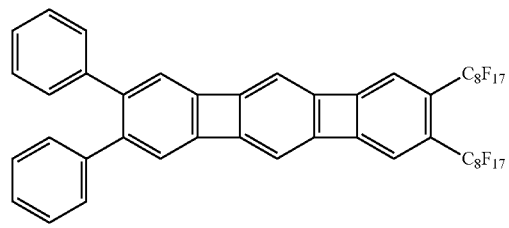
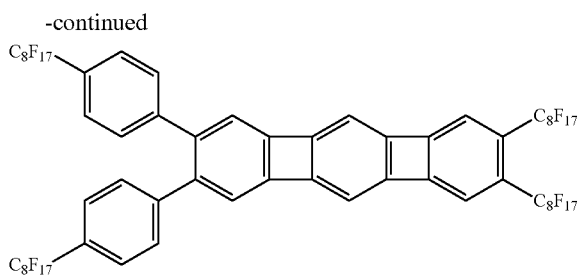
-continued
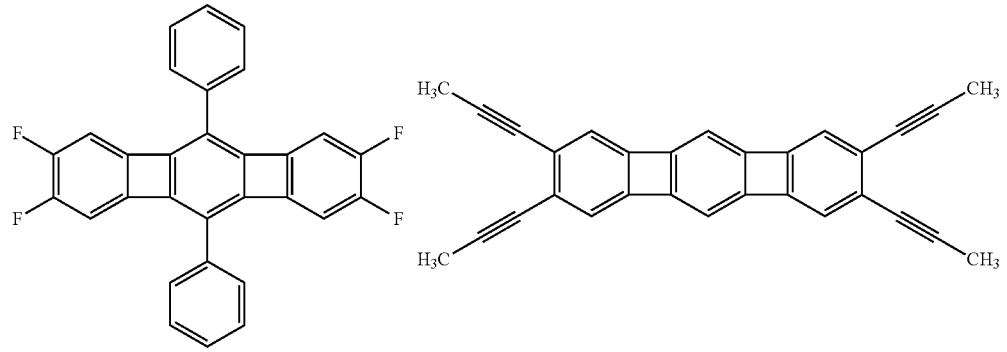
[ka 5]
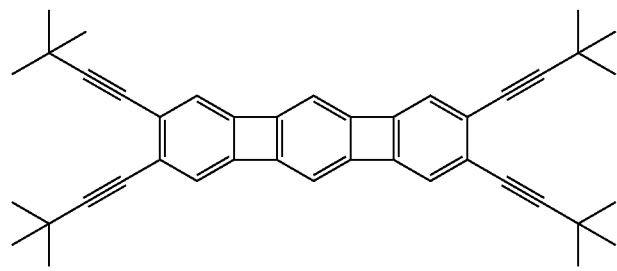
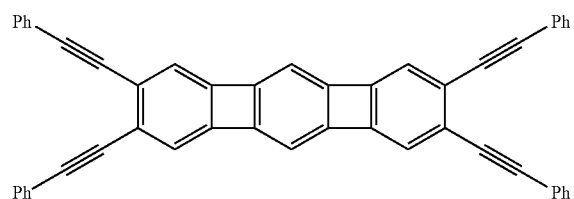
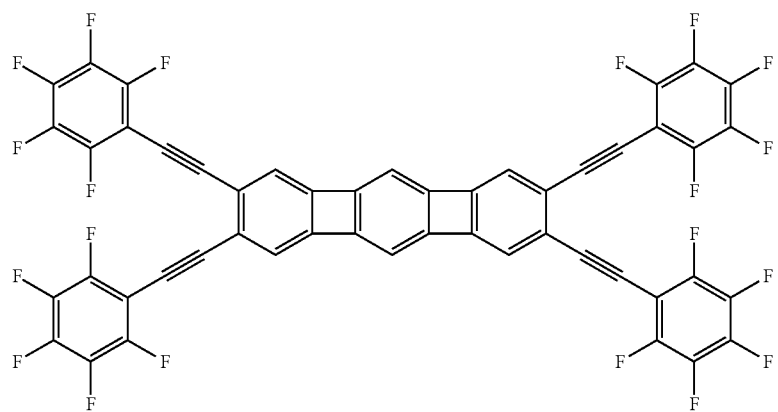

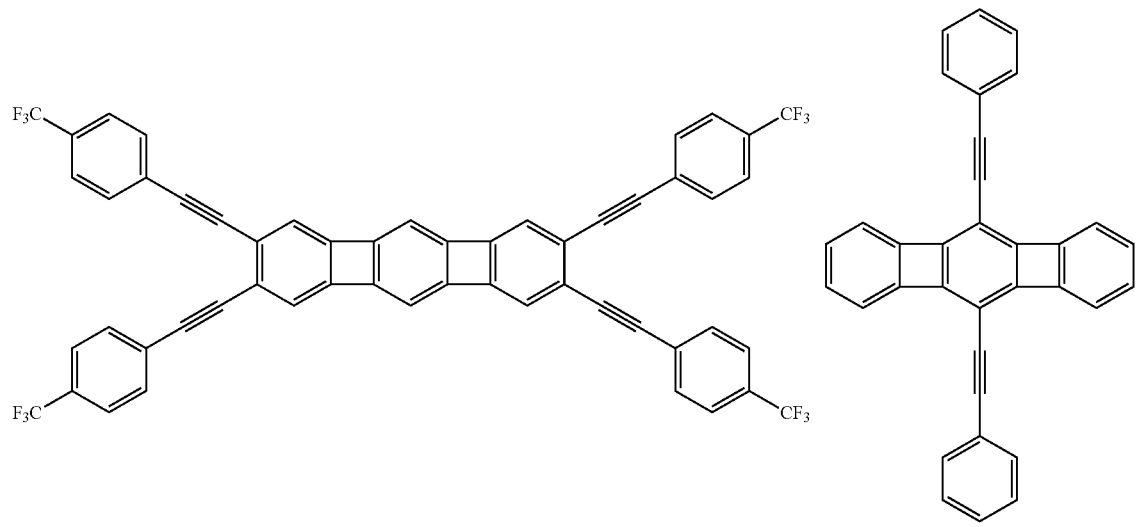
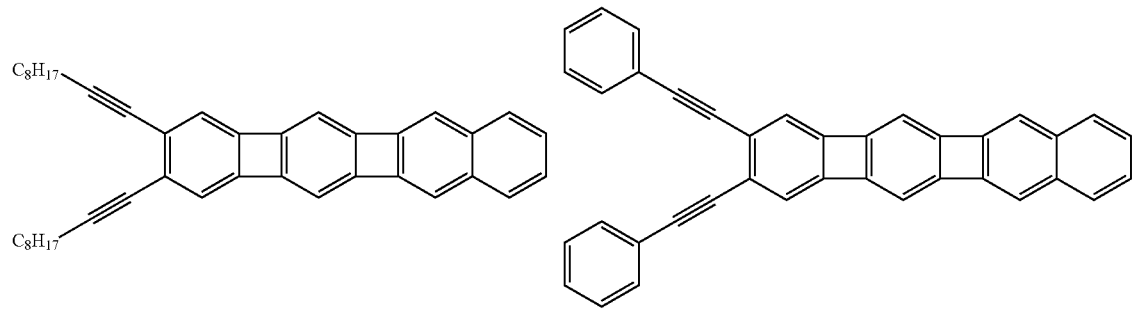
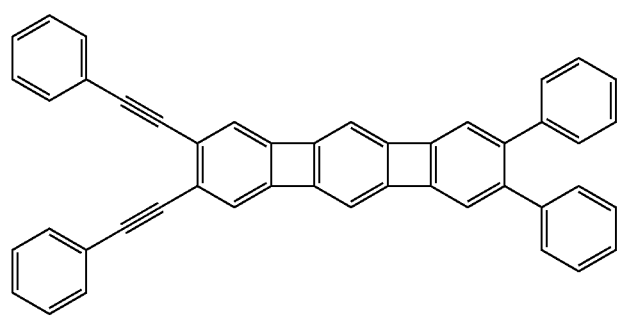
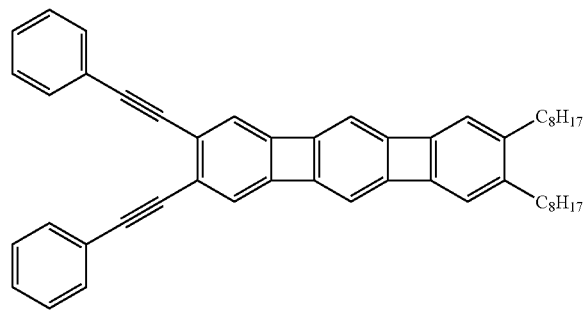

-continued
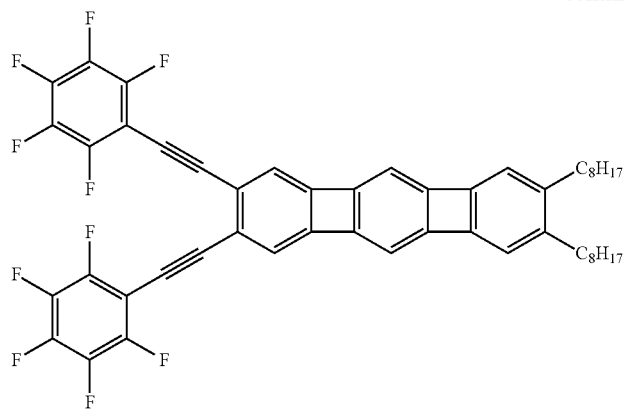
[ka 6]
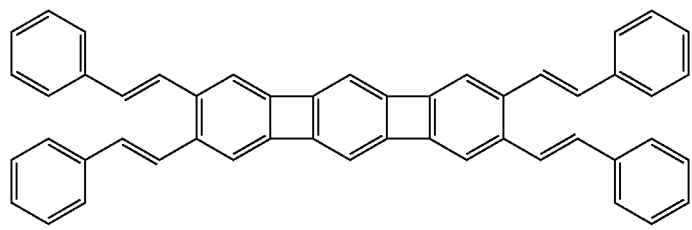
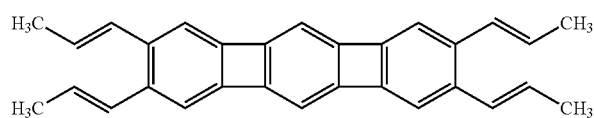
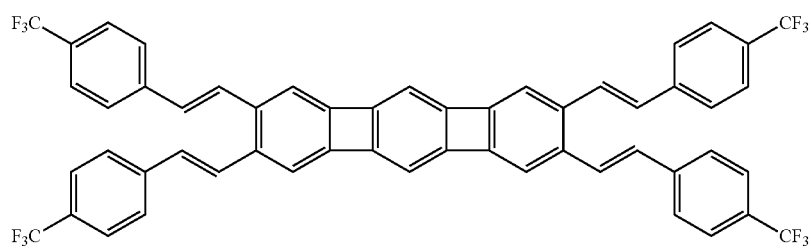
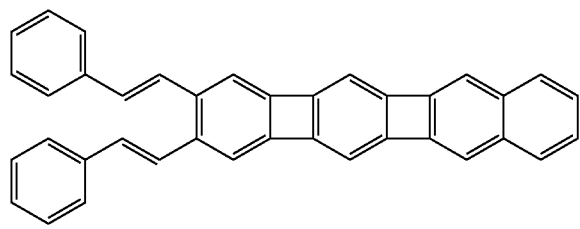
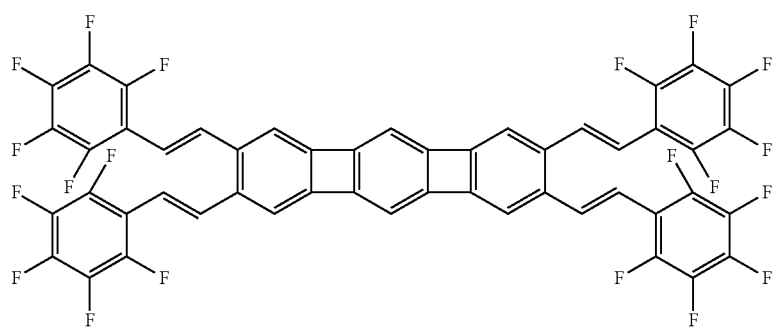

-continued
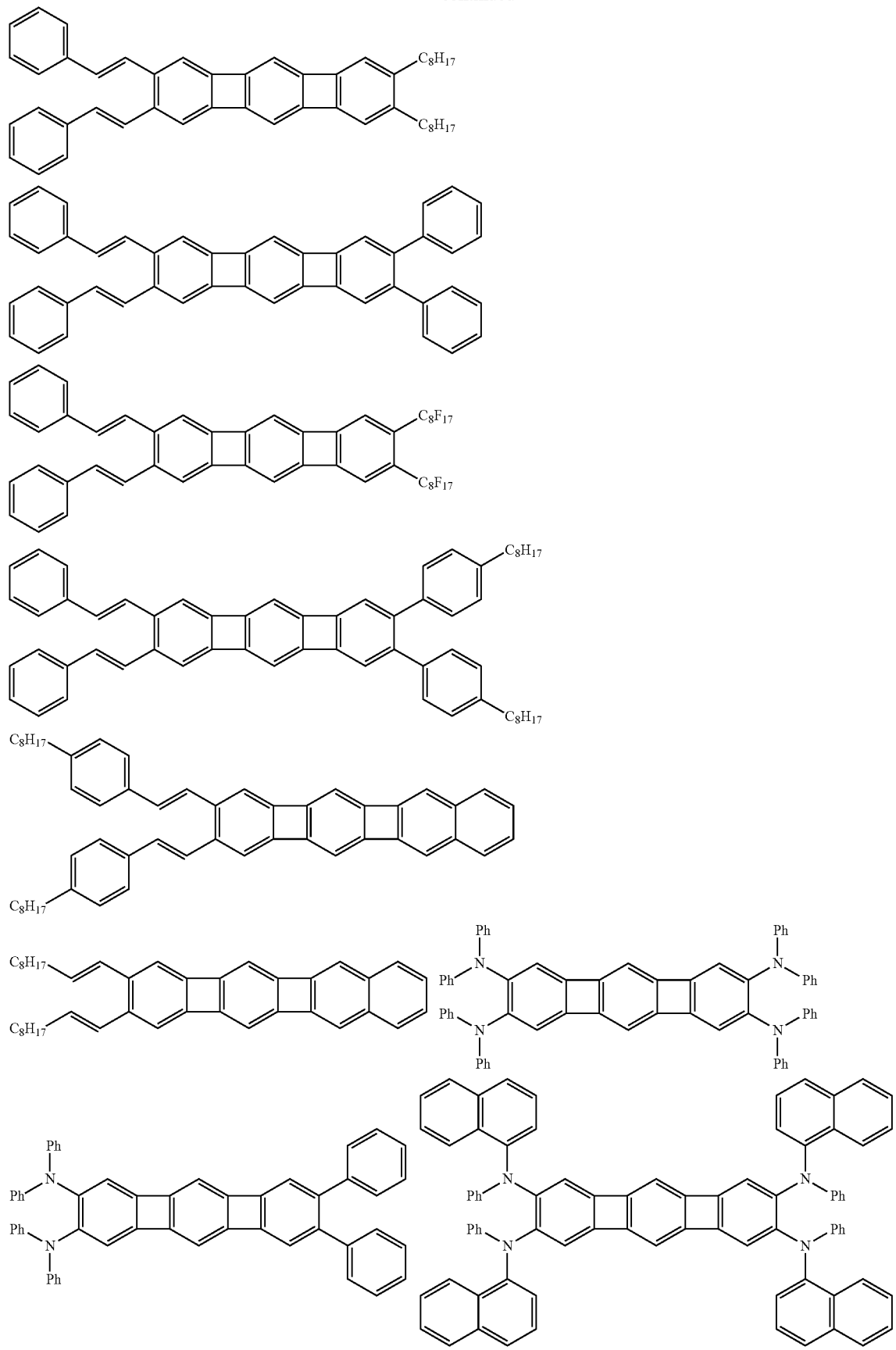

-continued
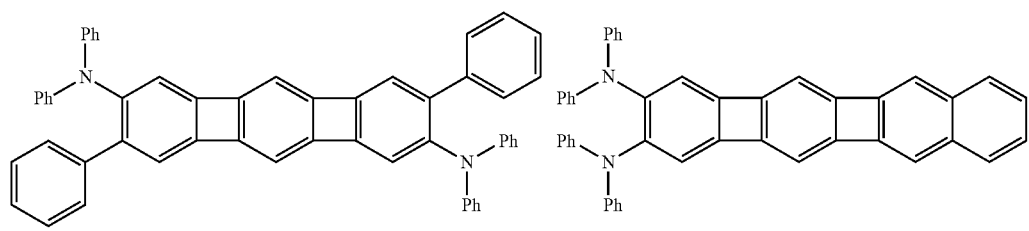
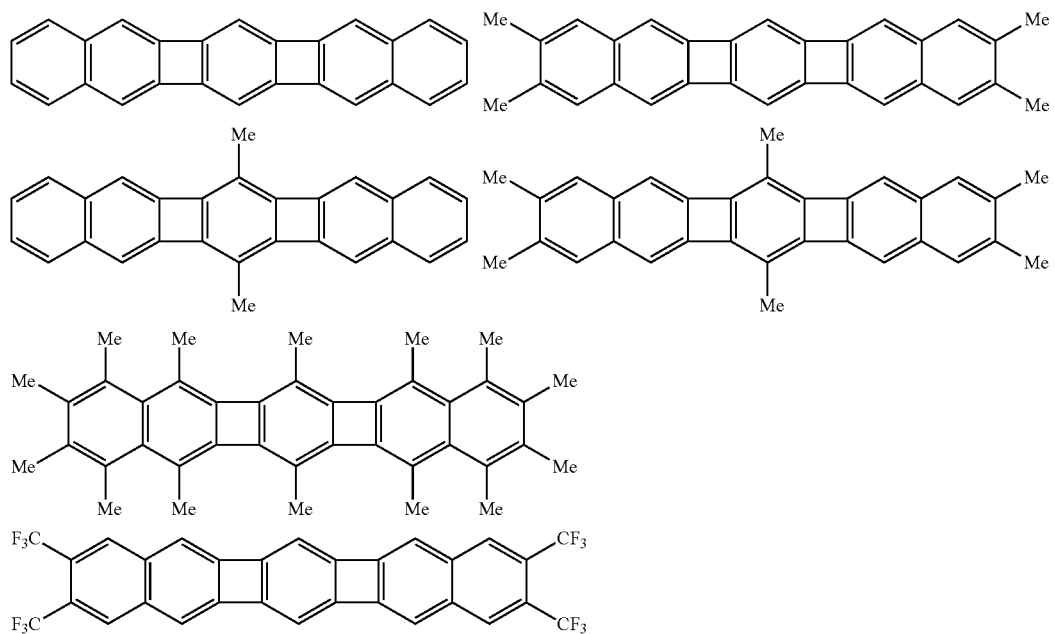
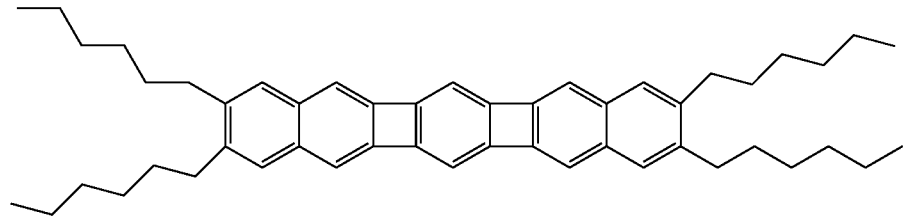
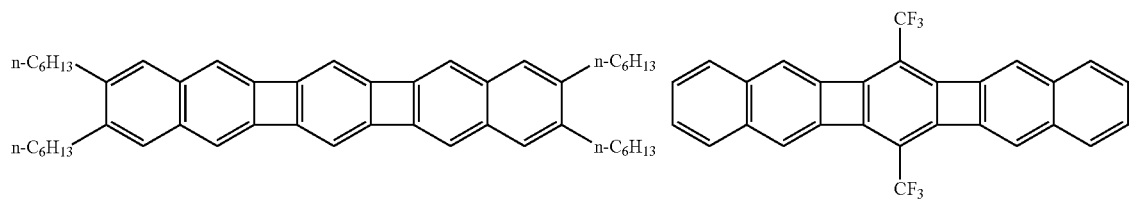
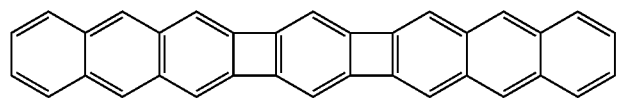
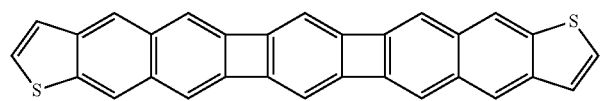
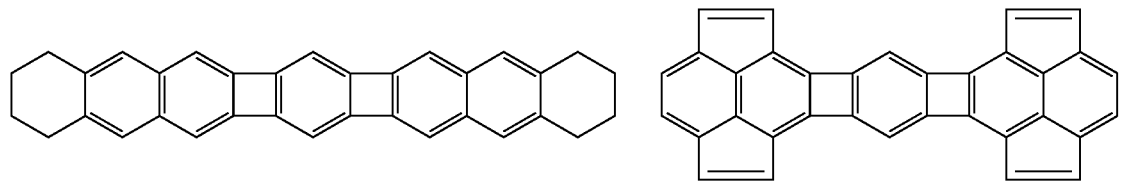

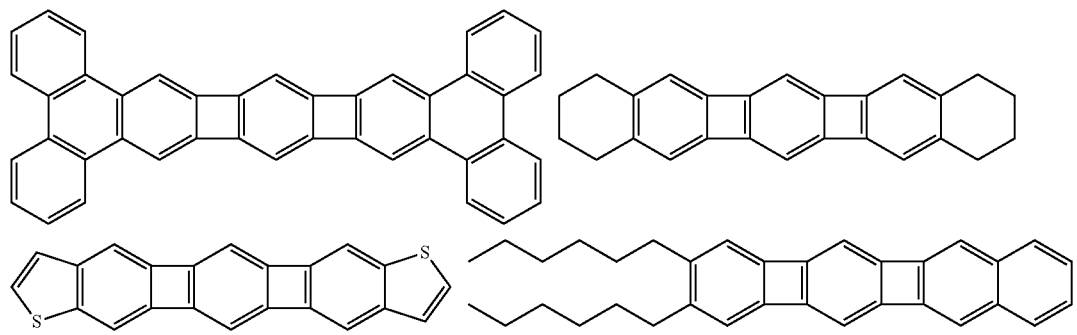
[ka 8]
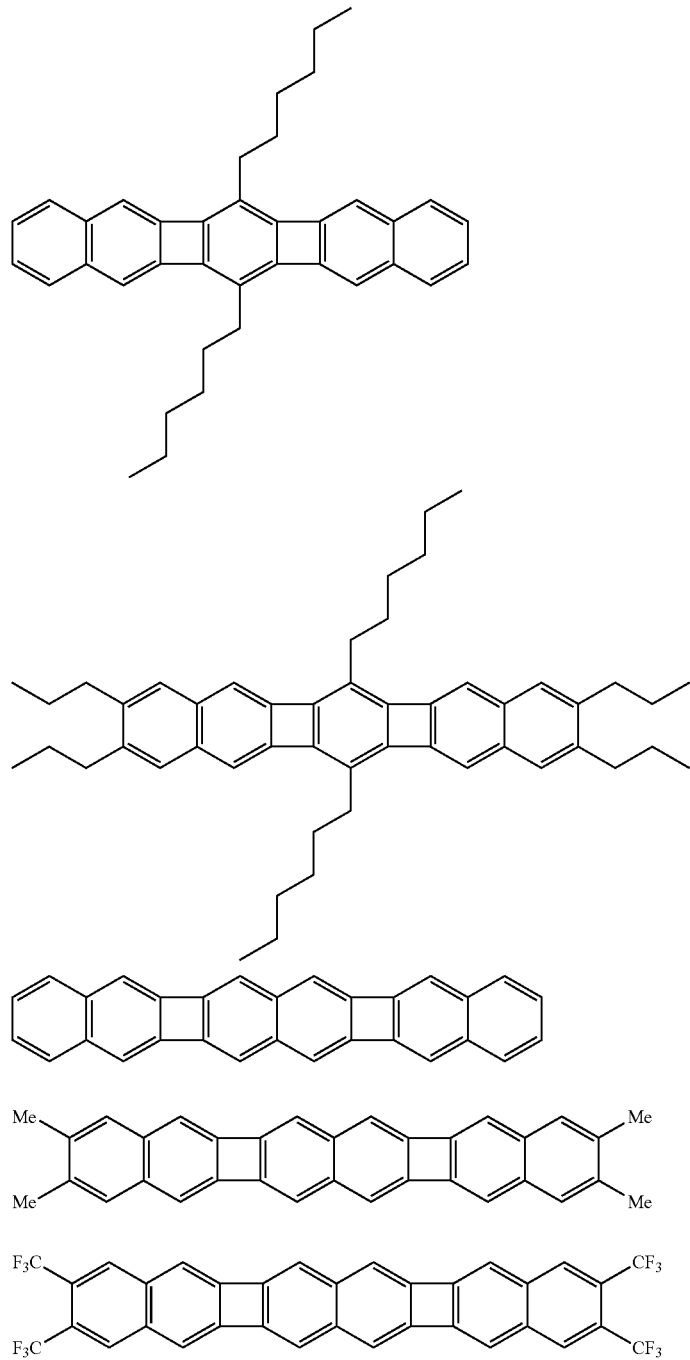

-continued
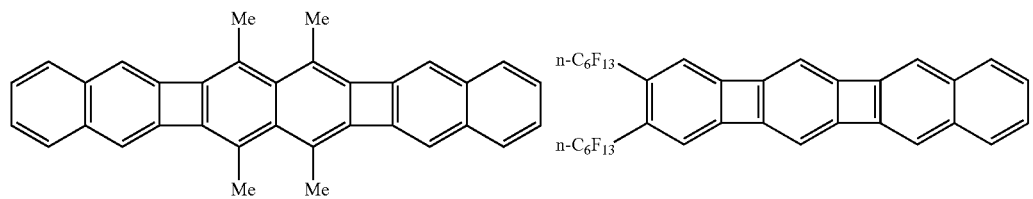
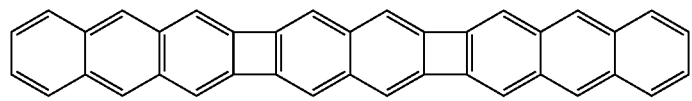
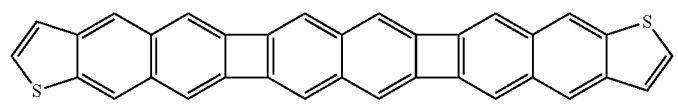
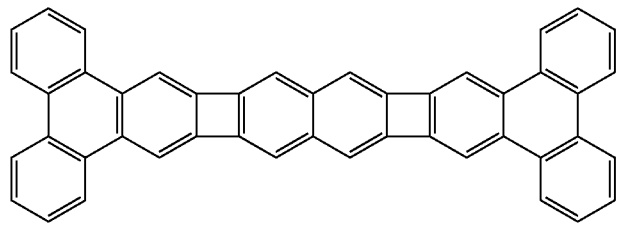
[ka 9]
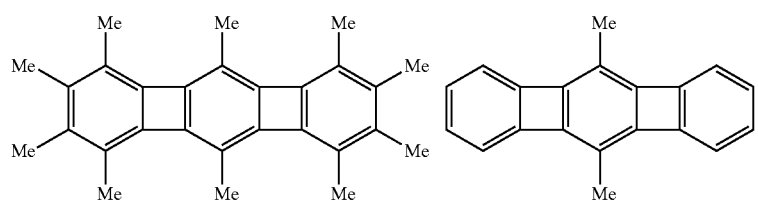
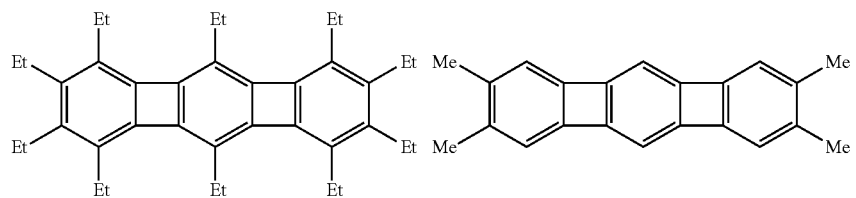
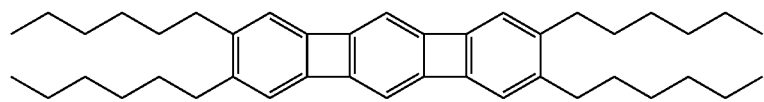
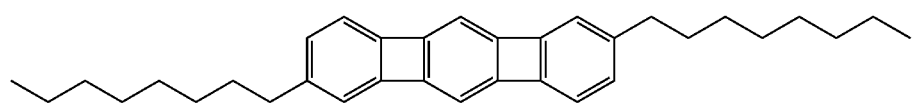

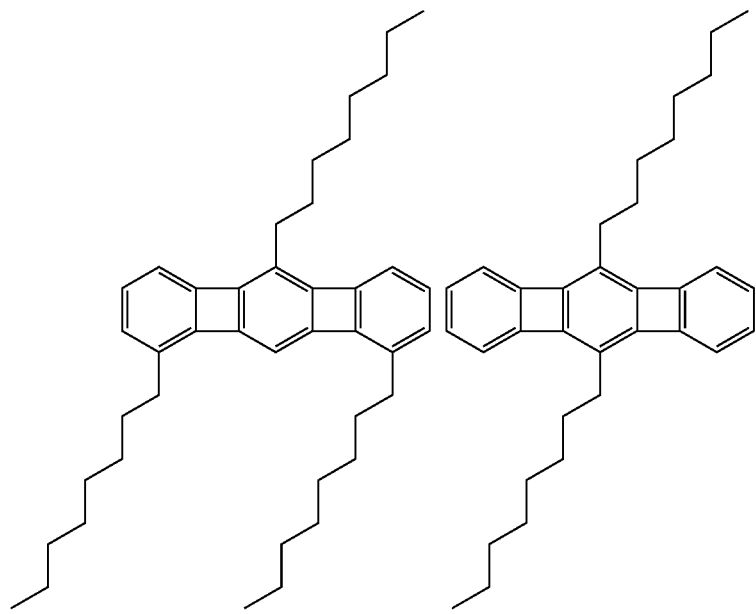

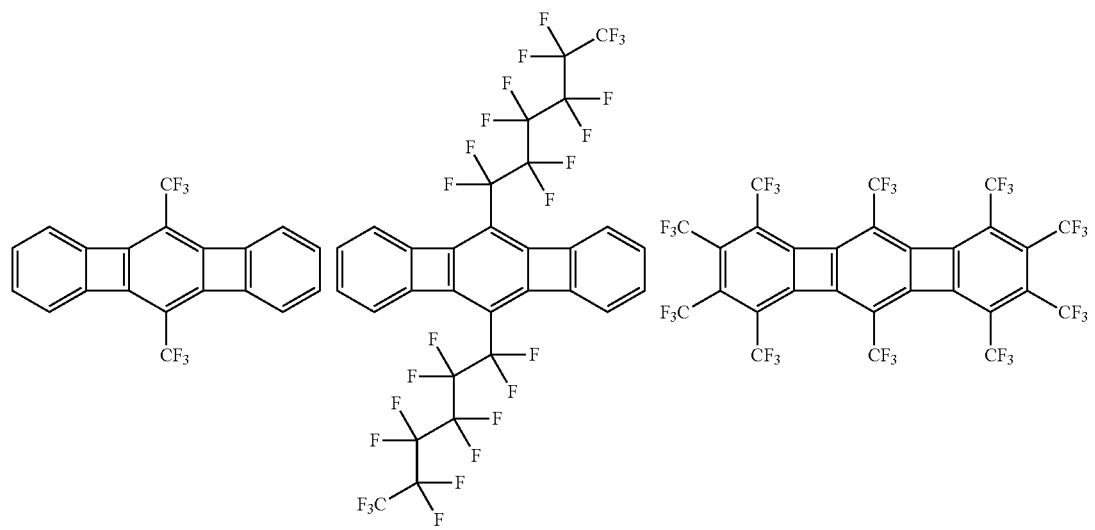

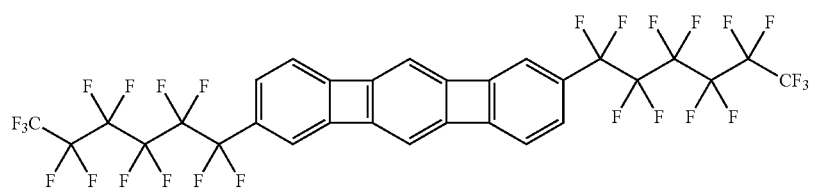

(Process for Producing Terphenylene Derivative)

The following will describe the process for producing the terphenylene derivative represented by the formula (1) of the invention.

The terphenylene derivative represented by the formula (1) of the invention can be produced by tetralithiating a tetrahaloterphenyl derivative represented by the following formula (2) with a lithiating agent and subsequently treating the resulting compound with a copper compound:

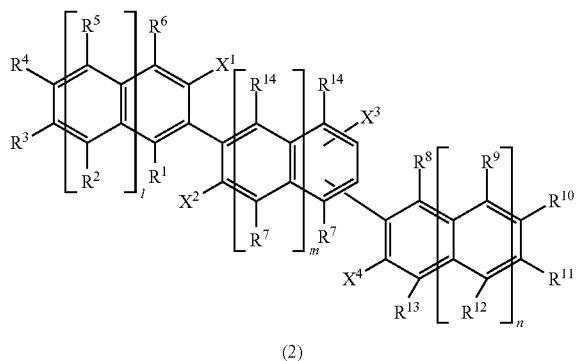

(2)

wherein the substituents $X^1$ to $X^4$ represent a bromine atom, an iodine atom, or a chlorine atom; the substituents $R^1$ to $R^{14}$ are the same or different and each represents a hydrogen atom, a fluorine atom, a chlorine atom, an aryl group having 4 to 30 carbon atoms, an alkynyl group having 3 to 20 carbon atoms, an alkenyl group having 2 to 30 carbon atoms, an alkyl group having 1 to 20 carbon atoms or a halogenated alkyl group having 1 to 20 carbon atoms, or a diarylamino group having 6 to 30 carbon atoms; any two or more of $R^1$ to $R^6$ may be combined with each other and any two or more of $R^8$ to $R^{13}$ may be combined with each other;

and l, m, and n each represents an integer of 0 or 1.

In this connection, the designation of the formula (2) is the general term for the para- and meta-position isomers represented by the following formula (3) and the formula (4):

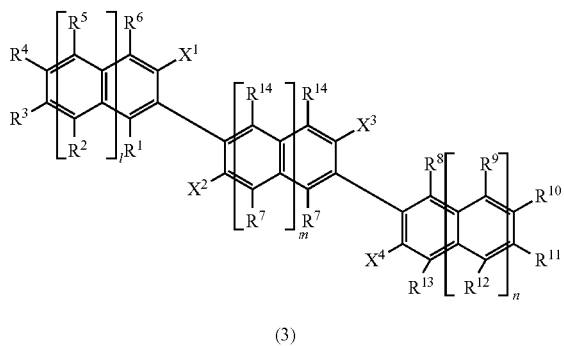

(3)

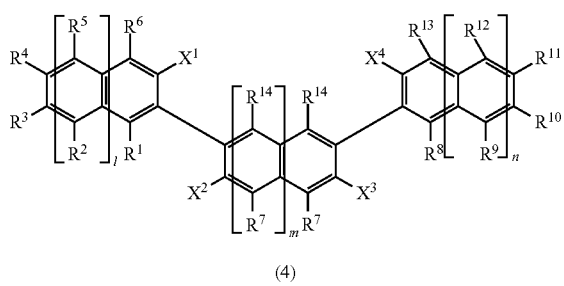

(4)

wherein the substituents $R^1$ to $R^{14}$ and $X^1$ to $X^4$ and the symbols l, m, and n in the formula (3) and the formula (4) represent the same meanings as the substituents and the symbols represented in the formula (2).

In this connection, the term "tetralithiating" herein means replacing each of the four halogens $X^1$ to $X^4$ in the formula (2) with lithium.

In the case where the tetrahaloterphenyl derivative represented by the formula (2) is tetralithiated, the lithiating agent to be used is not particularly limited so far as it can replace the halogens $X^1$ to $X^4$ in the formula (2) with lithium and examples thereof may include alkyllithiums such as n-butyllithium, sec-butyllithium, tert-butyllithium, methyllithium, and hexyllithium; aryllithiums such as phenyllithium, p-tert-butylphenyllithium, p-methoxyphenyllithium, and p-fluorophenyllithium; lithium amides such as lithium diisopropylamide and lithium hexamethyldisilazide; and lithium metal such as lithium powder. Preferred is an alkyllithium and particularly preferred is sec-butyllithium.

The amount of the lithiating agent to be used is in the range of 3 to 20 equivalents, preferably 4 to 15 equivalents, more preferably 5 to 10 equivalents to the tetrahaloterphenyl derivative represented by the formula (2). The use of 3 or more equivalents thereof enhances conversion into tetralithiated one and the use of 20 or less equivalents does not increase the amount of by-products and allows economical tetralithiation.

The tetralithiation reaction is preferably carried out in a solvent. The solvent to be used is not particularly limited and examples thereof are tetrahydrofuran (hereinafter abbreviated as THF), diethyl ether, methyl tert-butyl ether, ethylene glycol dimethyl ether, dioxane, toluene, hexane, cyclohexane, and the like. Particularly preferred is THF. Also, these solvents may be used singly or as a mixture of two or more thereof. The temperature for the tetralithiation reaction is from −100 to 50° C., preferably from −90° C. to 20° C. The reaction time is from 1 to 120 minutes, preferably from 1 to 60 minutes. In this connection, the progress of the tetralithiation reaction can be monitored by taking out a portion of the reaction liquid and, after stopping the reaction with water, analyzing it by gas chromatography.

The tetralithium salt formed by the tetralithiation reaction is subsequently reacted with a copper compound. For such a reaction with a cooper compound, either of a method of reacting the reaction mixture containing the tetralithium salt formed by the above tetralithiation reaction with direct use of the copper compound or a method of once isolating the formed tetralithium salt and then reacting it with the copper compound may be used.

The copper compound for use in the reaction of the tetralithium salt with the cooper compound is not particularly limited and examples thereof may include divalent copper compounds such as copper(II) chloride, copper(II) bromide, copper(II) iodide, copper(II) acetate, and copper(II) acetylacetonate; monovalent copper compounds such as copper(I) chloride, copper(I) bromide, copper(I) iodide, and copper(I) acetate. Preferred is a divalent copper compound, particularly preferred is a copper(II) chloride.

The reaction with the copper compound is preferably carried out in a solvent. The solvent to be used is not particularly limited and examples thereof are THF, diethyl ether, methyl tert-butyl ether, ethylene glycol dimethyl ether, diglyme, dioxane, toluene, hexane, cyclohexane, and the like. Particularly preferred is THF. Also, the amount of the copper compound to be used is from 1 to 20 equivalents, preferably 4 to 15 equivalents to the tetrahaloterphenyl derivative represented by the formula (2). The temperature for the reaction with the copper compound is from −100 to 50° C., preferably from −90° C. to 30° C. and the reaction time is from 1 to 30 hours, preferably from 1 to 18 hours.

The production of the terphenylene derivative of the formula (1) of the invention is preferably carried out in an inert atmosphere, such as nitrogen or argon.

In the process for producing the terphenylene derivative of the formula (1) of the invention, the tetrahaloterphenyl derivative of the formula (2) is tetralithiated and then may be reacted with zinc chloride and subsequently treated with the copper compound.

The terphenylene derivative represented by the formula (1) of the invention can be also produced by subjecting the tetrahaloterphenyl derivative represented by the formula (2) to a Grignard reaction with a Grignard reagent, followed by treatment with the copper compound. Examples of the Grignard reagent to be used may include Mg metal, or alkyl Grignard reagents such as ethylmagnesium bromide and isopropylmagnesium bromide. Preferred is Mg metal. The form of the Mg metal is not particularly limited and examples thereof include shavings, ribbons, and granules.

The Grignard reagent is used, for example, in the case of Mg metal, in the range of 1.8 to 20 equivalents to the tetrahaloterphenyl derivative represented by the formula (2). The Grignard reaction is preferably carried out in a solvent. The solvent to be used is not particularly limited and the solvents used in the above tetralithiation reaction may be mentioned, for example. The temperature for the Grignard reaction is from −20 to 120° C. and the reaction time is in the range of 1 to 360 minutes.

The tetramagnesium salt formed by the Grignard reaction is then reacted with the copper compound. Such a reaction with the copper compound can be carried out under the conditions used in the above tetralithiation reaction.

The thus obtained terphenylene derivative represented by the formula (1) of the invention can be further purified. The method for purification is not particularly limited and methods by column chromatography, recrystallization, or sublimation may be mentioned.

The tetrahaloterphenyl derivative represented by the formula (2) to be used as a starting material in the process for producing the terphenylene derivative represented by the formula (1) of the invention includes a para-form represented by the formula (3) and a meta-form represented by the formula (4). However, as the starting material for the terphenylene derivative represented by the formula (1), either of the two isomers of these para- and meta-forms can be used and also even a mixture of the two isomers in any ratio can be used as the starting material without troubles (Tetrahaloterphenyl Derivative)

The following will describe the tetrahaloterphenyl derivative represented by the formula (2) to be used as a starting material in the process for producing the terphenylene derivative represented by the formula (1) of the invention:

[ka 13]

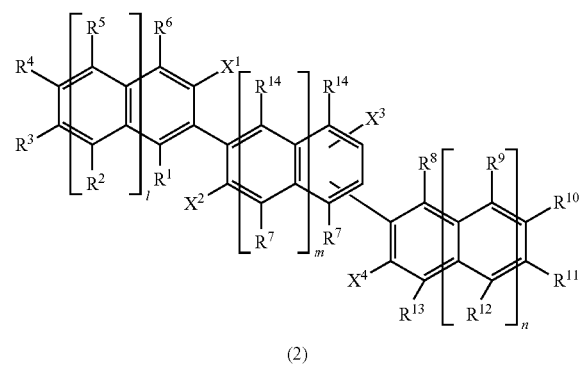

(2)

wherein the substituents $X^1$ to $X^4$ represent a bromine atom, an iodine atom, or a chlorine atom; the substituents $R^1$ to $R^{14}$ are the same or different and each represents a hydrogen atom, a fluorine atom, a chlorine atom, an aryl group having 4 to 30 carbon atoms, an alkynyl group having 2 to 20 carbon atoms, an alkenyl group having 2 to 30 carbon atoms, an alkyl group having 1 to 20 carbon atoms or a halogenated alkyl group having 1 to 20 carbon atoms, or a diarylamino group having 8 to 30 carbon atoms; any two or more of $R^1$ to $R^6$ may be combined with each other and any two or more of $R^8$ to $R^{13}$ may be combined with each other;

and l, m, and n each represents an integer of 0 or 1.

In this connection, the designation of the formula (2) is the general term for the para- and meta-position isomers represented by the following formula (3) and the formula (4):

[ka 14]

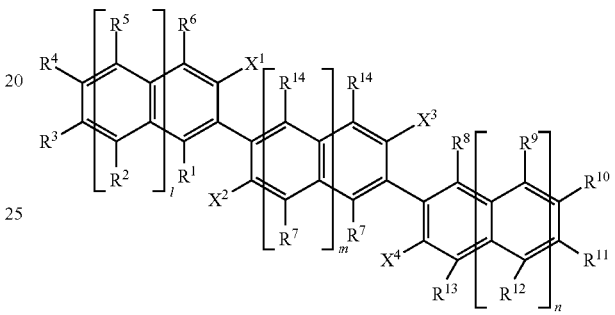

(3)

[ka 15]

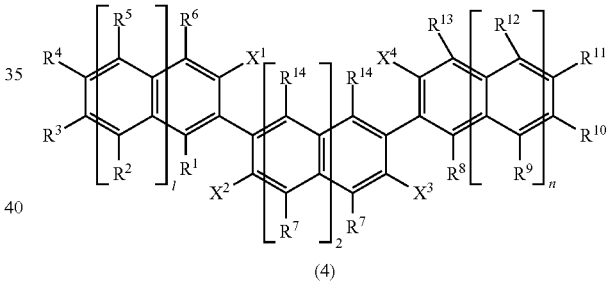

(4)

wherein the substituents $R^1$ to $R^{14}$ and $X^1$ to $X^4$ and the symbols l, m, and n in the formula (3) and the formula (4) represent the same meanings as the substituents and the symbols represented in the formula (2).

Moreover, the substituents $X^1$ to $X^4$ in the formula (2) of the invention are preferably a bromine atom or an iodine atom, and more preferably a bromine atom.

Furthermore, the substituents $R^3$, $R^4$, $R^{10}$ and $R^{11}$ of the tetrahaloterphenyl derivative represented by the formula (2) of the invention are preferably the same or different and each is a group selected from the group consisting of an aryl group having 4 to 30 carbon atoms, an alkynyl group having 2 to 20 carbon atoms, an alkenyl group having 2 to 30 carbon atoms, an alkyl group having 1 to 20 carbon atoms or a halogenated alkyl group having 1 to 20 carbon atoms, and a diarylamino group having 8 to 30 carbon atoms, more preferably a group selected from the group consisting of an aryl group having 4 to 30 carbon atoms, an alkynyl group having 2 to 20 carbon atoms, and an alkyl group having 1 to 20 carbon atoms or a halogenated alkyl group having 1 to 20 carbon atoms, and particularly preferably a group selected from the group consisting of an aryl group having 4 to 30 carbon atoms and an alkynyl group having 2 to 20 carbon atoms.

A preferable position isomer of the tetrahaloterphenyl derivative represented by the formula (2) of the invention is a para-position isomer of the tetrahaloterphenyl derivative represented by the formula (3).

Moreover, a preferable substitution pattern of the tetrahaloterphenyl derivative represented by the formula (2) of the invention is a tetrahaloterphenyl derivative having a substitution pattern represented by the formula (5) in the substituents $R^1$ to $R^{14}$:

[ka 16]

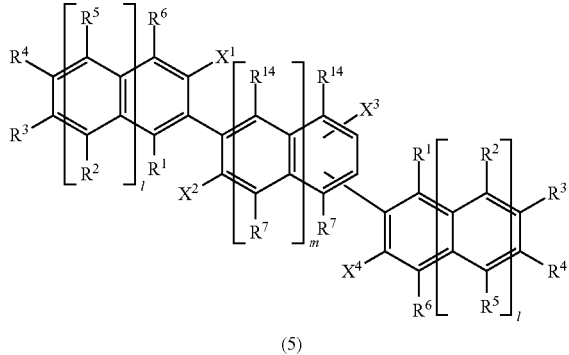

(5)

wherein the substituents $R^1$ to $R^7$, $R^{14}$ and $X^1$ to $X^3$ and the symbols l and m represent the same meanings as the substituents and the symbols represented in the formula (2) and the designation in the formula (5) represents the same meaning as in the formula (2); provided that the substituents designated by the same substituent designations represent that the substituents are substituted by the same substituents.

Namely, the tetrahaloterphenyl derivative represented by the formula (5) is a tetrahaloterphenyl derivative having a substitution pattern wherein the both ends of the derivative ring structure are the same in the substituents represented by the formula (2) of the invention, i.e., $R^8=R^1$, $R^9=R^2$, $R^{10}=R^3$, $R^{11}=R^4$, $R^{12}=R^5$, $R^{13}=R^6$, and $X^4=X^1$.

The tetrahaloterphenyl derivative represented by the formula (2) of the invention is not particularly limited and, for example, the following compounds may be mentioned

[ka 17]

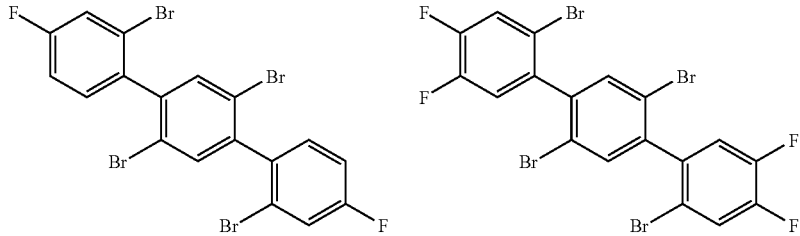

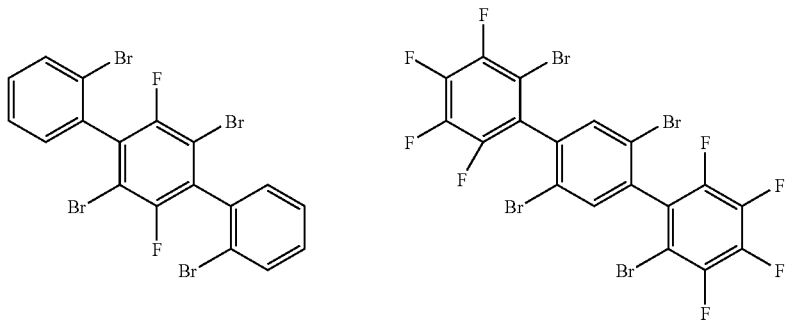

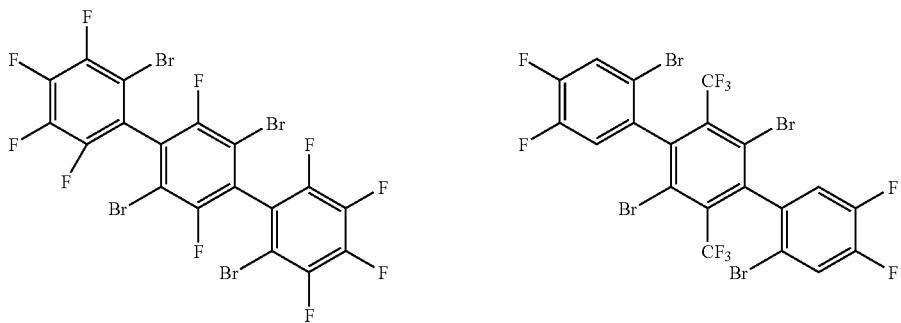

-continued
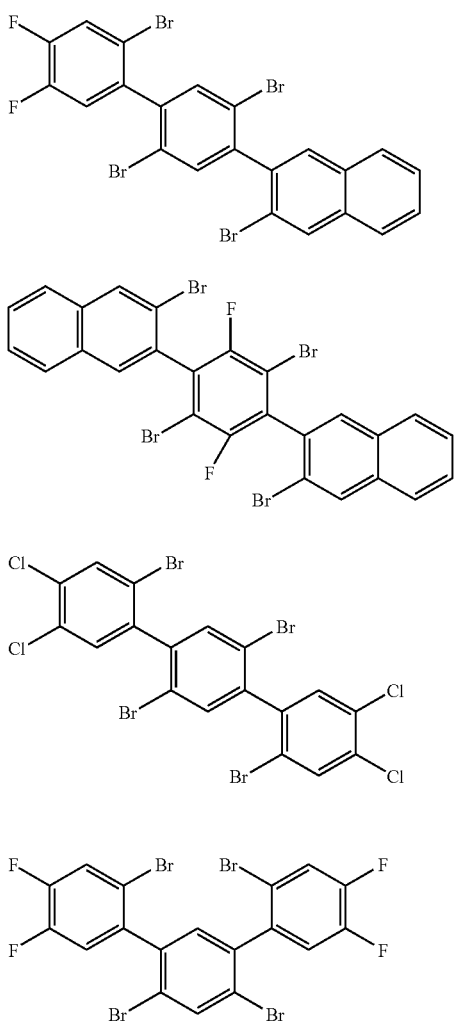
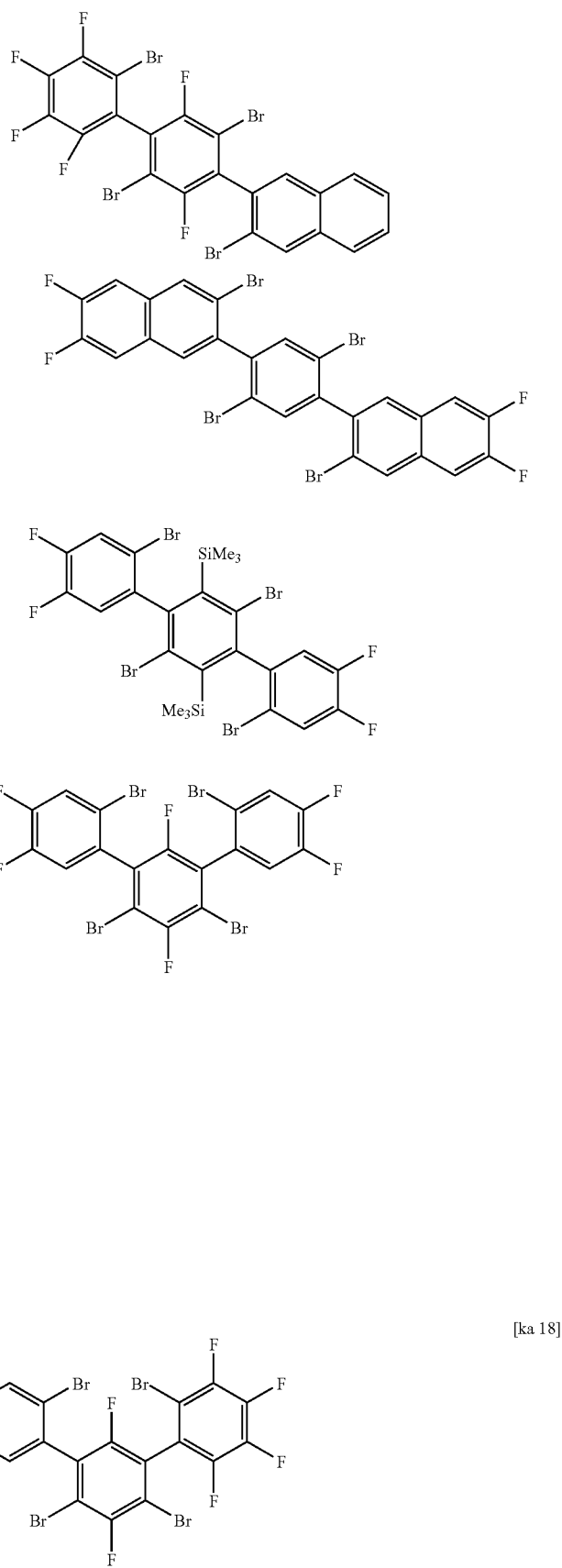
[ka 18]

-continued
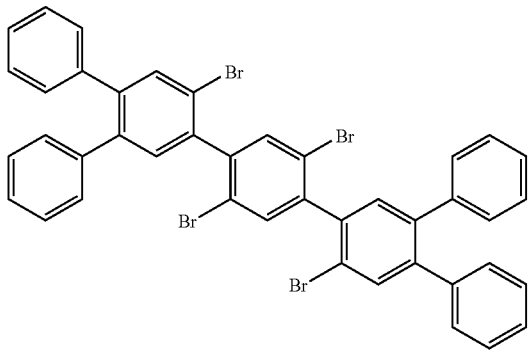
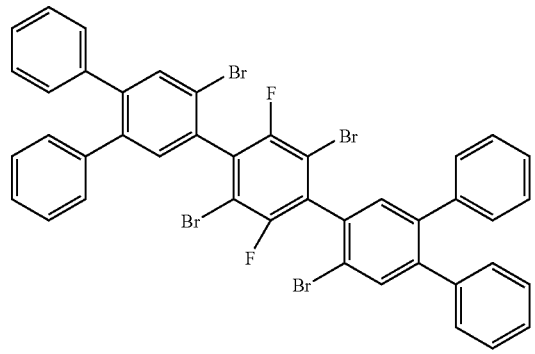
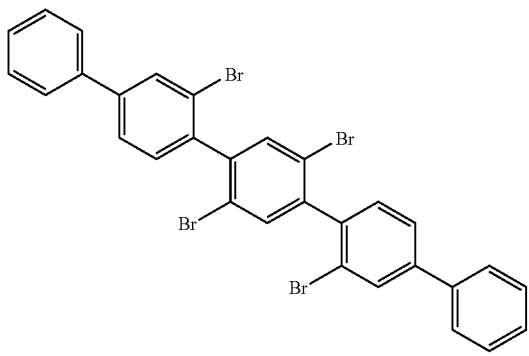
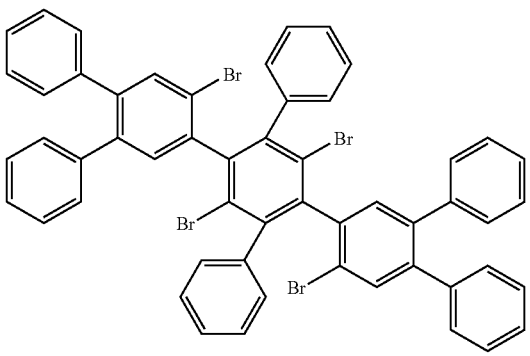
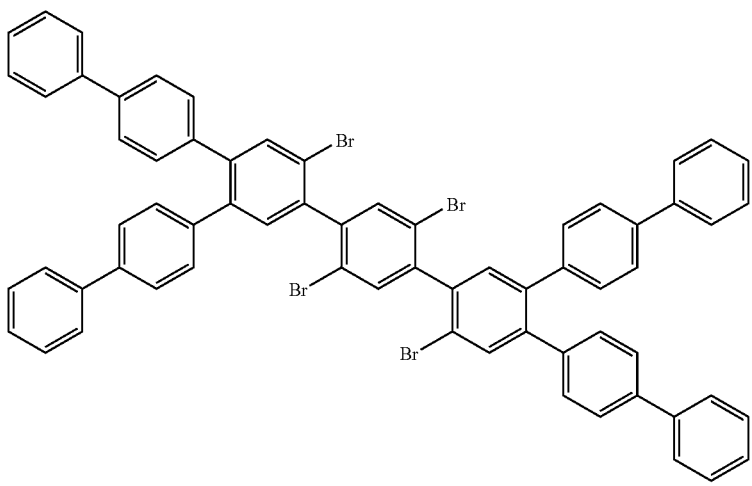
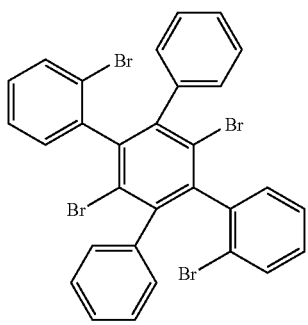
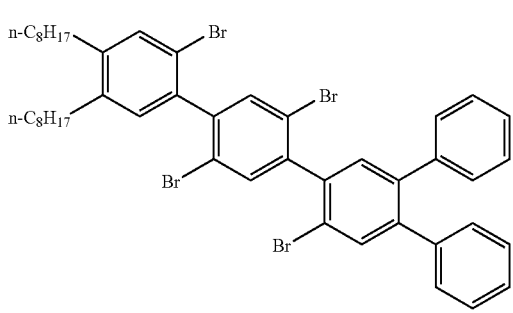

-continued
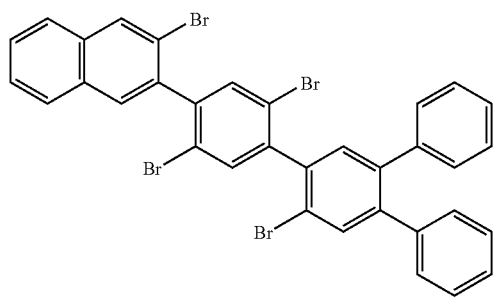
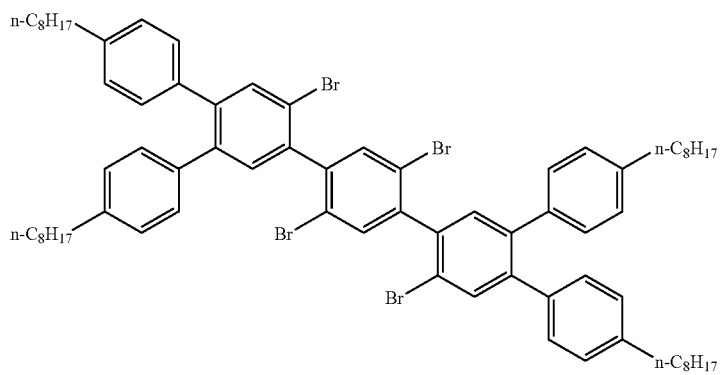
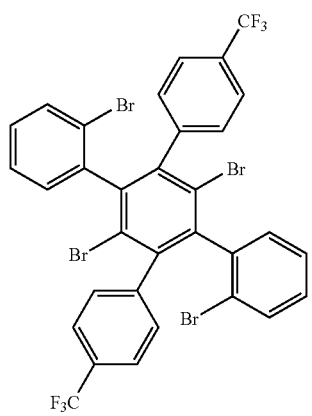
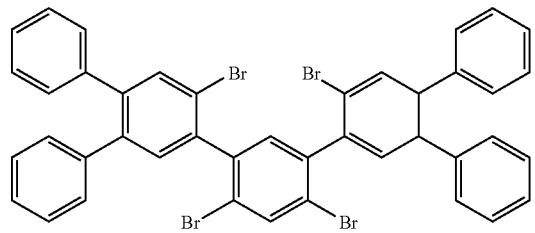
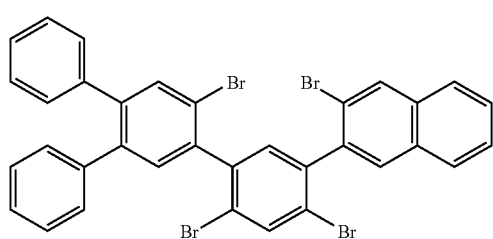
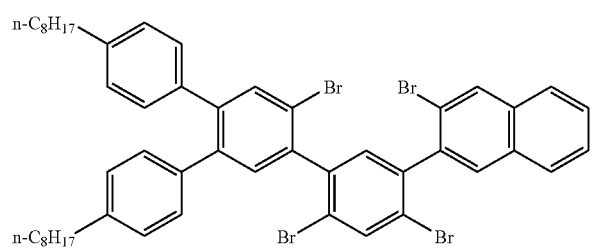
[ka 19]
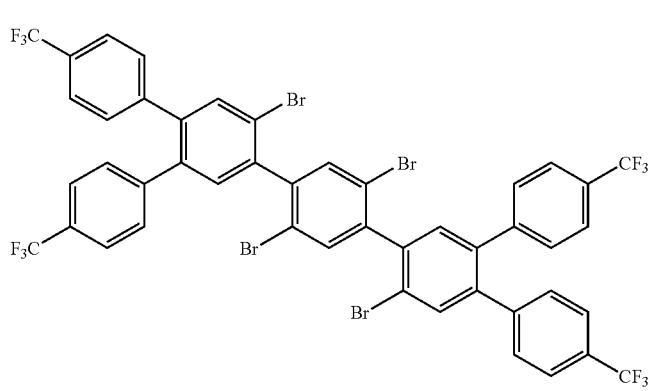

-continued
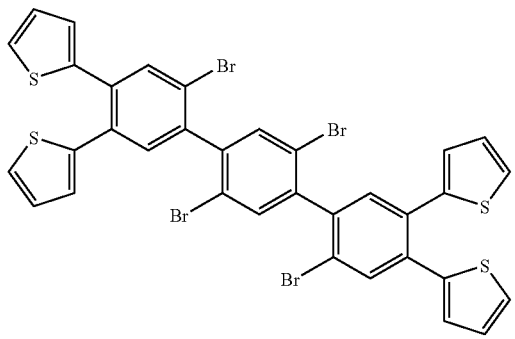
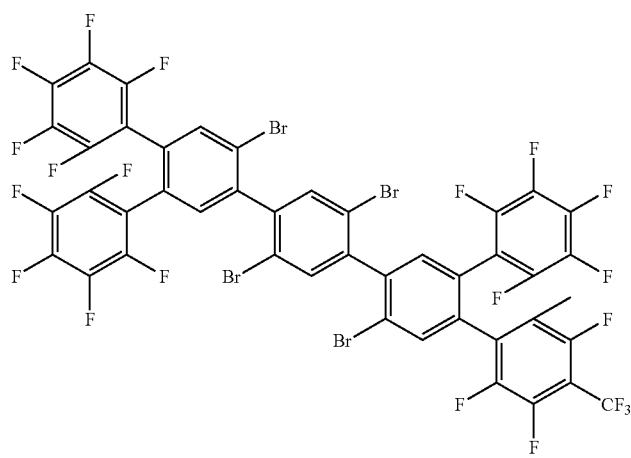
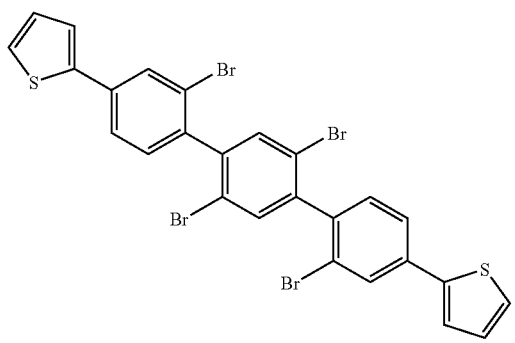
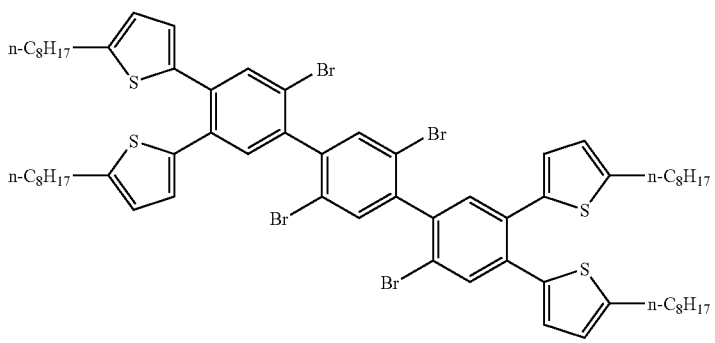

-continued
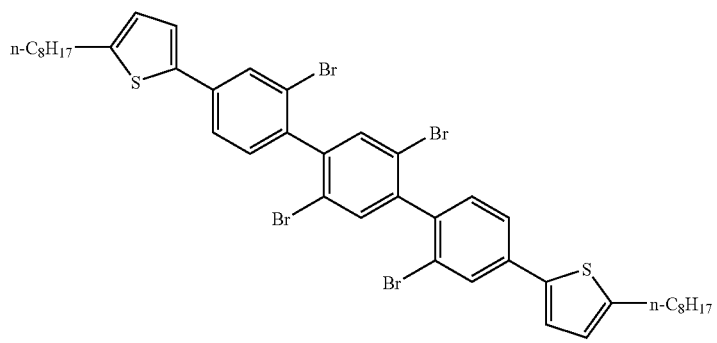
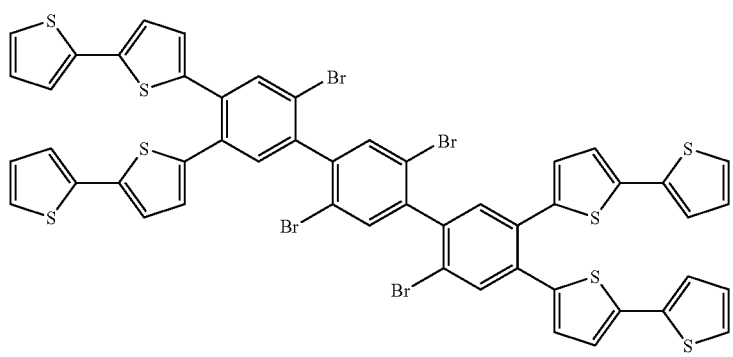
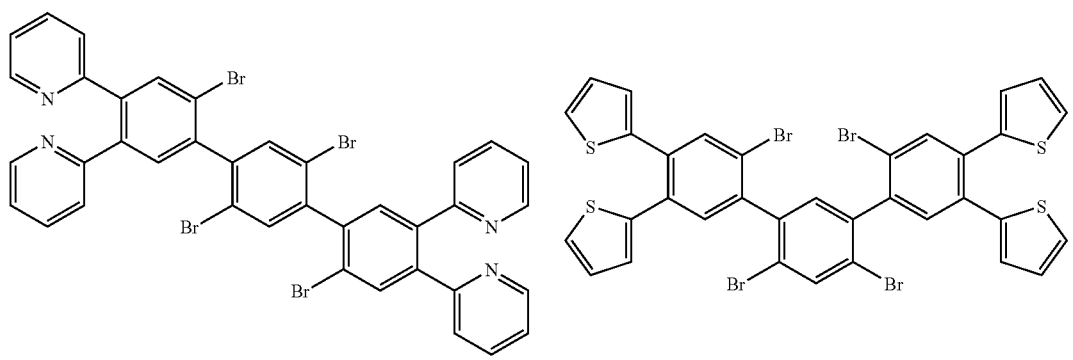
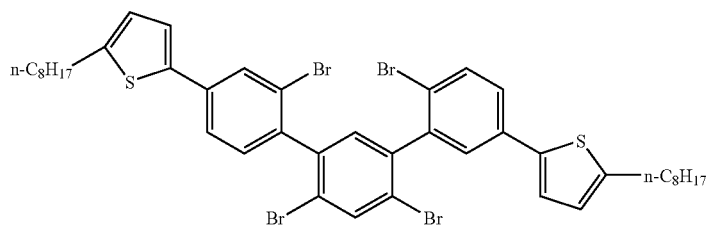
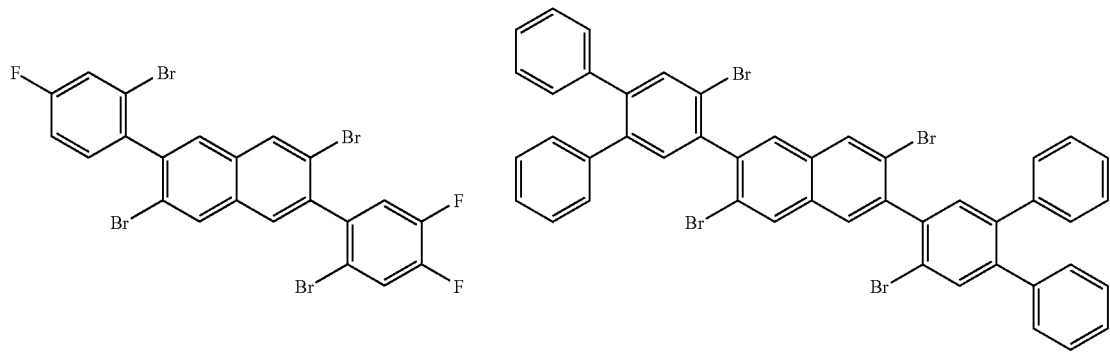

-continued
[ka 20]
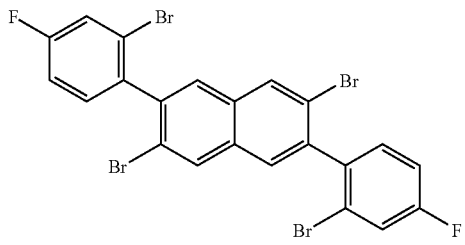
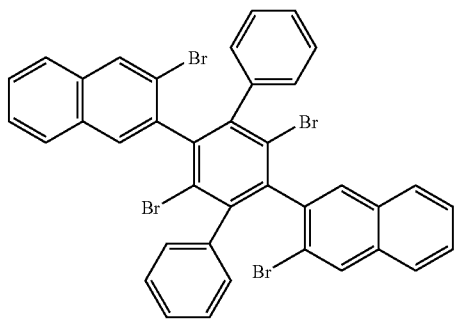
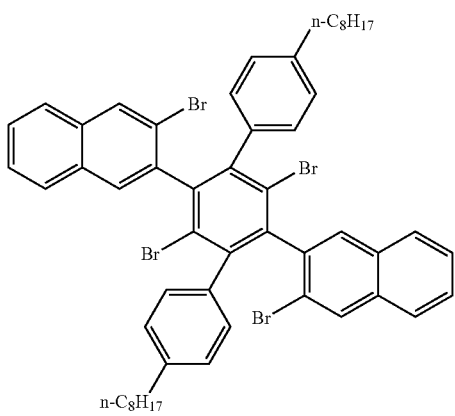
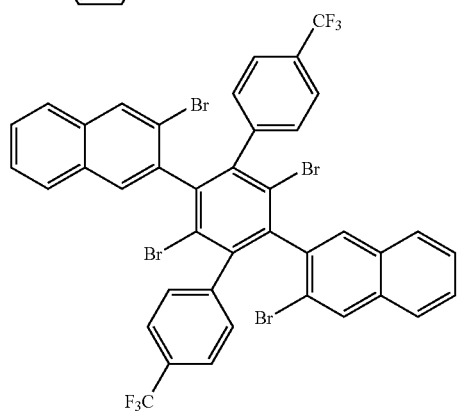
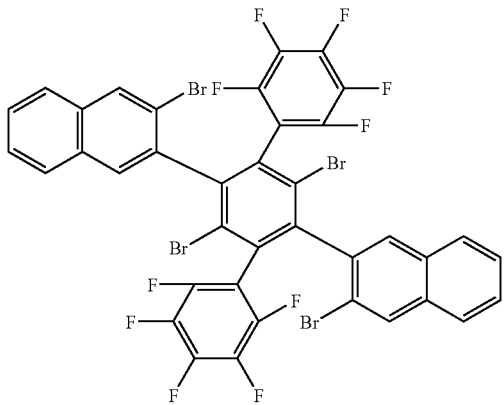
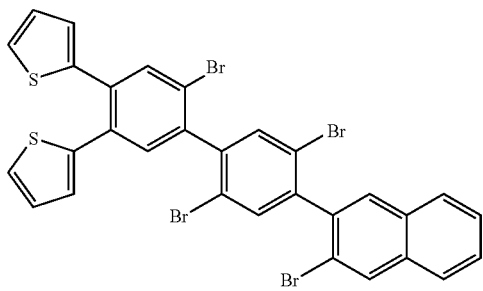
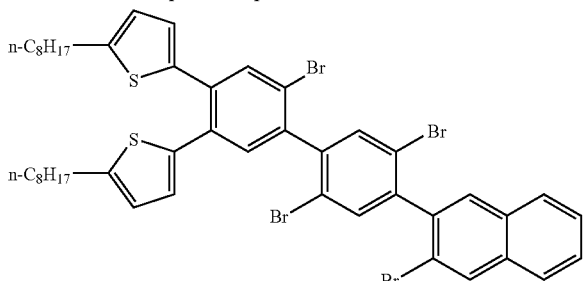
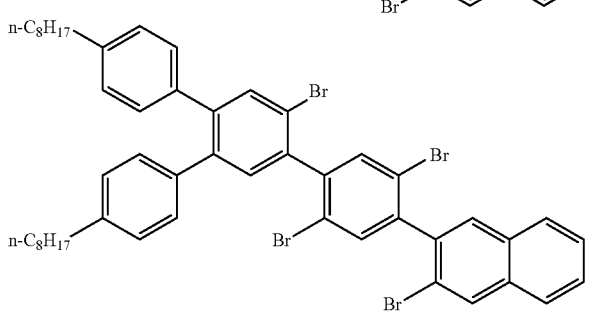

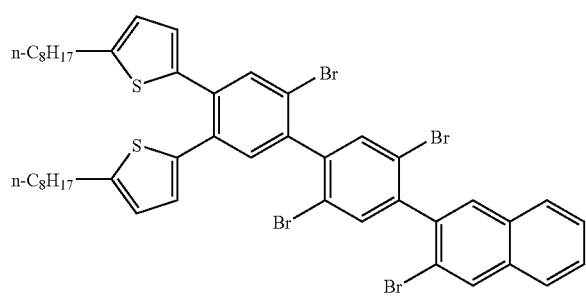
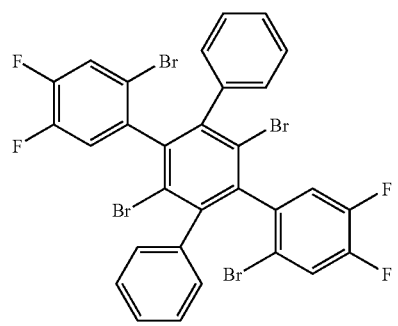
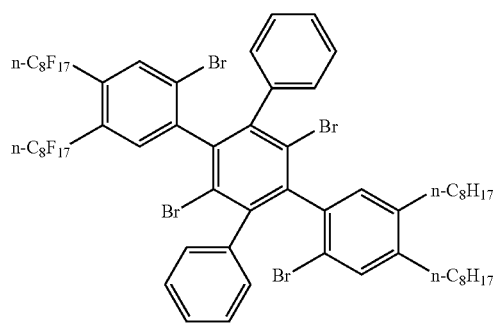
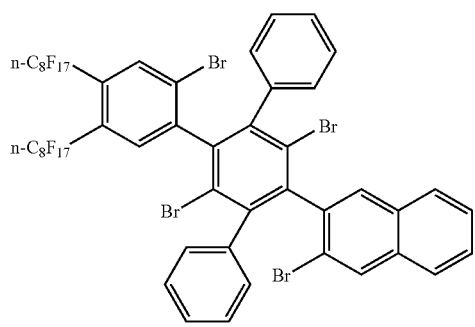
[ka 21]
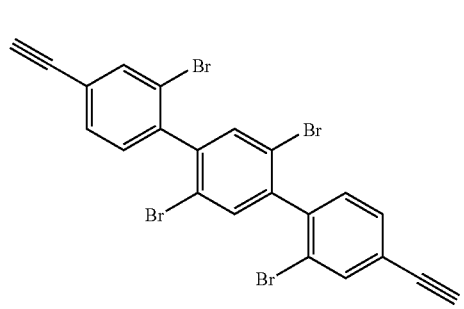
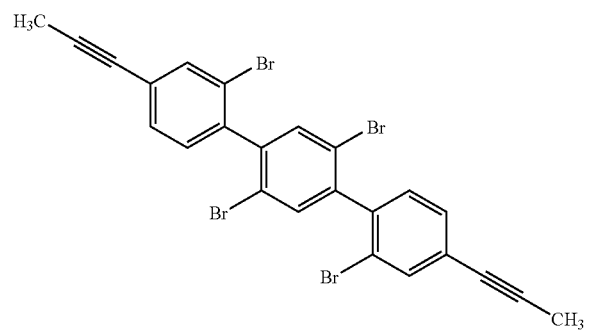
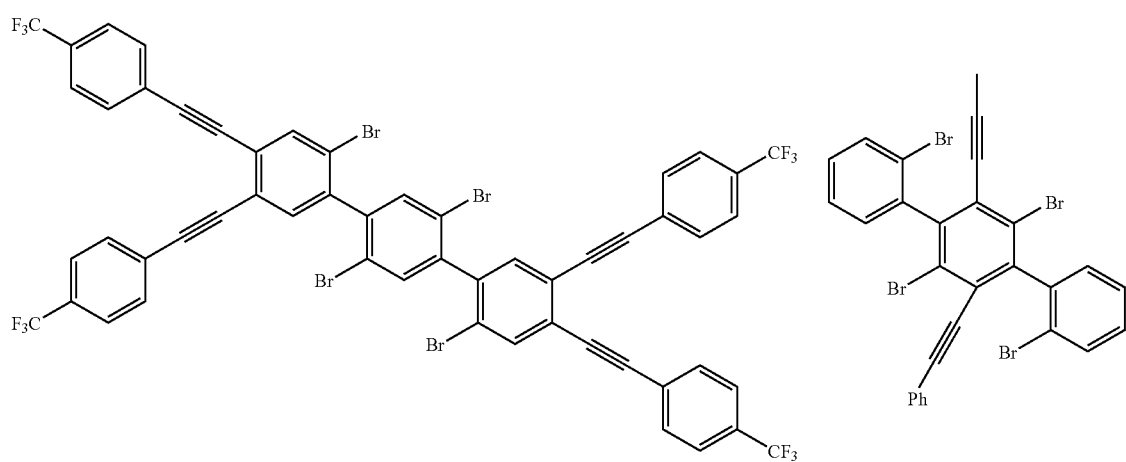

-continued
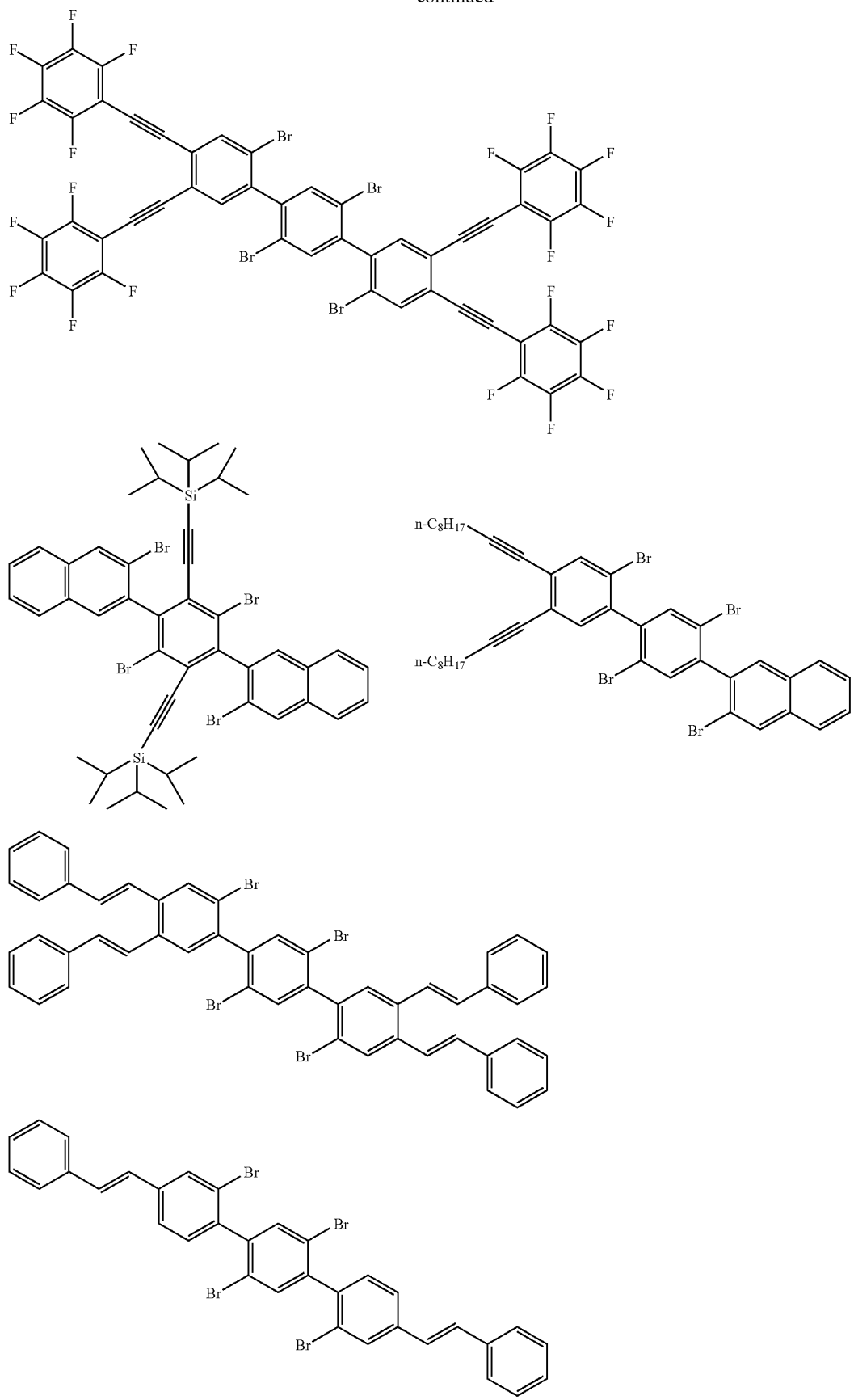
[ka 22]

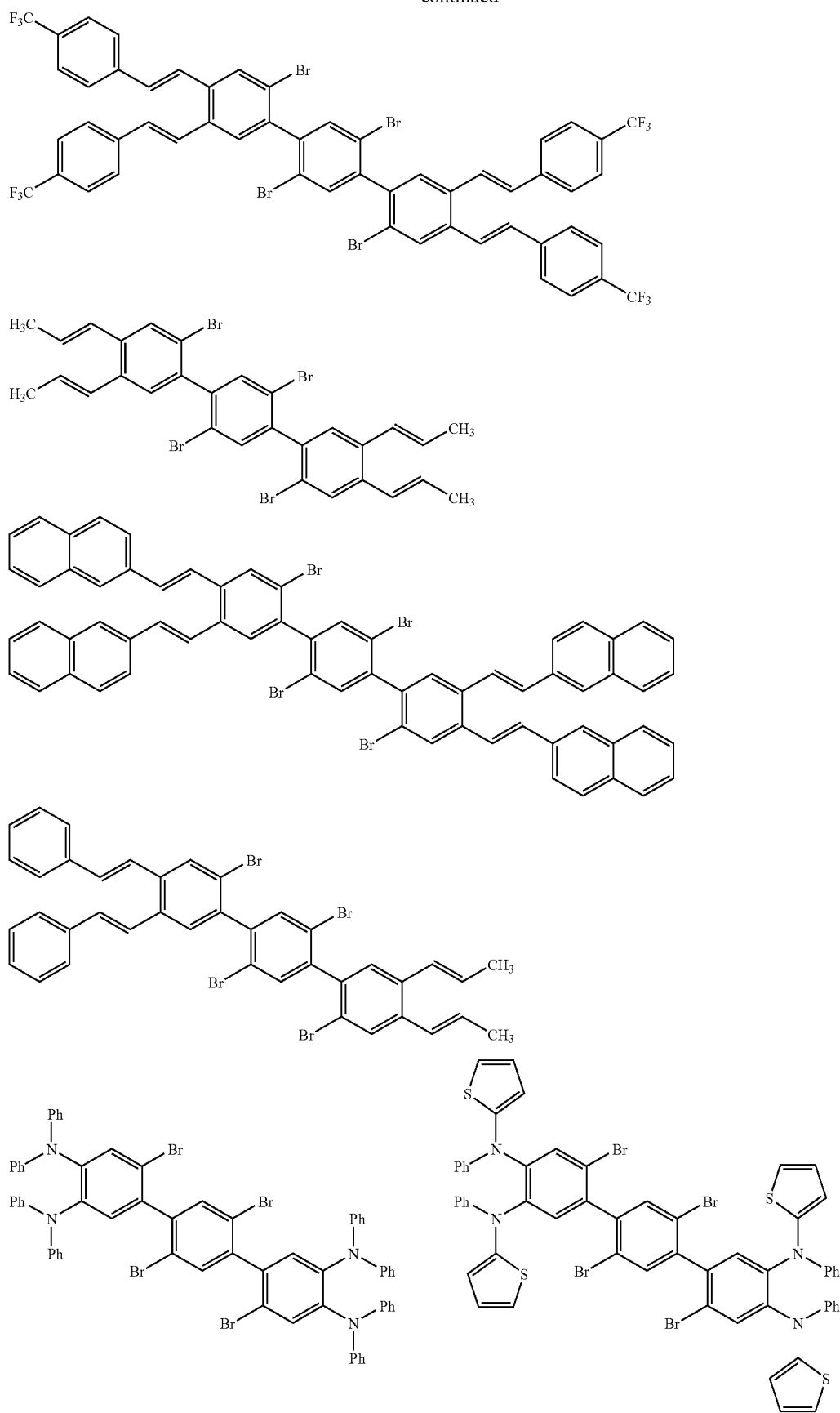

-continued
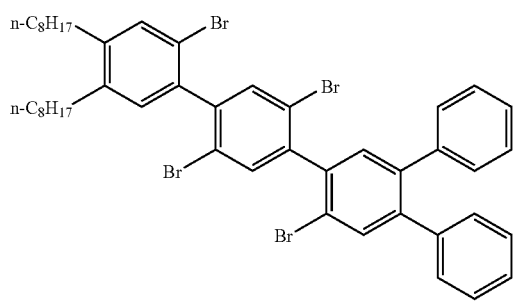
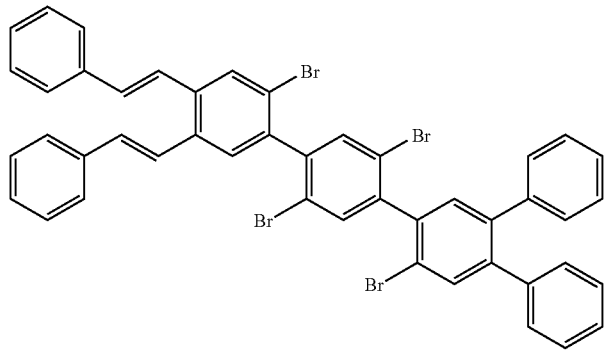
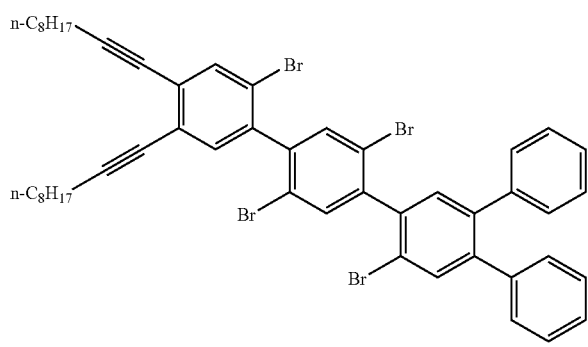
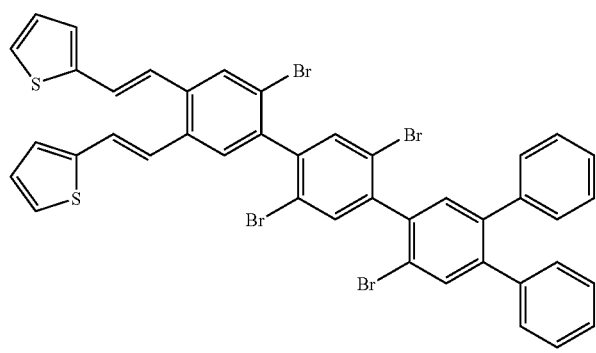
[ka 23]
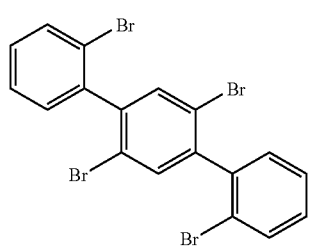 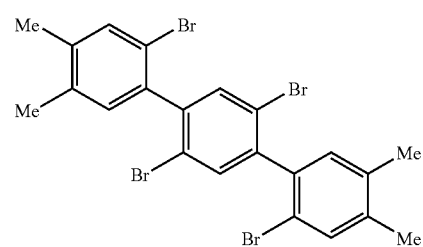 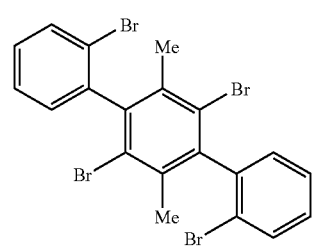

-continued
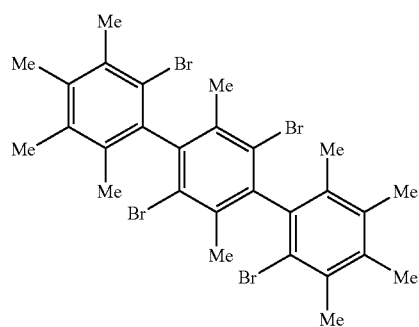
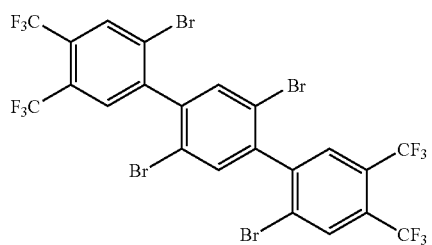
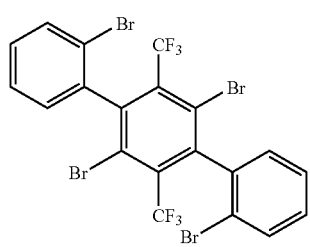
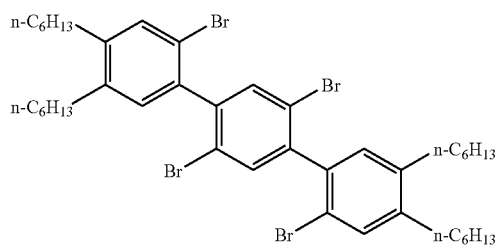
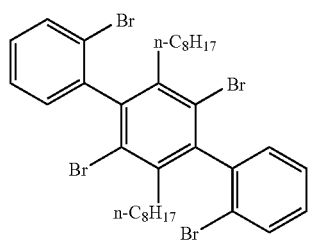
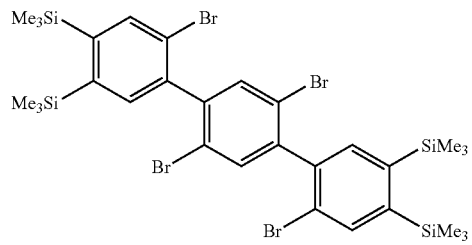
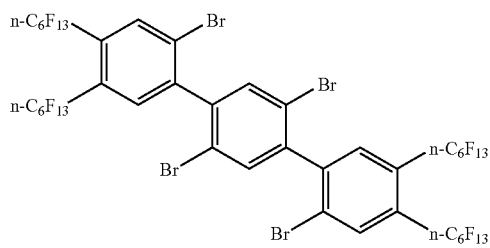
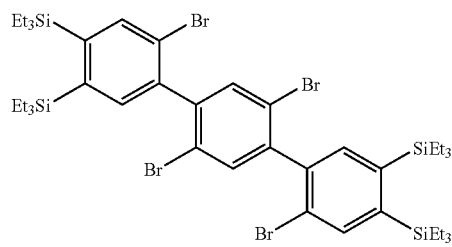
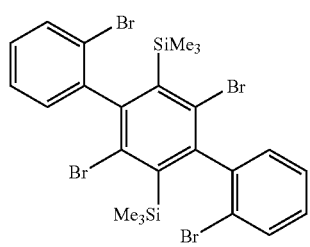
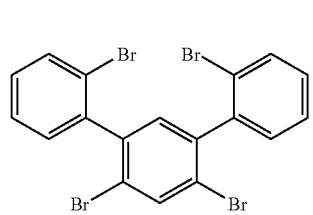
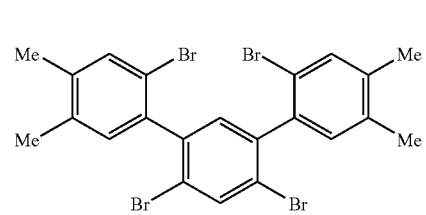
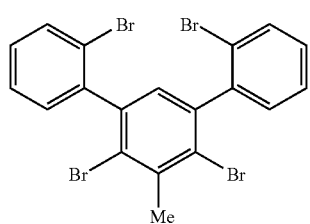
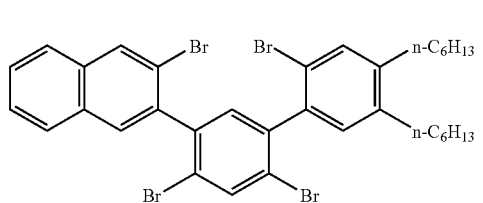

[ka 24]
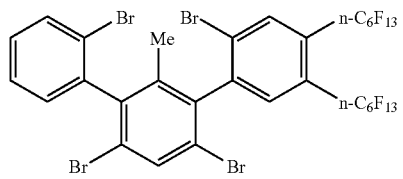
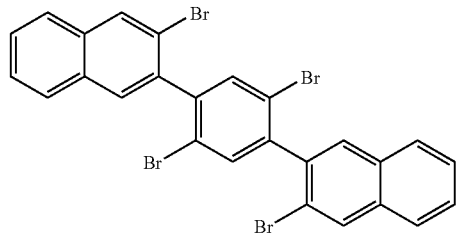
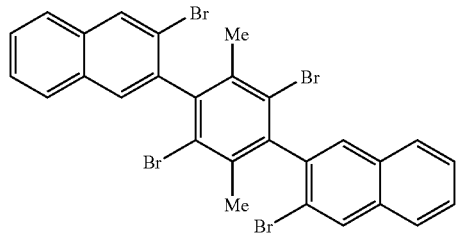
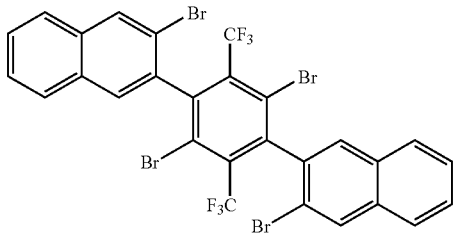
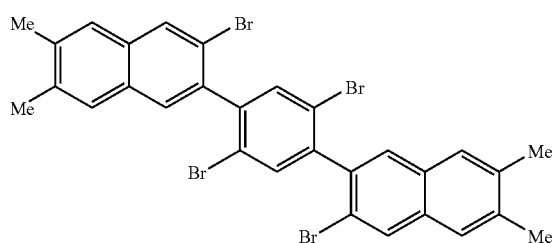
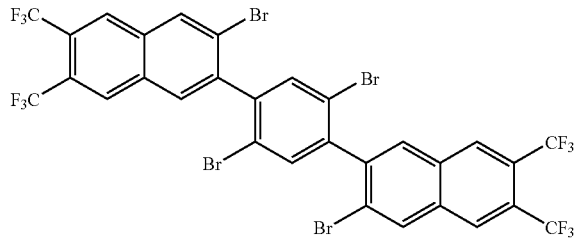
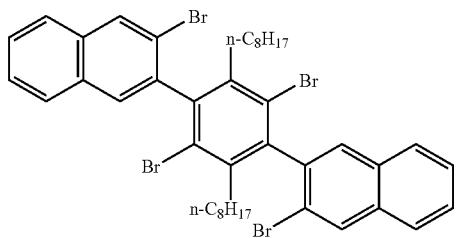
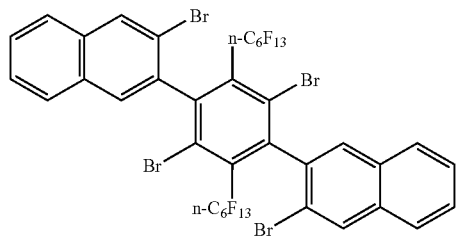
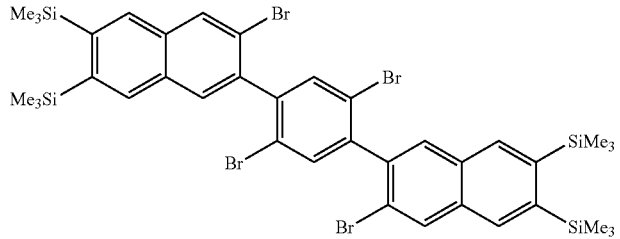
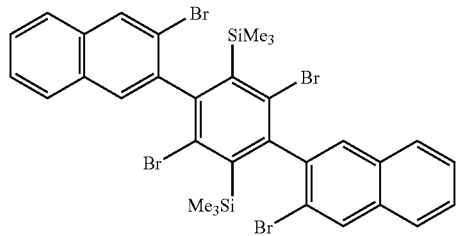
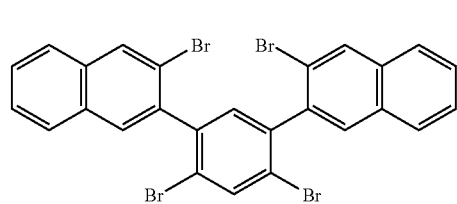
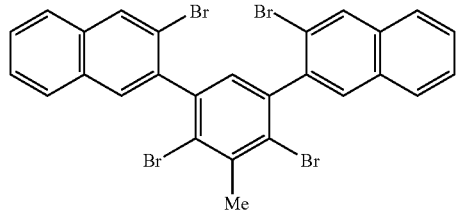
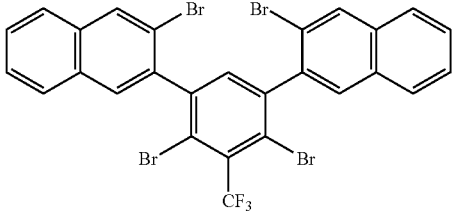

-continued
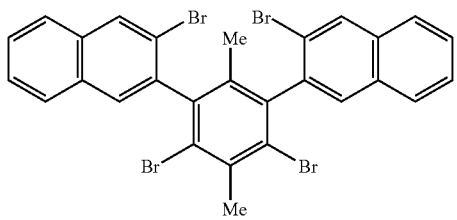
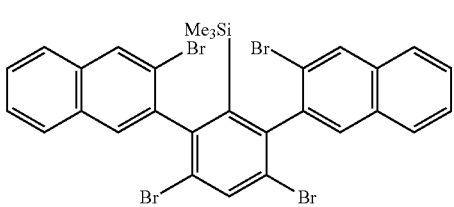
[ka 25]
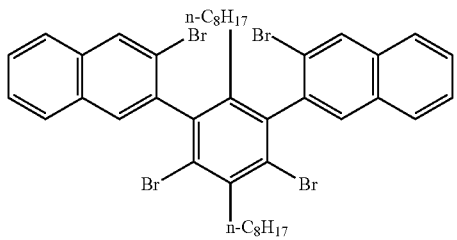
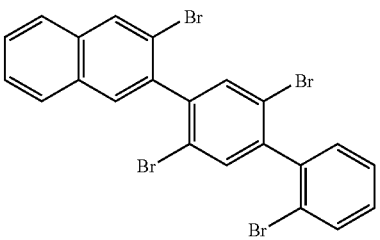
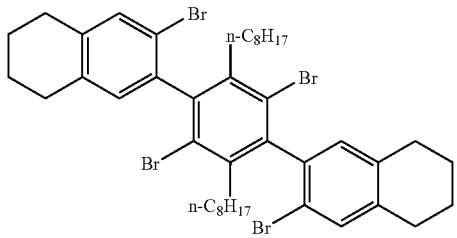
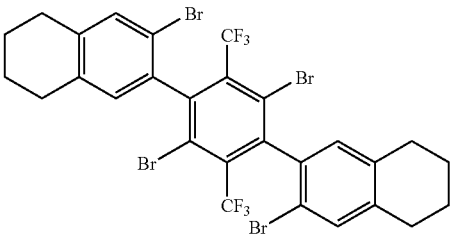
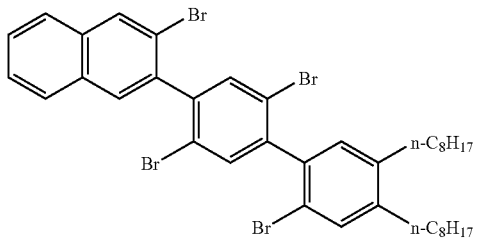
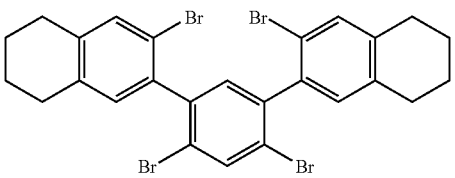
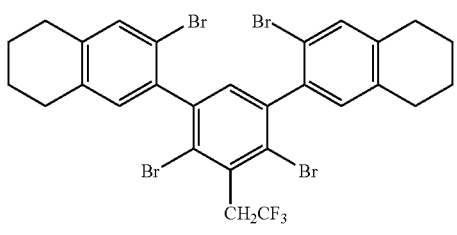
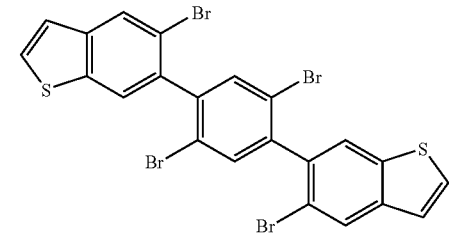
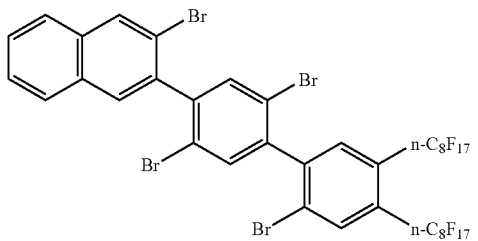
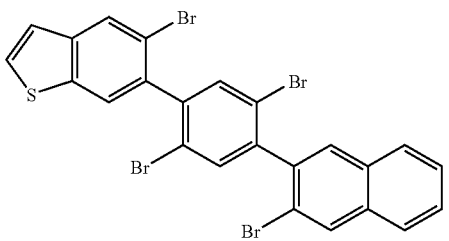
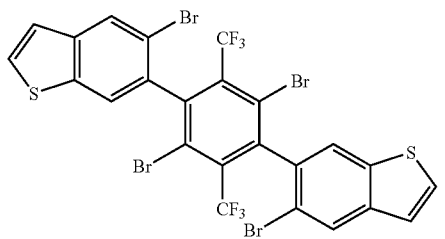
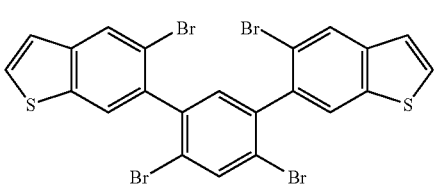

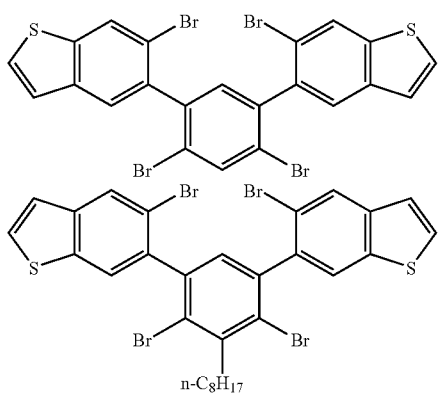
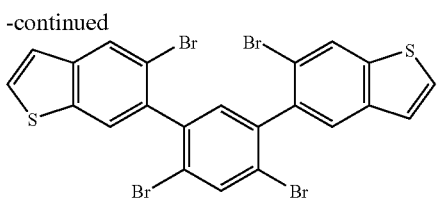

(Process for Producing Tetrahaloterphenyl Derivative)

The following will describe the process for producing the tetrahaloterphenyl derivative represented by the formula (2) of the invention.

The tetrahaloterphenyl derivative represented by the formula (2) of the invention can be produced by cross-coupling a tetrahaloarene represented by the following formula (6) with a 2-haloaryl metal reagents represented by the following formula (7) and/or the following formula (8) in the presence of a palladium and/or nickel catalyst:

[ka 26]

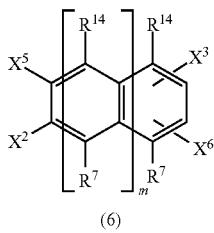

(6)

wherein the substituents $X^5$ and $X^6$ each represents a bromine atom, an iodine atoms or a chlorine atom; the substituents $R^7$, $R^{14}$, $X^2$, and $X^3$ and the symbol m represent the same meanings as the substituents and the symbol represented in the formula (2); provided that the designation of the formula (6) is the general term for the fact that the substituents $X^5$ and $X^6$ have at least one position selected from para-position and meta-position,

[ka 27]

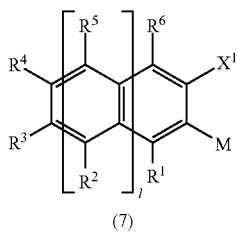

(7)

wherein M represents a halide, a hydroxide, an alkoxide, or an alkylated product of Mg, B, Zn, Sn, or Si; the substituents $R^1$ to $R^6$ and $X^1$ and the symbol l represent the same meanings as the substituents and the symbol represented in the formula (2),

[ka 28]

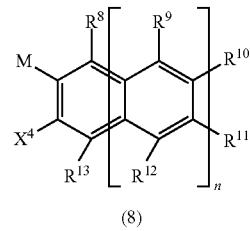

(8)

wherein M represents a halide, a hydroxide, an alkoxide, or an alkylated product of Mg, B, Zn, Sn, or Si; the substituents $R^8$ to $R^{13}$ and $X^4$ and the symbol n represent the same meanings as the substituents and the symbol represented in the formula (2).

The following will further describe the substituents of the formulae (6), (7), and (8) of the invention.

The substituents $X^5$ and $X^6$ of the formula (6) are a bromine atom or an iodine atom, more preferably an iodine atom.

The substituent M of the formulae (7) and (8) is a halide, a hydroxide, an alkoxide, or an alkylated product of Mg, B, Zn, Sn, or Si and is not particularly limited so far as it is a group which is eliminated by the above palladium and/or nickel catalyst and can be replaced by palladium and/or nickel. Examples thereof may include MgCl, MgBr, B(OH)$_2$, B(OMe)$_2$, a tetramethyldioxaboranyl group, ZnCl, ZnBr, ZnI, Sn(Bu-n)$_3$, and Si(Bu-n)$_3$ and preferred is B(OH)$_2$ or ZnCl.

Incidentally, the 2-haloaryl metal reagent represented by the formula (7) or (8) can be suitably prepared, for example, by performing a halogen/metal exchange reaction of an aryldihalogen substituted compound as a starting material thereof with a Grignard reagent such as isopropylmagnesium bromide or an organolithium reagent such as n-butyllithium, followed by reaction with zinc chloride, trimethoxyborane, or the like.

The catalyst for use in the cross-coupling reaction of the tetrahaloarene represented by the formula (6) with the 2-haloaryl metal reagent represented by the formula (7) and/or the formula (8) is not particularly limited so far as it is a palladium and/or nickel catalyst. For example, specific examples of the palladium catalyst may include tetrakis(triphenylphosphine)palladium, a tris(dibenzylideneacetone)dipalladium/triphenylphosphine mixture, dichlorobis(triphenylphosphine)palladium, bis(tri-tert-butylphosphine)palladium, diacetatobis(triphenylphosphine)palladium, dichloro(1,2-bis(diphenylphosphino) ethane)palladium, a palladium acetate/ triphenylphosphine mixture, a palladium acetate/tri-tert-butylphosphine mixture, a palladium acetate/2-(dicyclohexylphosphino)-1,1'-biphenyl mixture, dichloro(ethylenediamine)palladium, dichloro(N,N,N',N'-tetramethylethylenediamine)palladium, a dichloro(N,N,N',N'-tetramethylethylenediamine)palladium/triphenylphosphine mixture, and the like; and specific examples of the nickel catalyst may include dichlorobis(triphenylphosphine)nickel, dichloro(1,2-bis(diphenylphosphino)ethane)nickel, dichloro(ethylenediamine)nickel, dichloro(N,N,N',N'-tetramethylethylenediamine)nickel, a dichloro(N,N,N',N'-tetramethylethylenediamine)nickel/triphenylphosphine mixture, a bis(1,5-cyclooctadiene)nickel/triphenylphosphine mixture, and the like. Of these, a preferable catalyst is a zero valent palladium compound, and a particularly preferable catalyst is tetrakis(triphenylphosphine)palladium. Moreover, these catalysts may be used singly or as a mixture of two or more thereof.

The reaction is preferably carried out in a solvent. The solvent to be used is not particularly limited and examples thereof are tetrahydrofuran (hereinafter abbreviated as THF), diethyl ether, methyl tert-butyl ether, dioxane, ethylene glycol dimethyl ether, toluene, xylene, hexane, cyclohexane, ethanol, water, N,N-dimethylformamide, N-methylpyrrolidone, triethylamine, piperidine, pyrrolidine, diisopropylamine, and the like. Moreover, these solvents may be used singly or as a mixture of two or more thereof. For example, two or three component systems such as toluene/water, toluene/ethanol/water can be also used.

In this connection, a base may be present in the reaction system. In this case, the kind of the base is not particularly limited and examples thereof include inorganic bases such as sodium carbonate, sodium hydrogen carbonate, potassium carbonate, cesium carbonate, potassium phosphate, sodium phosphate, sodium tert-butoxide, and potassium fluoride, and organic bases such as triethylamine, trimethylamine, tributylamine, ethylenediamine, N,N,N',N'-tetramethylethylenediamine, diisopropylamine, and pyridine as suitable ones. The amount of the bases to be used is in the range of 0.5 to 10.0 equivalents, preferably 2.0 to 8.0 equivalents to the tetrahaloarene of the formula (6). Furthermore, in combination with these bases, a phase transfer catalyst may be also used. The kind of the phase transfer catalyst is not particularly limited and examples thereof may include trioctylmethylammonium chloride, tetrabutylammonium chloride, cetylpyridinium chloride, and the like as suitable ones. The amount of the phase transfer catalyst is in the range of 0.1 to 1.5 equivalents, preferably 0.2 to 0.8 equivalent to the tetrahaloarene of the formula (6).

Furthermore, a phosphine such as triphenylphosphine may be also present in the reaction system. The amount of the phosphine to be used is in the range of 0.9 to 8.0 equivalents, preferably 1.0 to 3.0 equivalents to the palladium and/or nickel catalyst.

In this connection, a copper compound may be present in the reaction system. In this case, the kind of the cooper compound is not particularly limited and examples thereof may include monovalent copper compounds such as copper(I) chloride, copper(I) bromide, copper(I) iodide, and copper(I) acetate; divalent copper compounds such as copper(II) chloride, copper(II) bromide, copper(II) iodide, copper(II) acetate, and copper(II) acetylacetonate. Preferred is a monovalent copper compound, particularly preferred is copper(I) iodide. The amount of the copper compound to be used is in the range of 0.3 to 10.0 equivalents, preferably 0.6 to 6.0 equivalents to the palladium and/or nickel catalyst.

Incidentally, in the process for producing the tetrahaloterphenyl derivative represented by the formula (2) of the invention, generally two kinds of tetrahaloterphenyl derivatives are formed. Namely, two kinds of position isomers, i.e., the tetrahaloterphenyl derivative represented by the formula (3) of a para-position isomer and the tetrahaloterphenyl derivative represented by the formula (4) of a meta-position isomer are formed. In the case where these different position isomers are formed as a mixture, both isomers can be easily separated by known methods utilizing difference in physical properties between them, such as column chromatographic purification and/or recrystallization purification.

Furthermore, in the production process of the invention, generally, a derivative where both ends of the ring structure of the derivative have different substitution patterns and a derivative where both ends of the ring structure of the derivative, as shown in formula (5), have the same substitution pattern are formed.

Also, in the case where these different substitution patterns are formed as a mixture, both derivatives can be easily separated by known methods utilizing difference in physical properties thereof, such as column chromatographic purification and/or recrystallization purification.

Furthermore, in the process of the inventions it is also possible to produce only a tetrahaloterphenyl derivative having a specific substitution pattern wherein a plurality of substitution patterns are not mixed Moreover, it is also possible to produce only a tetrahaloterphenyl derivative of a specific position isomer wherein a plurality of position isomers are not mixed.

The following will describe the process for producing the tetrahaloterphenyl derivative represented by the formula (2) of the invention in detail. In the description, a process for producing only a tetrahaloterphenyl derivative represented by the formula (5) wherein both ends of the ring structure of the derivative are the same (hereinafter referred to as "production process I") and then a process for producing only a tetrahaloterphenyl derivative wherein both ends of the ring structure of the derivative are different (hereinafter referred to as "production process II") and additionally describe a process for production in the case where different substitution patterns are mixed in individual processes at the same time. Thereafter, a process for producing only a specific position isomer (hereinafter referred to as "production process III") will be described.

(Production Process I)

As starting materials, the tetrahaloarene represented by the formula (6) and the 2-haloaryl metal reagent represented by the formula (7) are used.

In the reaction, the amount of the catalyst to be used is in the range of 0.1 to 20% by mol, preferably 1 to 10% by mol relative to the tetrahaloarene represented by the formula (6). The 2-haloaryl metal reagent of the formula (7) can be used in the range of 1.6 to 3.2 equivalents, preferably 1.8 to 2.8 equivalents, more preferably 19 to 2.5 equivalents to the tetrahaloarene represented by the formula (6).

The temperature of the reaction is from 10 to 120° C., preferably from 30 to 100° C., more preferably from 40 to 90° C. The reaction can be suitably carried out in the range of 1 to 48 hours, preferably from 2 to 30 hours.

According to such a process, a tetrahaloterphenyl derivative where both ends of the ring structure of the derivative are the same can be obtained.

In the process, by additionally using the 2-haloaryl metal reagent represented by the formula (8) as a starting material, a tetrahaloterphenyl derivative wherein different substitution patterns are mixed can be produced.

(Production Process II)

As starting materials, the tetrahaloarene represented by the formula (6) and the 2-haloaryl metal reagent represented by the formula (7) and the 2-haloaryl metal reagent represented by the formula (8) are used.

First, the tetrahaloarene represented by the formula (6) and the 2-haloaryl metal reagent represented by the formula (7) are reacted in the presence of a palladium and/or nickel catalyst to synthesize a tetrahalobiphenyl derivative represented by the following formula (9) as an intermediate and the intermediate is isolated:

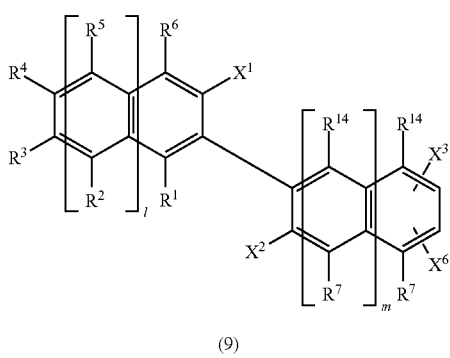

[ka 29]

(9)

wherein the substituents $R^1$ to $R^7$, $R^{14}$; $X^1$ to $X^3$ and $X^6$ represent the same meanings as the substituents represented in the formula (6) and the formula (7); also, l and m represent the same meanings as the symbols in the formula (6) and the formula (7) Thereafter, the synthesized tetrahalobiphenyl derivative represented by the formula (9) and the 2-haloaryl metal reagent represented by the formula (8) are reacted in the presence of a palladium and/or nickel catalyst.

In the reaction, the amount of the catalyst to be used is in the range of 0.1 to 20% by mol, preferably 1 to 10% by mol relative to the tetrahaloarene represented by the formula (6). The 2-haloaryl metal reagents of the formulae (7) and (8) can be used in the range of 0.5 to 1.5 equivalents, preferably 0.8 to 1.4 equivalents, more preferably 0.9 to 1.3 equivalents to the tetrahaloarene represented by the formula (6).

According to such a process, a tetrahaloterphenyl derivative wherein both ends of the ring structure of the derivative are different can be obtained.

In the reaction, by adding the 2-haloaryl metal reagent represented by the formula (8) to continue the reaction without isolation of the tetrahalobiphenyl derivative represented by the formula (9), a tetrahaloterphenyl derivative wherein different substitution patterns are mixed can be also produced.

(Production Process III)

The following will describe a process for producing only a tetrahaloterphenyl derivative of a para-position isomer represented by the formula (3) or only a tetrahaloterphenyl derivative of a meta-position isomer represented by the formula (4).

The position where a carbon-carbon bond is formed by a cross-coupling reaction of the tetrahaloarene represented by the formula (6) with the 2-haloaryl metal reagent(s) represented by the formula (7) and/or (8) can be controlled by the kind of the halogen.

Namely, since the reactivity of iodine is highest and the reactivity lowers in the order of bromine to chlorine, the position to be reacted can be arbitrarily determined by utilizing the reactivity depending on the kind of these halogens.

Therefore, the production of only the tetrahaloterphenyl derivative represented by the formula (3) can be achieved by arranging $X^5$ and $X^6$ of the formula (6) as iodine atoms in a para-position and $X^2$ and $X^3$ as bromine atom(s) and/or chlorine atom(s). On the other hand, the production of only the tetrahaloterphenyl derivative represented by the formula (4) can be achieved by arranging $X^5$ and $X^6$ of the formula (6) as iodine atoms is in a meta-position and $X^2$ and $X^3$ as bromine atom(s) and/or chlorine atom(s). In this connection, the process for producing only a specific position isomer can be applied to the process for producing a tetrahaloterphenyl derivative having a substitution pattern represented by the formula (5).

The thus obtained tetrahaloterphenyl derivative represented by the formula (2) of the invention can be further purified. The method for purification is not particularly limited and methods by column chromatography, recrystallization, or sublimation may be mentioned.

In the tetrahaloterphenyl derivative represented by the formula (2) of the invention, in the case of producing the tetrahaloterphenyl derivative represented by the formula (2) wherein the substituents $R^3$, $R^4$, $R^{10}$, and $R^{11}$ are the same or different and each is a group selected from the group consisting of an aryl group having 4 to 30 carbon atoms, an alkynyl group having 2 to 20 carbon atoms, an alkenyl group having 2 to 30 carbon atoms, an alkyl group having 1 to 20 carbon atoms or a halogenated alkyl group having 1 to 20 carbon atoms, and a diarylamino group having 8 to 30 carbon atoms, the derivative can be produced by setting the substituents $R^3$ and $R^4$ in the 2-haloaryl metal reagent represented by the formula (7) and the substituents $R^{10}$ and $R^{11}$ in the 2-haloaryl metal reagent represented by the formula (8) to the groups selected from the above group, respectively.

(Production of 2-Haloaryl Metal Reagent)

The 2-haloaryl metal reagents represented by the formulae (7) and (8) can be prepared by subjecting an aryldihalogen substituted compound represented by the following formula (10) as a starting material thereof to a halogen/metal exchange reaction with a Grignard reagent such as isopropylmagnesium bromide or an organolithium reagent such as n-butyllithium, followed by a reaction with zinc chloride, trimethoxyborane, or the like. In this connection, for the halogen/metal exchange reaction with an organolithium reagent, a lithiation method of a halogen described in Journal of Chemical Research Synopsis, 1981, p. 185 can be also used, for example.

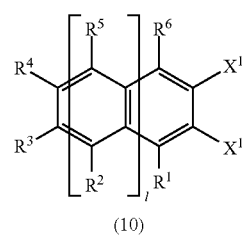

[ka 30]

(10)

wherein the substituents $X^1$, $R^1$ to $R^6$ and the symbol l represent the same meanings as the substituents $X^1$, $R^1$ to $R^6$ and the symbol l represented in the formula (7) or the same meanings as the substituents $X^4$, $R^8$ to $R^{13}$ and the symbol n represented in the formula (8).

In this connection, in order to set the substituents $R^3$ and $R^4$ in the 2-haloaryl metal reagent represented by the formula (7) and the substituents $R^{10}$ and $R^{11}$ in the 2-haloaryl metal reagent represented by the formula (8) to the groups selected from the above group, respectively, each reagent can be produced by setting the substituents $R^3$ and $R^4$ in the formula (10) to the groups selected from the above group, respectively.

(Process for Producing Aryldihalogen Substituted Compound)

The following will describe the process for producing the aryldihalogen substituted compound represented by the formula (10).

The aryldihalogen substituted compound represented by the formula (10) can be also produced by cross-coupling the tetrahaloarene represented by the following formula (11) and the reacting agent represented by the following formula (12) in the presence of a palladium and/or nickel catalyst.

[ka 31]

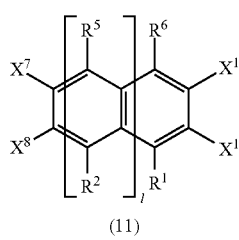

(11)

wherein the substituent $X^7$ represents an iodine atom or a bromine atom, the substituent $X^8$ represents an iodine atom, a bromine atom, or a hydrogen atom, the substituents $X^1$, $R^1$, $R^2$, $R^5$, and $R^6$, and the symbol l represent the same meanings as the substituents and the symbol represented by the formula (10).

In this connection, the substituents $X^7$ and $X^8$ each is preferably an iodine atom.

$$AN \qquad (12)$$

wherein A represents a hydrogen atom, a fluorine atom, a chlorine atom, an aryl group having 4 to 30 carbon atoms, an alkynyl group having 2 to 20 carbon atoms, an alkenyl group having 2 to 30 carbon atoms, an alkyl group having 1 to 20 carbon atoms or a halogenated alkyl group having 1 to 20 carbon atoms, or a diarylamino group having 8 to 30 carbon atoms; and N represents a hydrogen atom, an alkali metal of Li, Na, or K, a halide, a hydroxide, an alkoxide, or an alkylated product of Mg, B, Zn, Sn, or Si.

In this connection, by selecting A of the formula (12), desired substituents can be introduced into the substituents $X^7$ and $X^8$ of the tetrahaloarene represented by the formula (11) to obtain the aryldihalogen substituted compound represented by the formula (10) having desired substituents.

The substituent N of the formula (12) is a hydrogen atom, an alkali metal of Li, Na, or K, a halide, a hydroxide, an alkoxide, or an alkylated product of Mg, B, Zn, Sn, or Si and is not particularly limited so far as it is a group which reacts with the above palladium and/or nickel catalyst and is capable of being replaced by palladium and/or nickel or forms a hydrogen halide during the reaction. Examples thereof may include MgCl, MgBr, B(OH)$_2$, B(OMe)$_2$, a tetramethyldioxaboranyl group, ZnCl, ZnBr, ZnI, Sn(Bu-n)$_3$, and Si(Bu-n)$_3$ and preferred is B(OH)$_2$ or ZnCl.

Incidentally, the reacting agent represented by the formula (12) can be suitably prepared, for example, by performing a halogen/metal exchange reaction of an arylhalogen substituted compound as a starting material thereof with a Grignard reagent such as isopropylmagnesium bromide or an organolithium reagent such as n-butyllithium, followed by reaction with zinc chloride, trimethoxyborane, or the like. Moreover, the reaction agent represented by the formula (12) may be used singly or as a mixture of two or more thereof.

The catalyst for use in the cross-coupling reaction of the tetrahaloarene represented by the formula (11) with the reacting agent represented by the formula (12) is not particularly limited so far as it is a palladium and/or nickel catalyst. For example, the palladium and/or nickel catalysts used in the tetrahaloterphenyl derivative represented by the formula (2) may be mentioned. Of these, a preferable catalyst is a zero valent palladium compound, and a particularly preferable catalyst is tetrakis(triphenylphosphine)palladium.

In the cross-coupling reaction, the amount of the catalyst to be used is in the range of 0.1 to 20% by mot relative to the tetrahaloarene represented by the formula (11). The reacting agent of the formula (12) can be used in the range of 1.4 to 3.5 equivalents, preferably 1.6 to 3.0 equivalents, more preferably 1.8 to 2.8 equivalents to the tetrahaloarene represented by the formula (11) in the case where one kind of the reacting agent of the formula (12) is used and, in the case where two kinds of the reacting agent of the formula (12) are used, each reagent can be used in the range of 0.6 to 1.8 equivalents, preferably 0.7 to 1.5 equivalents, more preferably 0.8 to 1.4 equivalents to the tetrahaloarene represented by the formula (11).

In this connection, in the cross-coupling reaction, in the case where two kinds of the reacting agent of the formula (12) are used, the two kinds of the reacting agent can be present at the start of the reaction or the first reacting agent and the second reacting agent can be added at an interval.

The reaction is preferably carried out in a solvent. As specific examples, the solvents used in the tetrahaloterphenyl derivative represented by the formula (2) may be mentioned and these solvents may be used singly or as a mixture of two or more thereof. For example, two or three component systems such as toluene/water, toluene/ethanol/water can be also used.

In this connection, a base may be present in the reaction system. In this case, the kind of the base is not particularly limited and the bases used in the tetrahaloterphenyl derivative represented by the formula (2) may be mentioned. The amount of the bases to be used is in the range of 1.5 to 10.0 equivalents, preferably 2.0 to 8.0 equivalents to the tetrahaloarene of the formula (11). Furthermore, in combination with these bases, a phase transfer catalyst may be also used. The kind of the phase transfer catalyst is not particularly limited and the phase transfer catalysts used in the tetrahaloterphenyl derivative represented by the formula (2) may be mentioned. The amount of the phase transfer catalyst is in the range of 0.1 to 1.5 equivalents, preferably 0.2 to 0.8 equivalents to the tetrahaloarene of the formula (11).

In addition, a phosphine such as triphenylphosphine may be also present in the reaction system. The amount of the phosphine to be used is in the range of 0.9 to 8.0 equivalents, preferably 1.0 to 3.0 equivalents to the palladium and/or nickel catalyst.

In this connection, a copper compound may be present in the reaction system. In this case, the kind of the cooper compound is not particularly limited and examples thereof may include monovalent copper compounds such as copper(I) chloride, copper(I) bromide, copper(I) iodide, and copper(I) acetate; divalent copper compounds such as copper(II) chloride, copper(II) bromide, copper(II) iodide, copper(II) acetate, and copper(II) acetylacetonate. Preferred is a monovalent copper compound, particularly preferred is copper(I) iodide. The amount of the copper compound to be used is in the range of 0.3 to 10.0 equivalents, preferably 0.6 to 6.0 equivalents to the palladium and/or nickel catalyst.

The temperature of the reaction is from 10 to 120° C., preferably from 30 to 100° C. The reaction can be suitably carried out in the range of 1 to 72 hours.

The position where a bond is formed by the cross-coupling reaction of the tetrahaloarene represented by the formula (11) with the reacting agent represented by the formula (12) can be controlled by the kind of the halogen.

Namely, since the reactivity of iodine is highest and the reactivity lowers in the order of bromine to chlorine, the position to be reacted can be arbitrarily determined by utilizing the reactivity in the kind of these halogens.

Therefore, the synthesis of the aryldihalogen substituted compound represented by the formula (10) can be achieved by arranging $X^7$ and/or $X^8$ of the formula (11) as iodine atoms and $X^1$ as a bromine atom and/or a chlorine atom.

The production of the aryldihalogen substituted compound represented by the formula (10) is preferably carried out in an inert atmosphere, such as nitrogen or argon.

In this connection, among the aryldihalogen substituted compounds represented by the formula (10), compounds wherein the substituents $R^3$ and $R^4$ are combined to form a ring can be also produced by the method described in "Synthesis", 1988, pp. 628-631, for example.

The aryldihalogen substituted compound represented by the formula (10) can be further purified. The method for purification is not particularly limited and methods by column chromatography, recrystallization, or sublimation may be mentioned.

(Oxidation-Resistant Organic Semiconductor Material)

The following will describe the oxidation-resistant organic semiconductor material containing the terphenylene derivative represented by the formula (1) of the invention. The oxidation-resistant organic semiconductor material is excellent in solubility in a solvent and oxidation resistance and has a suitable coating ability. The oxidation-resistant organic semiconductor material can be produced by dissolving the terphenylene derivative represented by the formula (1) of the invention in a solvent.

The solvent for use in dissolution of the terphenylene derivative represented by the formula (1) of the invention is preferably a halogen-based solvent containing a halogen such as chlorine, e.g., o-dichlorobenzene, chlorobenzene, 1,2-dichloroethane, 1,1,2,2-tetrachloroethane, or chloroform; an ether-based solvent containing one or two oxygen atoms, e.g., THF or dioxane; a hydrocarbon-based solvent of an aromatic compound, e.g., toluene or xylene; an ester-based solvent, e.g., ethyl acetate or γ-butyrolactone; an amide-based solvent, e.g., N,N-dimethylformamide or N-methylpyrrolidone; and the like. These solvents may be used singly or as a mixture of two or more thereof. Of these, the solvent is preferably o-dichlorobenzene or toluene.

By mixing the solvent mentioned in the above and the terphenylene derivative represented by the formula (1) and stirring the mixture, the oxidation-resistant organic semiconductor material containing the terphenylene derivative represented by the formula (1) can be prepared. In this case, the temperature is from 10 to 200° C., preferably from 20° C. to 190° C. When the temperature is 10° C. or higher, the concentration becomes suitable and a good thin film can be obtained. When the temperature is 200° C. or lower, a solvent which can be used under normal pressure can be adopted and is economically preferred at the same time. The concentration of the resulting solution can be varied by the solvent and temperature but is from 0.01 to 10.0% by weight. The preparation of the solution can be carried out even in the air but the solution is preferably prepared under an inert atmosphere, such as nitrogen or argon.

The evaluation of the oxidation resistance of the oxidation-resistant organic semiconductor material containing the terphenylene derivative represented by the formula (1) of the invention can be carried out by the method of bringing the solution into contact with air for a predetermined period of time. First, the solvent to be used is degassed beforehand to remove dissolved oxygen. The contact period with air is suitably from 0.5 minute to 3 hours although it depends on the temperature. The proceeding of oxidation can be confirmed by observing color change of the solution and detecting oxidation products by gas chromatography and gas chromatography-mass spectrometry (GCMS).

Since the terphenylene derivative represented by the formula (1) itself to be used has an appropriate cohesiveness, the oxidation-resistant organic semiconductor material containing the terphenylene derivative represented by the formula (1) of the invention can be dissolved in a solvent at relatively low temperature and is suitably applied to the production of the organic thin film by a coating process since the derivative has oxidation resistance. Namely, since air is not necessarily strictly removed from the atmosphere, the coating step can be simplified. The coating can be carried out even in the air but is preferably carried out under a nitrogen atmosphere when drying of the solvent is considered. In order to obtain suitable coating ability, the viscosity of the oxidation-resistant organic semiconductor material containing the terphenylene derivative represented by the formula (1) of the invention is preferably in the range of 0.005 to 20 poise.

(Organic Thin Film)

The following will describe the organic thin film wherein the oxidation-resistant organic semiconductor material containing the terphenylene derivative represented by the formula (1) of the invention is used. Such an organic thin film can be produced by recrystallization of the above oxidation-resistant organic semiconductor material solution or coating a substrate therewith.

The thin film by recrystallization can be formed by cooling the oxidation-resistant organic semiconductor material solution. The atmosphere at the time when the organic thin film is produced is an inert gas such as nitrogen, argon or air but the production is preferably carried out under an inert gas such as nitrogen or argon. The concentration of the terphenylene derivative represented by the formula (1) of the invention in the solution is not particularly limited and is, for example, from 0.01 to 10.0% by weight. The cooling can be suitably carried out by cooling the solution from a temperature range of 60 to 200° C. to a temperature range of −20° to 60° C., preferably −10° C. to 40° C. Also, thus produced crystalline organic thin film can be attached on an appropriate substrate, i.e., can be produced on the substrate by lamination or the like. The film thickness of the thin film obtained by recrystallization is not particularly limited but is preferably from 50 nm to 2 mm, particularly preferably from 1 μm to 500 μm.

The production of the thin film by coating a substrate can be carried out by applying the oxidation-resistant organic semiconductor material solution on the substrate and subsequently vaporizing the solvent by heating, air-stream, natural drying, and the like method. The concentration of the terphenylene derivative represented by the formula (1) in the solution is not particularly limited but is preferably from 0.01 to 10.0% by weight, for example. The coating temperature is not particularly limited but the coating can be suitably carried out between 20° C. and 200° C. A specific method for coating is not particularly limited and known methods such as spin coating, cast coating, dip coating, and the like can be used. Furthermore, printing technologies such as screen printing, inkjet printing, gravure printing can be also used for the production The material for the substrate to be used is not particularly limited and various crystalline or non-crystalline materials can be used. Moreover, the substrate may be an insulating or dielectric material. As specific examples, there may be suitably used substrates of plastics such as polyethylene terephthalate, polymethyl methacrylate, polyethylene, polypropylene, polystyrene, cyclic polyolefins, polyimides, polycarbonates, polyvinylphenol, and polyvinyl alcohol; substrates of inorganic materials such as glass, quarts, aluminum oxide, silicon, silicon oxide, tantalum dioxide, tantalum pentoxide, and indium tin oxide; substrates of metals such as gold, copper, chromium, and titanium. Moreover, there can be used substrates whose surface is modified with a silane such as octadecyltrichlorosilane or octadecyltrimethoxysilane, or a silylamine such as hexamethyldisilazane. The solvent after coating can be removed for drying under normal pressure or reduced pressure. Alternatively, the solvent may be removed for drying by heating or nitrogen stream. Furthermore, by regulating the vaporization rate of the solvent, crystal growth of the terphenylene derivative represented by the formula (1) of the invention can be controlled. The film thickness of the thin film obtained by coating the substrate is not particularly limited but is preferably from 1 nm to 100 μm, particularly preferably from 10 nm to 20 μm.

The terphenylene derivative represented by the formula (1) of the invention has a molecular structure with a high plane rigidity, so that it is expectable to provide an excellent semiconductor properties. Moreover, the terphenylene derivative dissolves in a polar solvent such as dichlorobenzene and is not easily oxidized with air even in a solution state. Therefore, a semiconductor thin film can be easily formed by a coating process. Thus, the terphenylene derivative represented by the formula (1) of the invention can be utilized for an organic semiconductor active phase of transistor for electronic papers, organic EL displays, liquid crystal displays, IC tags, or the like and also as an organic EL display material, an organic semiconductor laser material, an organic thin film solar battery material, photonic crystalline material, or the like.

The following will describe the invention further in detail with reference to Examples but the invention is not limited to these Examples.

For identification of products, $^1$H NMR spectra and mass spectra were used. The $^1$H NMR spectra were measured using JEOL GSX-270WB (270 MHz) manufactured by JEOL Ltd. and mass spectra were measured using JEOL JMS-700 manufactured by JEOL Ltd. by an electron impact (EI) method (70 eV) or a FAB method (6 keV, xenon gas, matrix (dithiothreitol:dithioerythritol=3:1)) with direct introduction of a sample.

For confirmation of the progress of a reaction, analyses on gas chromatography and gas chromatography-mass spectroscopy (GCMS) were employed.
Analysis on Gas Chromatography
  Apparatus: Shimadzu GC14B
  Column: DB-1 manufactured by J & W Scientific Co. Ltd., 30 m
Analysis on Gas Chromatography-Mass Spectroscopy
  Apparatus: Perkin-Elmer autosystem XL (MS portion: turbo mass gold)
  Column: DB-1 manufactured by 3 & W Scientific Co. Ltd., 30 m
As the solvents for reactions, commercially available dehydrated solvents were used as they were.

Synthetic Example 1

Synthesis of 1,4-dibromo-2,5-diiodobenzene 1,4-Dibromo-2,5-diiodobenzene was synthesized with reference to the method described in Journal of American Chemical Society, 1997, vol. 119, pp. 4578-4593.

To a 1 L three-necked flask fitted with a mechanical stirrer were added 16.7 g (73.0 mmol) of periodic acid and 525 ml of sulfuric acid. After periodic acid was dissolved, 36.4 g (219 mmol) of potassium iodide was added portionwise. The content was cooled to a temperature of −30° C. and 34.5 g (146 mmol) of 1,4-dibromobenzene was added over a period of 5 minutes. The resulting mixture was stirred at −30 to −20° C. for 36 hours. After the reaction mixture was poured into ice (2 kg), the whole was filtrated and a solid was taken out. The solid was dissolved in chloroform, the solution was washed with a 5% aqueous sodium hydroxide solution and water, and the organic phase was dried over anhydrous magnesium sulfate. After concentration under reduced pressure, the residue was recrystallized from chloroform to obtain white crystals of 1,4-dibromo-2,5-diiodobenzene (36.0 g, yield 50%).
$^1$H NMR spectrum thereof was coincident with that in literature.
$^1$H NMR (CDCl$_3$, 21° C.): δ=8.02 (s, 2H).
The following shows the structural formula of the resulting 1,4-dibromo-2,5-diiodobenzene.

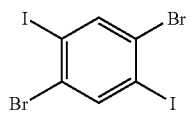

[ka 32]

Synthetic Example 2

Synthesis of 2-bromo-3-iodonaphthalene

2-Bromo-3-iodonaphthalene was synthesized with reference to the method described in Synthetic Communications, 2003, vol. 33, pp. 2751-2756. A starting material, 2-bromo-bis(hexachlorocyclopentadiene)naphthalene was purchased from Sigma-Aldrich and used as it was.

To a 500 ml three-necked flask reaction vessel were added under a nitrogen atmosphere 200 ml of methanesulfonic acid and 1.31 g (5.74 mmol) of orthoperiodic acid. After 30 minutes of stirring, 4.36 g (17.2 mmol) of iodine was added thereto. After the mixture was stirred for 2 hours, 30.1 g (40.0 mmol) of 2-bromo-bis(hexachlorocyclopentadiene)naphthalene was added portionwise. The mixture was stirred at 30° C. for 3 days. The reaction mixture was poured into ice water and the resulting solid was filtrated. The solid was further washed with water and dried under reduced pressure to obtain a white powder of 2-bromo-3-iodo-bis(hexachlorocyclopentadiene) naphthalene (34.8 g, yield 99%).

To a terminal end of a glass sublimation tube was added 8.05 g (9.16 mmol) of 2-bromo-3-iodo-bis(hexachlorocyclopentadiene)naphthalene obtained in the above. The terminal end was heated to 210° C. and reduced to 1.5 Pa. The generated 2-bromo-3-iodonaphthalene was attached to the glass tube at a reduced pressure side and hexachlorocyclopentadiene was collected at the bottom of the reduced pressure side. After 1 hour, the sublimation operation was stopped, the attached matter on the glass 11 tube was taken out, and then the same operation was again repeated. After 1 hour of the sublimation operation, 2-bromo-3-iodonaphthalene was obtained (2.29 g, yield 75%).

$^1$H NMR spectrum thereof was coincident with that in literature.

$^1$H NMR (CDCl$_3$, 21° C.): δ=8.41 (s, 1H), 8.14 (s, 1H), 7.75-7.65 (m, 2H), 7.54-7.45 (m, 2H).

The following shows the structural formula of the resulting 2-bromo-3-iodonaphthalene.

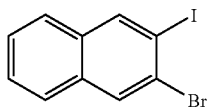

[ka 33]

Example 1

Synthesis of 2,2',4',2''-tetrabromo-1,1',5',1''-terphenyl and 2,2',5',2''-tetrabromo-1,1',4',1''-terphenyl To a 100 ml Schlenk reaction vessel were added under a nitrogen atmosphere 1.70 g (4.31 mmol) of 1,2,4,5-tetrabromobenzene (manufactured by Tokyo Chemical Industry Co. Ltd.), 253 mg (0.218 mmol) of tetrakis(triphenylphosphine) palladium (manufactured by Tokyo Chemical Industry Co. Ltd.), and 1.99 g (9.90 mmol) of 2-bromophenylboronic acid (manufactured by Sigma-Aldrich). Further, 34 ml of toluene, 9 ml of ethanol, and an aqueous solution composed of 2.75 g (25.9 mmol) of sodium carbonate and 10 ml of water were added thereto. The whole was immersed in an oil bath at 85° C. and stirred for 8 hours. After cooling to room temperature, a saturated aqueous sodium chloride solution was added and phase separation was conducted. Then, 1 ml of tert-butyl hydroperoxide (content 70% by weight) was added to the resulting organic phase at room temperature, followed by 2 hours of stirring. A saturated aqueous sodium chloride solution was added, phase separation was conducted, and the organic phase was concentrated under reduced pressure. The residue was purified by silica gel column chromatography.

First, an ingredient containing 2,2',4',2''-tetrabromo-1,1',5',1''-terphenyl as a main part was eluted with hexane/toluene=1/1 and the elute was referred to as Fraction 1. Then, an ingredient containing 2,2',5',2''-tetrabromo-1,1',4',1''-terphenyl as a main part was eluted with toluene alone and the elute was referred to as Fraction 2. Each fraction was concentrated under reduced pressure. As a result, whole Fraction 2 (0.32 g) formed a solid. On the other hand, Fraction 1 (1.97 g) partially formed a solid, so that it was separated into an oil portion and a solid portion. The oil portion was further purified by silica gel column chromatography (solvent: hexane). As a result, a colorless transparent oil was obtained. The colorless transparent oil was solidified with the passage of time.

Based on $^1$H NMR spectrum, the colorless transparent oil was found to be 2,2',4',2''-tetrabromo-1,1',5',1''-terphenyl (1.37 g, yield 58%).

$^1$H NMR (CDCl$_3$, 21° C.): δ=7.99 (d, J=1.9 Hz, 1H), 7.68 (dd, J=7.8 Hz, 1.7 Hz, 2H), 7.42-7.19 (m, 6H), 7.15 (s, 1H).

MS m/z: 546 (M$^+$, 75%), 466 (M$^+$-Br, 41), 386 (M$^+$-2Br, 51), 226 (M$^+$-4Br, 100).

The following shows the structural formula of the resulting 2,2',4',2''-tetrabromo-1,1',5',1''-terphenyl.

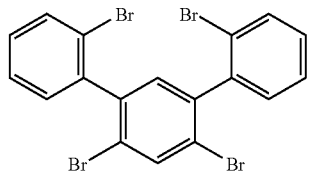

[ka 34]

On the other hand, Fraction 2 and the above solid portion separated from Fraction 1 were combined and recrystallized from toluene. White needle-like crystals were obtained.

Based on $^1$H NMR spectrum, the white needle-like crystals were found to be 2,2',5',2''-tetrabromo-1,1',4',1''-terphenyl (0.47 g, yield 20%).

Melting point: 230-231° C.

$^1$H NMR (CDCl$_3$, 21° C.): δ=7.70 (d, J=8.0 Hz, 2H), 7.55 (d, J=1.5 Hz, 2H), 7.45-7.23 (m, 6H).

MS m/z: 546 (M$^+$, 92%), 466 (M$^+$-Br, 45), 386 (M$^+$-2Br, 53), 226 (M$^+$-4Br, 100).

The following shows the structural formula of the resulting 2,2',5',2''-tetrabromo-1,1',4',1''-terphenyl.

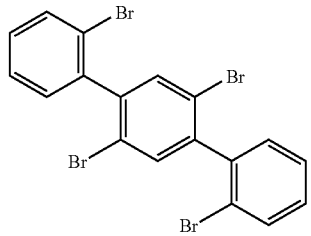

[ka 35]

Thus, it was evidenced that terphenyls could be synthesized by the above process.

Example 2

Synthesis of 2,2',5',2''-tetrabromo-1,1,4',1''-terphenyl

To a 100 ml Schlenk reaction vessel were added under a nitrogen atmosphere 4.39 g (9.00 mmol) of 1,4-dibromo-2,5-diiodobenzene synthesized in Synthetic Example 1, 974 mg (0.84 mmol) of tetrakis(triphenylphosphine) palladium (manufactured by Tokyo Chemical Industry Co. Ltd.), and 4.16 g (20.7 mmol) of 2-bromophenylboronic acid (manufactured by Sigma-Aldrich). Further, 72 ml of toluene, 18 ml of ethanol, and an aqueous solution composed of 5.72 g (54.0 mmol) of sodium carbonate and 22 ml of water were added. The whole was immersed in an oil bath at 85° C. and stirred for 15 hours. After cooling to room temperature, dichloromethane and a saturated aqueous sodium chloride solution were added and phase separation was conducted. The organic phase was concentrated under reduced pressure. The residue was recrystallized from toluene. White needle-like crystals of 2,2',5',2''-tetrabromo-1,1',4',1''-terphenyl were obtained (4.18 g, yield 85%) $^1$H NMR spectrum thereof was coincident with that of the ingredient obtained by purification through toluene recrystallization from Fraction 2 in Example 1.

Referential Example 1

Synthesis of Terphenylene

To a 100 ml Schlenk reaction vessel were added under a nitrogen atmosphere 269 mg (0.492 mmol) of 2,2',5',2''-tetrabromo-1,1',4',1"-terphenyl synthesized in Example 2 and 23 ml of THF. The solution was cooled to −80° C. and 5.0 ml (4.9 mmol) of a cyclohexane solution of sec-butyllithium (manufactured by Kanto Chemical Co., Ltd., 0.98M) was added dropwise. The color of the solution changed from light yellow to true green. After 20 minutes of stirring, 828 mg (6.2 mmol) of copper(II) chloride (manufactured by Wake Pure Chemical Industries, Ltd.) was charged at once at −75° C. and the temperature was raised to room temperature over a period of overnight. A saturated aqueous sodium chloride solution and toluene were added, then phase separation was conducted, and the organic phase was washed with a saturated aqueous sodium chloride solution. After concentration under reduced pressure, hexane was added to the resulting residue and, after stirring, the whole was allowed to stand. The supernatant was removed and the residue was dried under reduced pressure. The residue was recrystallized from toluene to obtain red plate-like crystals of terphenylene (24 mg, yield 22%). $^1$H NMR spectrum (deutrated benzene, 30° C.): δ=6.46 (AA', J=4.8 Hz, 2.9 Hz, 4H), 6.20 (BB', J=4.6 Hz, 2.9 Hz, 4H), 5.93 (s, 2H).

The following shows the structural formula of the resulting terphenylene.

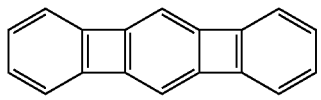

[ka 36]

Thus, it was evidenced that terphenylene could be synthesized by the above process.

Example 3

Synthesis of mixture of 2,2',4',2"-tetrabromo-1,1',5',1"-terphenyl and 2,2',5',2"-tetrabromo-1,1',4',1"-terphenyl To a 100 ml Schlenk reaction vessel were added under a nitrogen atmosphere 1.70 g (4.31 mmol) of 1,2,4,5-tetrabromobenzene (manufactured by Tokyo Chemical Industry Co. Ltd.), 253 mg (0.218 mmol) of tetrakis(triphenylphosphine)palladium (manufactured by Tokyo Chemical Industry Co. Ltd.), and 1.99 g (9.90 mmol) of 2-bromophenylboronic acid (manufactured by Sigma-Aldrich). Further, 34 ml of toluene, 9 ml of ethanol, and an aqueous solution composed of 2.75 g (25.9 mmol) of sodium carbonate and 10 ml of water were added. The whole was immersed in an oil bath at 85° C. and stirred for 8 hours. After cooling to room temperature, a saturated aqueous sodium chloride solution was added and phase separation was conducted. Then, 1 ml of tert-butyl hydroperoxide (content 70% by weight) was added to the resulting organic phase at room temperature, followed by 2 hours of stirring. A saturated aqueous sodium chloride solution was added, phase separation was conducted, and the organic phase was concentrated under reduced pressure. The residue was purified by silica gel column chromatography. Fractions eluted by toluene were concentrated under reduced pressure to obtain an oil (1.91 g, yield 81%), a part of which was solidified. Based on GC analysis, the partially solidified oil was found to be composed of two ingredients and the ratio was 8 (ingredient 1):2 (ingredient 2). Furthermore, based on GCMS analysis, the two ingredients were found to be 2,2',4',2"-tetrabromo-1,1',5',1"-terphenyl and 2,2',5',2"-tetrabromo-1,1',4',1"-terphenyl.

(GCMS Analysis)
(Ingredient 1)
MS m/z: 546 (M$^+$, 64%), 466 (M$^+$-Br, 38), 386 (M$^+$-2Br, 481), 226 (M$^+$-4Br, 100).
(Ingredient 2)
MS m/z: 546 (M$^+$, 85%), 466 (M$^+$-Br, 42), 386 (M$^+$-2Br, 54), 226 (M$^+$-4Br, 100).

Referential Example 2

Synthesis of Terphenylene

To a 100 ml Schlenk reaction vessel were added under a nitrogen atmosphere 192 mg (0.351 mmol) of a mixture of tetrabromoterphenyl having a ratio of 8:2 synthesized in Example 3 and 17 ml of THF. The solution was cooled to −80° C. and 3.6 ml (3.5 mmol) of a cyclohexane solution of sec-butyllithium (manufactured by Kanto Chemical Co., Ltd., 0.98M) was added dropwise. The color of the solution changed from light yellow to dark blue. After 20 minutes of stirring, 585 mg (4.3 mmol) of copper(II) chloride (manufactured by Wako Pure Chemical Industries, Ltd.) was charged at once at −75° C. and the temperature was raised to room temperature over a period of overnight. A saturated aqueous sodium chloride solution and toluene were added, then phase separation was conducted, and the organic phase was washed with a saturated aqueous sodium chloride solution. After concentration under reduced pressure, hexane was added to the resulting residue and, after stirring, the whole was allowed to stand. The supernatant was removed and the residue was dried under reduced pressure. The residue was recrystallized from toluene to obtain red plate-like crystals of terphenylene (11 mg, yield 14%). $^1$H NMR spectrum (deutrated benzene) was coincident with that obtained in Referential Example 1.

Thus, it was evidenced that terphenylene could be synthesized by the above process.

Example 4

Synthesis of 2,2',5',2"-tetrabromo-1,1',4',1"-dibenzoterphenyl

To a 100 ml Schlenk reaction vessel were added under a nitrogen atmosphere 2.03 g (6.10 mmol) of 2-bromo-3-iodonaphthalene synthesized in Synthetic Example 2 and 12 ml of THF. The solution was cooled to −65° C. and 9.9 ml (6.4 mmol) of a THF solution of isopropylmagnesium bromide (manufactured by Kanto Chemical Co., Ltd., 0.65M) was added dropwise. After 30 minutes of aging, 6.4 ml (6.4 mmol) of a diethyl ether solution of zinc chloride (manufactured by Sigma-Aldrich, 1.0M) was added dropwise at the temperature. After the temperature was gradually raised to room temperature, the formed white slurry liquid was concentrated under reduced pressure. To the obtained white solid were added 1.41 g (2.89 mmol) of 1,4-dibromo-2,5-diiodobenzene synthesized in Synthetic Example 1, 285 mg (0.247 mmol) of tetrakis(triphenylphosphine)palladium (manufactured by Tokyo Chemical Industry Co. Ltd.), and 31 ml of THF. After the reaction was carried out at 60° C. for 4 hours, the vessel was cooled with water and the reaction was stopped by adding 4 ml of 3N hydrochloric acid. The whole was concentrated under reduced pressure and the solvent was removed by distillation. The precipitated solid was washed with water until the filtrate showed neutral and further washed with chloroform and THF. The resulting crystals were dried under reduced pressure to obtain white crystals of 2,2',5',2'-tetrabromo-1,1',4',1"-dibenzoterphenyl (1.20 g, yield 64%).

Melting point by DSC measurement: 331° C.

$^1$H NMR (CDCl$_3$, 60° C.): δ=8.22 (s, 2H), 7.90-7.75 (m, 4H), 7.85 (s, 2H), 7.67 (s, 2H), 7.60-7.48 (m, 4H).

MS m/z: 646 (M$^+$, 64%), 566 (M$^+$-Br, 8), 486 (M$^+$-2Br, 34), 406 (M$^+$-3Br, 6), 326 (M$^+$-4Br, 92), 163 (M$^+$-4Br/2, 100).

The following shows the structural formula of the resulting 2,2',5',2''-tetrabromo-1,1',4',1''-dibenzoterphenyl.

[ka 37]

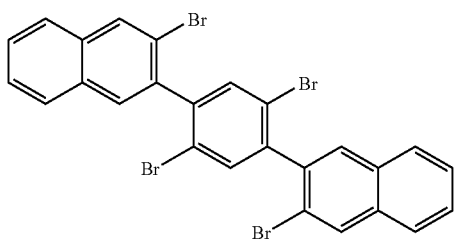

Example 5

Synthesis of Dibenzoterphenylene

To a 100 ml Schlenk reaction vessel were added under a nitrogen atmosphere 395 mg (0.611 mmol) of 2,2',5',2''-tetrabromo-1,1',4',1''-dibenzoterphenyl synthesized in Example 4 and 28 ml of THF. The suspension solution was cooled to −80° C. and 4.4 ml (4.3 mmol) of a cyclohexane solution of sec-butyllithium (manufactured by Kanto Chemical Co., Ltd., 0.98M) was added dropwise. The color of the solution changed from light yellow to true green. After 60 minutes of stirring, 740 mg (5.50 mmol) of copper(II) chloride (manufactured by Wako Pure Chemical Industries, Ltd.) was charged at once at −75° C. The reaction temperature was raised to room temperature over a period of overnight. After a saturated aqueous sodium chloride solution was added, the formed solid was filtrated. After the obtained solid was further washed with 3N hydrochloric acid, water, and THF, the solid was dried under reduced pressure to obtain a yellow-orange solid (85 mg). Furthermore, the solid was recrystallized from o-dichlorobenzene to obtain a plate-like solid having gold metallic luster (75 mg, yield 38%).

Analysis by DSC measurement (using tightly sealed vessel): exothermic heat derived from carbonization was observed at 500° C.

MS m/z: 326 (M$^+$, 100%), 163 (M$^+$/2, 25).

The following shows the structural formula of the resulting dibenzoterphenylene.

[ka 38]

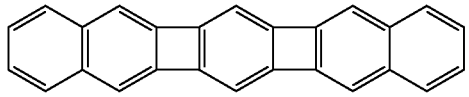

Example 6

Evaluation of Oxidation Resistance

Under a nitrogen atmosphere, 23.4 g of o-dichlorobenzene was added to a 100 ml Schlenk vessel and dissolved oxygen was removed by repeating three times a cycle composed of freezing (liquid nitrogen)-pressure reduction-replacement with nitrogen-melting. Thereto was added 7.5 mg of a solid of the dibenzoterphenylene having gold metallic luster obtained in Example 5. When the whole was heated and dissolved at 180° C., a bright yellow solution was obtained. Then, an upper stopcock of the Schlenk vessel was opened and air was introduced by bringing the vessel into contact with open air for 1 minute, followed by stirring at 180° C. However, no change in color was observed and no new peaks derived from oxidation appeared on gas chromatography and gas chromatography-mass spectroscopy (GCMS) analyses.

Example 7

Preparation of Organic Thin Film

Under a nitrogen atmosphere, 30 mg of the dibenzoterphenylene having gold metallic luster obtained in Example 5 was mixed with o-dichlorobenzene (95 g) and the whole was stirred at 180° C. for 1 hour to prepare a bright yellow solution of the dibenzoterphenylene. The solution was cooled from 180° C. to 20° C. over a period of 14 hours. The precipitated crystals were filtrated through a Buchner funnel and dried under reduced pressure to obtain a thin film of the dibenzoterphenylene (27 mg).

The obtained thin film is a thin film having a film thickness of 28 to 48 μm. As a result of measuring X-ray diffraction of the thin film, diffraction peaks of (00n) plane (n=1 to 7) having a plane-to-plane distance of 1.75 mm were obtained, so that it was found that the thin film was a crystalline thin film.

FIG. 1 shows an X-ray diffraction pattern.

Example 8

Preparation of Organic Thin Film

Under a nitrogen atmosphere, 8 mg of the dibenzoterphenylene having gold metallic luster obtained in Example 5 was mixed with o-dichlorobenzene (25 g) and the whole was stirred at 180° C. for 1 hour to prepare a bright yellow solution of the dibenzoterphenylene.

Under an air atmosphere, a concavely curved glass substrate is heated at 150° C. and the above solution was applied on the substrate using a dropper and dried under normal pressure to prepare a thin film having a film thickness of 380 nm. As a result of analyzing the ingredient of the thin film by gas chromatography, no peaks derived from compounds other than dibenzoterphenylene were present and thus no oxidation was observed. Therefore, it was found that a thin film of the dibenzoterphenylene could be prepared without oxidation even in the air.

Example 9

Synthesis of 4,5,4'',5''-tetrafluoro-2,2',5',2''-tetrabromo-1,1',4',1''-terphenyl To a 100 ml Schlenk reaction vessel were added under a nitrogen atmosphere 2.53 g (9.30 mmol) of 1,2-dibromo-4,5-difluorobenzene (manufactured by Wako Pure Chemical Industries, Ltd.) and 15 ml of THF. The solution was cooled to −40° C. and 15 ml (9.7 mmol) of a THF solution of isopropylmagnesium bromide (manufactured by Kanto Chemical Co., Ltd., 0.65M) was added dropwise. After 30 minutes of aging, 9.8 ml (9.8=mol) of a diethyl ether solution of zinc chloride (manufactured by Sigma-Aldrich, 1.0M) was added dropwise at the temperature, After the temperature was gradually raised to room temperature, the formed white slurry liquid was concentrated under reduced pressure. To the resulting white solid were added 2.15 g (4.41 mmol) of 1,4-dibromo-2,5-diiodobenzene synthesized in Synthetic Example 1, 408 mg (0.353 mmol) of tetrakis(triphenylphosphine)palladium (manufactured by Tokyo Chemical Industry Co. Ltd.), and 30 ml of THF. After the reaction was carried out at 60° C. for 6 hours, the vessel was cooled with water and the reaction was stopped by adding 3N hydrochloric acid (8 ml). After toluene and sodium chloride were added, phase separation was conducted, and the organic phase was washed with an aqueous sodium chloride solution. The organic phase was concentrated under reduced pressure and the solvent was removed by distillations. The obtained residue was dissolved in 10 ml of toluene and a 70% tert-butyl hydroperoxide solution (manufactured by Wake Pure Chemical Industries, Ltd.) (0.5 ml) was added, followed by 2 hours of stirring at room temperature. The solution was washed with water and the organic phase was concentrated under reduced pressure. The organic phase was dissolved in toluene:hexane=1:1 and was passed through a column packed with silica gel. The elute was concentrated under reduced pressure and the resulting solid was recrystallized using a mixed solvent of hexane:toluene=3:1 to obtain an objective white solid (1.48 g, yield 54%).

$^1$H NMR (CDCl$_3$, 21° C.) δ=7.58-7.45 (m, 2H), 7.53 (s, 2H), 7.23-7.09 (m, 2H).

MS m/z: 618 (M$^+$, 73%), 538 (M$^+$-Br, 32), 458 (M$^+$-2Br, 45), 378 (M$^+$-3Br, 4), 298 (M$^+$-4Br, 100).

The following shows the structure of the resulting objective compound.

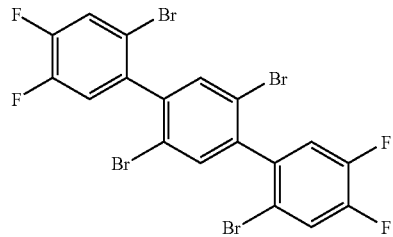

[ka 39]

Example 10

Synthesis of 3,4,5,6,3",4",5",6"-octafluoro-2,2',5', 2"tetrabromo-1,1',4',1"-terphenyl)

To a 100 ml Schlenk reaction vessel were added under a nitrogen atmosphere 446 mg (1.45 mmol) of 1,2-dibromotetrafluorobenzene (manufactured by Avocado) and 5 ml of THF. The solution was cooled to −40° C. and 2.2 ml (1.4 mmol) of a THF solution of isopropylmagnesium bromide (manufactured by Kanto Chemical Co. Ltd., 0.65M) was added dropwise. After 30 minutes of aging, 1.4 ml (1.4 mmol) of a diethyl ether solution of zinc chloride (manufactured by Sigma-Aldrich, 1.0M) was added dropwise at the temperature. After the temperature was gradually raised to room temperature, the mixture was concentrated under reduced pressure. To the resulting white solid were added 337 mg (0.69=mol) of 1,4-dibromo-2,5-diiodobenzene synthesized in Synthetic Example 1, 69 mg (0.060 mmol) of tetrakis (triphenylphosphine)palladium (manufactured by Tokyo Chemical Industry Co. Ltd.), and 5 ml of ethylene glycol dimethyl ether. After the reaction was carried out at 86° C. for 7 days, the vessel was cooled with water and the reaction was stopped by adding 3N hydrochloric acid (8 ml). After toluene and sodium chloride were added, phase separation was conducted, and the organic phase was washed with an aqueous sodium chloride solution. The organic phase was concentrated under reduced pressure and the solvent was removed by distillation. The resulting residue was dissolved in 10 ml of toluene and a 70% tert-butyl hydroperoxide solution (manufactured by Wake Pure Chemical Industries, Ltd.) (0.1 ml) was added, followed by 2 hours of stirring at room temperature. The solution was washed with water and the organic phase was concentrated under reduced pressure. The organic phase was dissolved in a mixed solvent of toluene:hexane=1:1 and was passed through a column packed with silica gel. The elute was concentrated under reduced pressure and the resulting solid was recrystallized using hexane to obtain an objective white solid (80 mg, yield 17%).

$^1$H NMR (CDCl$_3$, 21° C.): δ=7.57 (s, 2H).

MS m/z: 690 (M$^+$, 99%), 610 (M$^+$-Br, 34), 530 (M$^+$-2Br, 61), 450 (M$^+$-3Br, 3), 370 (M$^+$-4Br, 100).

The following shows the structure of the resulting objective compound.

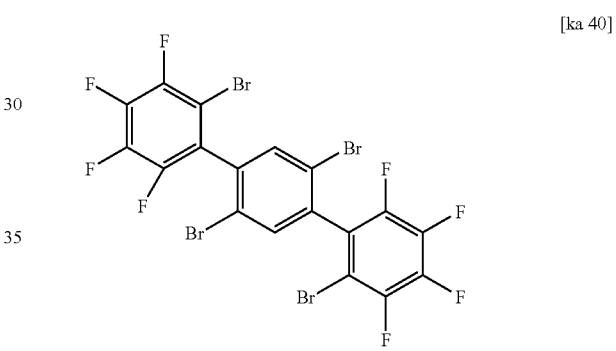

[ka 40]

Example 11

Synthesis of 2,3,7,8-tetrafluoroterphenylene

To a 100 ml Schlenk reaction vessel were added under a nitrogen atmosphere 506 mg (0.818 mmol) of 4,5,4",5"-tetrafluoro-2,2',5',2"-tetrabromo-1,1',4',1"-terphenyl synthesized in Example 9 and 28 ml of THF. The suspension solution was cooled to −80° C. and 59 ml (5.8 mmol) of a cyclohexane solution of sec-butyllithium (manufactured by Kanto Chemical Co., Ltd., 0.98M) was added dropwise. After 20 minutes of stirring, 981 mg (7.30 mmol) of copper(II) chloride (manufactured by Wako Pure Chemical Industries, Ltd.) was charged at once at −75° C. and the reaction temperature was gradually raised to −20° C. over a period of 7 hours. After a saturated aqueous sodium chloride solution and toluene were added, phase separation was conducted and the organic phase was washed with a saturated aqueous sodium chloride solution. After concentration under reduced pressure, hexane was added to the obtained residue and, after stirring, the whole was allowed to stand. The supernatant was removed and the residue was dried under reduced pressure. The residue was recrystallized from toluene to obtain red crystals of 2,3,7,8-tetrafluoroterphenylene (56 mg, yield 23%).

$^1$H NMR (CDCl$_3$, 21° C.): δ=6.33 (t, J=7.3 Hz, 4H), 6.14 (s, 2H).

MS m/z: 298 (M$^+$, 100%), 149 (M$^+$/2, 38).

The following shows the structure of the resulting objective compound.

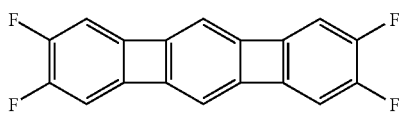

Example 12

Evaluation of Oxidation Resistance

Under a nitrogen atmosphere, 2.0 g of o-dichlorobenzene was added to a 20 ml Schlenk vessel and dissolved oxygen was removed by repeating three times a cycle composed of freezing (liquid nitrogen)-pressure reduction-replacement with nitrogen-melting. Thereto was added 4.5 mg of a red solid of 2,3,7,8-tetrafluoroterphenylene obtained in Example 11. When the whole was stirred at 22° C., a reddish orange solution was obtained. Then, an upper stopcock of the Schlenk vessel was opened and air was introduced by bringing the vessel into contact with open air for 1 minute, followed by stirring at 22° C. However, no change in color of the solution was observed and no new peaks derived from oxidation appeared on gas chromatography and gas chromatography-mass spectroscopy (GCMS) analyses.

Comparative Example 1

Evaluation of Oxidation Resistance

Oxidation resistance was evaluated using pentacene.

Under a nitrogen atmosphere, 2.9 g of o-dichlorobenzene was added to a 20 ml Schlenk vessel and dissolved oxygen was removed by repeating three times a cycle composed of freezing (liquid nitrogen)-pressure reduction-replacement with nitrogen-melting. Thereto was added 2.5 mg of pentacene (manufactured by Tokyo Chemical Industry Co. Ltd.). When the whole was heated to 120° C. for dissolution, a reddish purple solution was obtained. Then, an upper stopcock of the Schlenk vessel was opened and air was introduced by bringing the vessel into contact with open air for 1 minute, followed by stirring at 120° C. Based on gas chromatography and gas chromatography-mass spectroscopy (GCMS) analyses, it was found that 6,13-pentacenequinone was formed.

Further, when the solution was brought into contact with air at 120° C. for 1 hour under stirring, the color of the solution changed into yellow. Based on gas chromatography analysis, it was found that the formation of 6,13-pentacenequinone increased.

Comparative Example 2

Evaluation of Oxidation Resistance

Oxidation resistance was evaluated using terphenylene obtained in Referential Example 1 wherein all the substituents were hydrogen.

Under a nitrogen atmosphere, 2.3 g of o-dichlorobenzene was added to a 20 ml Schlenk vessel and dissolved oxygen was removed by repeating three times a cycle composed of freezing (liquid nitrogen)-pressure reduction-replacement with nitrogen-melting. Thereto was added 4.1 mg of terphenylene obtained in Referential Example 1. When the whole was stirred at 22° C., a reddish orange solution was obtained. Then, an upper stopcock of the Schlenk vessel was opened and air was introduced by bringing the vessel into contact with open air for 1 hour. The color of the solution changed into yellowish orange and it was confirmed that a new peak was formed at a side higher than the boiling point of terphenylene based on gas chromatography analysis. Furthermore, based on gas chromatography-mass spectroscopy (GCMS) analysis, it was found that the new peak was derived from a compound having a molecular weight corresponding to the compound wherein an oxygen molecule was incorporated into terphenylene.

Example 13

Preparation of Organic Thin Film

Under a nitrogen atmosphere, 5.2 mg of 2,3,7,8-tetrafluoroterphenylene obtained in Example 11 was mixed with toluene (10 g) and the whole was stirred at 80° C. for 1 hour to prepare a red solution of 2,3,7,8-tetrafluoroterphenylene.

Under a nitrogen atmosphere, a concavely curved glass substrate is heated at 80° C. and the above solution was applied on the substrate using a dropper and dried under normal pressure to prepare a thin film having a film thickness of 320 nm. As a result of analyzing the ingredient of the thin film by gas chromatography, no peaks derived from compounds other than 2,3,7,8-tetrafluoroterphenylene were present and thus no oxidation was observed.

Synthetic Example 3

Synthesis of 1,2-dibromo-4,5-diiodobenzene 1,2-Dibromo-4,5-diiodobenzene was synthesized according to "Synlett" 2003, pp. 29-34.

To a 1 L three-necked flask fitted with a mechanical stirrer were added 36.9 g (162 mmol) of periodic acid and 150 ml of sulfuric acid. After periodic acid was dissolved, 80.7 g (486 mmol) of potassium iodide was added portionwise. The temperature of the content was cooled to 0° C. and 75.0 g (318 mmol) of 1,2-dibromobenzene was added. The resulting mixture was stirred at 0° C. for 30 minutes. After the reaction mixture was poured into ice, the whole was filtrated and a solid was taken out. The solid was recrystallized from THF/methanol twice to obtain white crystals of 1,2-dibromo-4,5-diiodobenzene (76.2 g, yield 49%).

$^1$H NMR (CDCl$_3$, 21° C.): δ=8.03 (s, 2H).

Synthetic Example 4

Synthesis of 1,2-dibromo-4,5-diphenylbenzene

To a 200 ml Schlenk reaction vessel were added under a nitrogen atmosphere 3.074 g (6.30 mmol) of 1,2-dibromo-4,5-diiodobenzene synthesized in Synthetic Example 3, 600 mg (0.519 mmol) of tetrakis(triphenylphosphine)palladium (manufactured by Tokyo Chemical Industry Co. Ltd.), and 1.920 mg (15.7 mmol) of phenylboronic acid (manufactured by Wako Pure Chemical Industries, Ltd.). Further, 50 ml of toluene, 13 ml of ethanol, and an aqueous solution composed of 4.007 g (37.8 mol) of sodium carbonate and 16 ml of water were added. The whole was heated to 82° C. and stirred for 24 hours. After cooling to room temperature, toluene and water were added and phase separation was conducted. The organic phase was concentrated and the resulting residue was dissolved in 26 ml of toluene. Then, 1.0 ml of a 70% tert-butyl hydroperoxide solution (manufactured by Wako Pure Chemical Industries, Ltd.) was added thereto, followed by 2 hours of stirring at room temperature. The toluene solution was washed twice with water and then the organic phase was concentrated under reduced pressure. The obtained residue was purified by silica gel column chromatography (solvent: hexane) to obtain a white solid of 1,2-dibromo-4,5-diphenylbenzene (1.953 g, yield 80%).

$^1$H NMR (CDCl$_3$, 21° C.): δ=7.67 (s, 2H), 7.24-7.13 (m, 6H), 7.12-6.90 (m, 4H).

MS m/z: 388 (M$^+$, 100%), 308 (M$^+$-Br, 23), 228 (M$^+$-2Br, 53).

Synthetic Example 5

Synthesis of 2-phenyl-5-bromo-4-biphenylboronic acid

To a 100 ml Schlenk reaction vessel were added under a nitrogen atmosphere 755 mg (1.95 mmol) of 1,2-dibromo-4,5-diphenylbenzene synthesized in Synthetic Example 4 and 12 ml of THF. The solution was cooled to −100° C. and 1.3 ml (2.1 mmol) of a hexane solution of n-butyllithium (manufactured by Kanto Chemical Co., Ltd., 1.59M) was added dropwise. After 30 minutes of aging, 472 mg (2.51 mmol) of triisopropyl borate (manufactured by Tokyo Chemical Industry Co., Ltd.) was added dropwise. After the temperature was gradually raised to room temperature, 3N hydrochloric acid was added and phase separation was conducted. The organic phase was concentrated under reduced pressure to obtain 770 mg of a white solid.

Example 14

Synthesis of 4,5,4",5"-tetraphenyl-2,2',5',2"-tetrabromo-1,1',4',1"-terphenyl

To a 100 ml Schlenk reaction vessel were added under a nitrogen atmosphere 770 mg of 2-phenyl-5-bromo-4-biphenylboronic acid synthesized in Synthetic Example 5, 476 mg (0.976 mmol) of 1,4-dibromo-2,5-diiodobenzene synthesized in Synthetic Example 1, 90.1 mg (0.078 mmol) of tetrakis(triphenylphosphine)palladium (manufactured by Tokyo Chemical Industry Co. Ltd.), 7.6 ml of toluene, and 1.8 ml of ethanol. Further, a solution composed of 625 mg (5.90 mmol) of sodium carbonate and 2.3 ml of water was added and the resulting mixture was subjected to a reaction at 85° C. for 30 hours. After cooling to room temperature, toluene and an aqueous sodium chloride solution were added and phase separation was conducted. The organic phase was washed with an aqueous sodium chloride solution. The organic phase was concentrated under reduced pressure and the solvent was removed by distillation. The resulting solid was recrystallized using a mixed solvent of toluene:hexane=7:3 to obtain a white solid of the objected compound (467 mg, yield 56%).

$^1$H NMR spectrum (CDCl$_3$ 21° C.): δ=7.77 (s, 0.85H), 7.76 (s, 1.15H), 7.69 (s, 2H)>7.42 (s, 1.15H), 7.35 (s, 0.85H), 7.28-7.13 (m, 20H).

The following shows the structural formula of the resulting 4,5,4",5"-tetraphenyl-2,2',5',2"-tetrabromo-1,1',4',1"-terphenyl.

[ka 42]

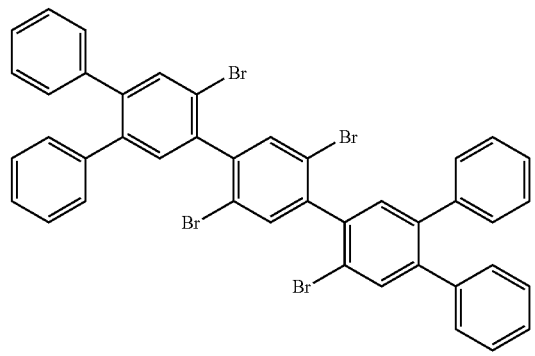

FABMS m/z: 850 (M$^+$, 100%), 770 (M$^+$-Br, 71).

Example 15

Synthesis of 4,5,4",5"-tetraphenyl-2,2',5',2"-tetrabromo-1,1',4',1"-terphenyl

To a 100 ml Schlenk reaction vessel were added under a nitrogen atmosphere 411 mg (1.06 mmol) of 1,2-dibromo-4,5-diphenylbenzene synthesized in Synthetic Example 4 and 5 ml of THF. The solution was cooled to −105° C. and 0.70 ml (1.1 mmol) of a hexane solution of n-butyllithium (manufactured by Kanto Chemical Co., Ltd., 1.59M) was added dropwise. After 5 minutes of aging, 9.8 ml (9.8 mmol) of a diethyl ether solution of zinc chloride (manufactured by Sigma Aldrich, 1.0M) was added dropwise at the temperature. After the temperature was gradually raised to room temperature, the formed white slurry liquid was concentrated under reduced pressure. To the resulting white solid were added 173 mg (0.355 mmol) of 1,4-dibromo-2,5-diiodobenzene synthesized in Synthetic Example 1, 29.0 mg (0.025 mmol) of tetrakis(triphenylphosphine)palladium (manufactured by Tokyo Chemical Industry Co. Ltd.), and 5 ml of ethylene glycol dimethyl ether. After the reaction was carried out at 80° C. for 50 hours, the vessel was cooled with water and the reaction was stopped by adding 3N hydrochloric acid (5 ml). After toluene and sodium chloride were added thereto, phase separation was conducted and the organic phase was washed with an aqueous sodium chloride solution. The organic phase was concentrated under reduced pressure and the solvent was removed by distillation. The obtained residue was dissolved in 10 ml of toluene and a 70% tert-butyl hydroperoxide solution (manufactured by Wako Pure Chemical Industries, Ltd.) (0.05 ml) was added thereto, followed by 2 hours of stirring at room temperature. The solution was washed with water and then the organic phase was concentrated under reduced pressure. The organic phase was dissolved in toluene and the solution was passed through a column packed with silica gel. The elute was concentrated under reduced pressure and the resulting solid was recrystallized using toluene to obtain a white solid of the objective compound (27 mg, yield 9%).

Example 16

Synthesis of 4,5-diphenyl-2,2',5',2"-tetrabromo-1,1', 4',1"-benzoterphenyl

To a 100 ml Schlenk reaction vessel were added under a nitrogen atmosphere 333 mg (1.00 mmol) of 2-bromo-3-iodonaphthalene synthesized in Synthetic Example 2 and 20 ml of THF. The solution was cooled to −65° C. and 1.3 ml (1.04 mmol) of a THF solution of isopropylmagnesium bromide (manufactured by Tokyo Chemical Industry Co. Ltd., 0.80M) was added dropwise. After 30 minutes of aging, 1.1 ml (1.1 mmol) of a diethyl ether solution of zinc chloride (manufactured by Sigma Aldrich, 1.0M) was added dropwise at the temperature. After the temperature was gradually raised to room temperature, the formed white slurry liquid was concentrated under reduced pressure. To the resulting white solid were added 488 mg (1.00 mmol) of 1,4-dibromo-2,5-diiodobenzene synthesized in Synthetic Example 1, 83 mg (0.072 mmol) of tetrakis(triphenylphosphine)palladium (manufactured by Tokyo Chemical Industry Co. Ltd.), and 3 ml of THF. After the reaction was carried out at 60° C. for 6 hours, the vessel was cooled with water and the reaction was stopped by adding 4 ml of 3N hydrochloric acid. After toluene and sodium chloride were added thereto, phase separation was conducted and the organic phase was washed with an aqueous sodium chloride solution. The organic phase was concentrated under reduced pressure and the solvent was removed by distillation. Further, after the residue was heated and dried under vacuum, 222 mg of 2-phenyl-5-bromo-4-biphenylboronic acid synthesized in the same manner as in Synthetic Example 5, 41 mg (0.035 mmol) of tetrakis(triphenylphosphine)palladium (manufactured by Tokyo Chemical Industry Co. Ltd.), 5.2 ml of toluene, and 1.2 ml of ethanol were added to the obtained residue. A solution composed of 349 mg (3.29 mmol) of sodium carbonate and 1.7 ml of water was further added and the mixture was subjected to a reaction at 85° C. for 6 hours. After cooling to room temperature, toluene and an aqueous sodium chloride solution were added and phase separation was conducted. The organic phase was washed with an aqueous sodium chloride solution. The organic phase was concentrated under reduced pressure and the solvent was removed by distillation, followed by further drying under vacuum. The obtained residue was dissolved in toluene and a 70% tert-butyl hydroperoxide solution (manufactured by Wako Pure Chemical Industries, Ltd.) (0.06 ml) was added thereto, followed by 2 hours of is stirring at room temperature. The solution was washed with water and then the organic phase was concentrated under reduced pressure. The residue was dissolved in hexane and chloroform and the solution was passed through a column packed with silica gel. The elute was concentrated under reduced pressure and the resulting crude solid was washed with hexane to obtain the objective compound (292 mg, yield 62.1%).

$^1$H NMR spectrum (CDCl$_3$, 21° C.): δ=8.22 (s, 0.45H), 8.20 (s, 0.55H), 7.87-7.80 (m, 2H), 7.85 (s, 1H), 7.77 (s, 1H), 7.69 (s, 0.55H), 7.68 (s, 0.45H), 7.66 (s, 1H), 7.59-7.53 (m, 2H), 7.42 (s, 0.55H), 7.38 (s, 0.45H), 7.29-7.12 (m, 10H).

MS m/z: 748 (M$^+$, 100%), 668 (M$^+$-Br, 10%), 588 (M$^+$-2Br, 24%), 508 (M$^+$-3Br, 14%), 428 (M$^+$-4Br, 29%).

The following shows the structural formula of the resulting 4,5-diphenyl-2,2',5',2"-tetrabromo-1,1',4',1"-benzoterphenyl.

[ka 43]

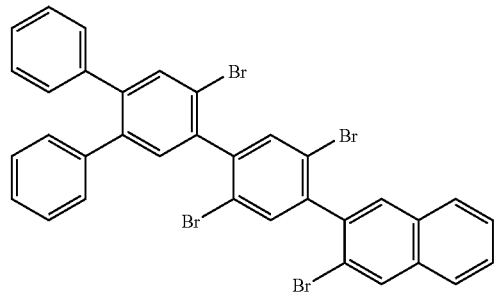

Example 17

Synthesis of 4,5-diphenyl-2,2',5',2"-tetrabromo-1,1', 4',1"-benzoterphenyl

To a 100 ml Schlenk reaction vessel were added under a nitrogen atmosphere 156 mg of 2-phenyl-5-bromo-4-biphenylboronic acid synthesized in the same manner as in Synthetic Example 5, 194 mg (0.40 mmol) of 1,4-dibromo-2,5-diiodobenzene synthesized in Synthetic Example 1, 32 mg (0.028 mmol) of tetrakis(triphenylphosphine)palladium (manufactured by Tokyo Chemical Industry Co. Ltd.), 3.1 ml of toluene, and 0.7 ml of ethanol. Further, a solution composed of 253 mg (2.39 mmol) of sodium carbonate and 0.9 ml of water was added and the resulting mixture was subjected to a reaction at 85° C. for 5 hours. After cooling to room temperature, toluene and an aqueous sodium chloride solution were added and phase separation was conducted. The organic phase was washed with an aqueous sodium chloride solution. The organic phase was concentrated under reduced pressure and the solvent was removed by distillation. Further, the phase was heated and dried under vacuum to obtain an intermediate.

On the other hand, to another 100 ml Schlenk reaction vessel were added under a nitrogen atmosphere 85 mg (0.255 mmol) of 2-bromo-3-iodonaphthalene synthesized in Synthetic Example 2 and 2.0 ml of THF. The solution was cooled to −65° C. and 0.34 ml (0.27 mmol) of a THF solution of isopropylmagnesium bromide (manufactured by Tokyo Chemical Industry Co. Ltd., 0.80M) was added dropwise. After 30 minutes of aging, 33 mg (0.32 mmol) of trimethyl borate (manufactured by Wako Pure Chemical Industries, Ltd.) was added dropwise at the temperature. After the temperature was gradually raised to room temperature, 3N hydrochloric acid was added and phase separation was conducted. The organic phase was concentrated under reduced pressure to obtain 3-bromo-2-naphthylboronic acid as a residue. To the resulting white solid were added the intermediate obtained in the above, 15 mg (0.013 mmol) of tetrakis(triphenylphosphine)palladium (manufactured by Tokyo Chemical Industry Co. Ltd.), 2.2 ml of toluene, and 0.5 ml of ethanol. A solution composed of 148 mg (1.39 mmol) of sodium carbonate and 0.7 ml of water was further added and the mixture was subjected to a reaction at 85° C. for 5 hours. After cooling to room temperature, toluene and an aqueous sodium chloride solution were added and phase separation was conducted. The organic phase was washed with aqueous sodium chloride solution. The organic phase was concentrated under reduced pressure and the solvent was removed by distillation, followed by further heating and drying under vacuum. The obtained residue was dissolved in toluene and a 70% tert-butyl hydroperoxide solution (manufactured by Wako Pure Chemical Industries, Ltd.) (0.04 ml) was added thereto, followed by 2 hours of stirring at room temperature. The solution was washed with water and then the organic phase was concentrated under reduced pressure. The residue was dissolved in hexane and chloroform and the solution was passed through a column packed with silica gel. The elute was concentrated under reduced pressure and the resulting crude solid was washed with hexane to obtain the objective compound (103 mg, yield 54.0%).

Example 18

Synthesis of 2,3-diphenylbenzoterphenylene

To a 100 ml Schlenk reaction vessel were added under a nitrogen atmosphere 103 mg (0.138 mmol) of 4,5-diphenyl-2,2',5',2''-tetrabromo-1,1',4',1''-benzoterphenyl synthesized in Example 17 and 6 ml of THF. The suspension solution was cooled to −75° C. and 0.95 ml (0.93 mmol) of a cyclohexane solution of sec-butyllithium (manufactured by Kanto Chemical Co., Ltd., 0.98M) was added dropwise. After 30 minutes of stirring, 188 mg (1.40 mmol) of copper(II) chloride (manufactured by Wako Pure Chemical Industries, Ltd.) was charged at once at −75° C. and the reaction temperature was gradually raised to 0° C. over a period of 14 hours. After 3N hydrochloric acid and toluene were added, phase separation was conducted and the organic phase was washed with a saturated aqueous sodium chloride solution. After the organic phase was concentrated under reduced pressure, hexane was added to the obtained residue and, after stirring, the whole was allowed to stand. The supernatant was removed and the residue was dried under reduced pressure. The residue was recrystallized from toluene to obtain orange crystals of 2,3-diphenylbenzoterphenylene (23 mg, yield 38.9%).

$^1$H NMR (deuterated benzene, 21° C.): δ=7.25-6.95 (m, 14H), 6.51 (s, 2H), 6.50 (s, 2H), 6.21 (s, 2H).

MS m/z: 428 (M$^+$, 100%), 213 ((M$^+$/2)-1, 34%).

The following shows the structure of the resulting objective compound.

[ka 44]

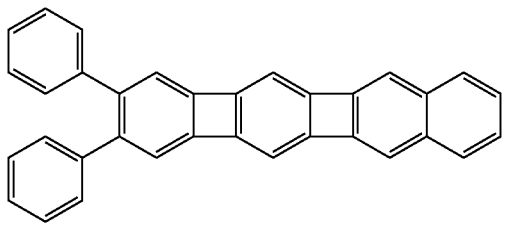

While the invention has been described in detail and with reference to specific embodiments thereof, it will be apparent to one skilled in the art that various changes and modifications can be made therein without departing from the spirit and scope thereof.

The present application is based on Japanese Patent Application No. 2005-112774 filed on Apr. 8, 2005, Japanese Patent Application No. 2005-112775 filed on Apr. 1, 2005, Japanese Patent Application No. 2005-112776 filed on Apr. 8, 2005, Japanese Patent Application No. 2005-366667 filed on Dec. 20, 2005, and Japanese Patent Application No. 2005-366668 filed on Dec. 20, 2005 and the contents are incorporated herein by reference.

INDUSTRIAL APPLICABILITY

There are provided a terphenylene derivative having an excellent oxidation resistance and capable of forming a semiconductor active phase by a coating process and a use thereof. Furthermore, according to the production process of the invention, a terphenylene derivative to which fluorine atom(s) are introduced can be produced and thus an organic semiconductor material can be provided. Accordingly, industrial value of the invention is remarkable.

The invention claimed is:

1. A terphenylene derivative represented by the following formula (1):

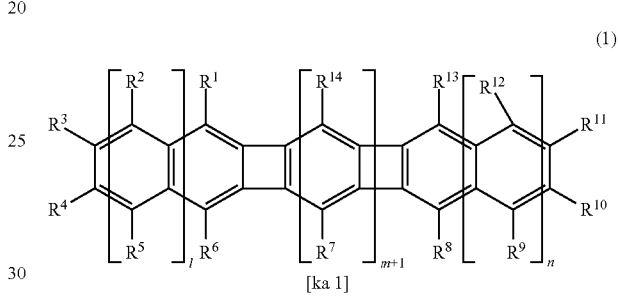

[ka 1]

wherein the substituents $R^1$ to $R^{14}$ are the same or different and each represents a hydrogen atom, a fluorine atom, a chlorine atom, an aryl group having 4 to 30 carbon atoms, an alkenyl group having 2 to 30 carbon atoms, an alkyl group having 1 to 20 carbon atoms or a halogenated alkyl group having 1 to 20 carbon atoms, or a diarylamino group having 8 to 30 carbon atoms; the substituents $R^3$ and $R^4$ are combined to form an unsaturated ring and the substituents $R^{10}$ and $R^{11}$ are combined to form an unsaturated ring, or only the substituents $R^3$ and $R^4$ are combined to form an unsaturated ring, or only the substituents $R^{10}$ and $R^{11}$ are combined to form an unsaturated ring; and l, m, and n each represents an integer of 0 or 1; when l=0, m=0, and n=0, when l=1, m=0, and n=0, or when l=0, m=1, and n=0, at least one of the substituents $R^1$ to $R^{14}$ is not a hydrogen atom.

2. The terphenylene derivative according to claim 1, wherein the substituents $R^1$ to $R^{14}$ are the same or different and each represents at least one substituent selected from the group consisting of a hydrogen atom, a fluorine atom, an aryl group having 4 to 30 carbon atoms, and an alkyl group having 1 to 20 carbon atoms and at least one of the substituents $R^1$ to $R^{14}$ is not a hydrogen atom.

3. The terphenylene derivative according to claim 1, wherein the substituents $R^3$, $R^4$, $R^{10}$, and $R^{11}$ are the same or different and each represents at least one substituent selected from the group consisting of an aryl group having 4 to 30 carbon atoms, an alkenyl group having 2 to 30 carbon atoms, an alkyl group having 1 to 20 carbon atoms or a halogenated alkyl group having 1 to 20 carbon atoms, and a diarylamino group having 8 to 30 carbon atoms and the substituents $R^1$, $R^2$, $R^5$ to $R^9$, and $R^{12}$ to $R^{14}$ are the same or different and each represents at least one substituent selected from the group consisting of a hydrogen atom, a fluorine atom, and a chlorine atom.

4. The terphenylene derivative according to claim 1, wherein m is 0.

5. The terphenylene derivative according to claim 1, wherein m and l are both 0.

6. The terphenylene derivative according to claim 1, wherein m, l, and n are all 0.

7. A process for producing the terphenylene derivative according to any one of claims 1 to 6, which comprises tetralithiating a tetrahaloterphenyl derivative represented by the following formula (2) with a lithiating agent and subsequently treating the resulting compound with a copper compound:

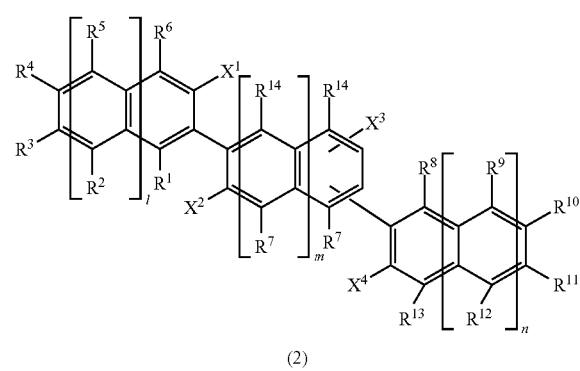

(2)

wherein the substituents $X^1$ to $X^4$ represent a bromine atom, an iodine atom, or a chlorine atom; the substituents $R^1$ to $R^{14}$ are the same or different and each represents a hydrogen atom, a fluorine atom, a chlorine atom, an aryl group having 4 to 30 carbon atoms, an alkenyl group having 2 to 30 carbon atoms, an alkyl group having 1 to 20 carbon atoms or a halogenated alkyl group having 1 to 20 carbon atoms, or a diarylamino group having 8 to 30 carbon atoms; the substituents $R^3$ and $R^4$ are combined to form an unsaturated ring and the substituents $R^{10}$ and $R^{11}$ are combined to form an unsaturated ring, or only the substituents $R^3$ and $R^4$ are combined to form an unsaturated ring, or only the substituents $R^{10}$ and $R^{11}$ are combined to form an unsaturated ring; and l, m, and n each represents an integer of 0 or 1, provided that the designation of the formula (2) is the general term for the para- and meta-position isomers represented by the following formulae (3) and (4):

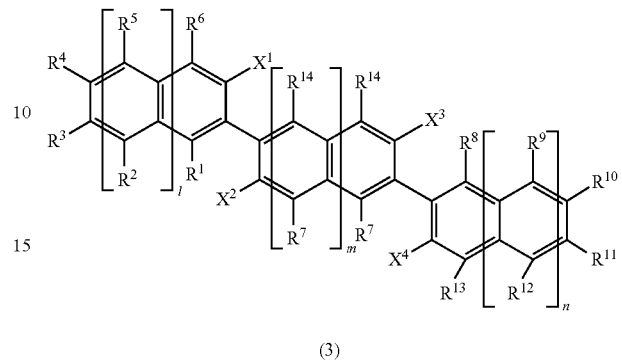

(3)

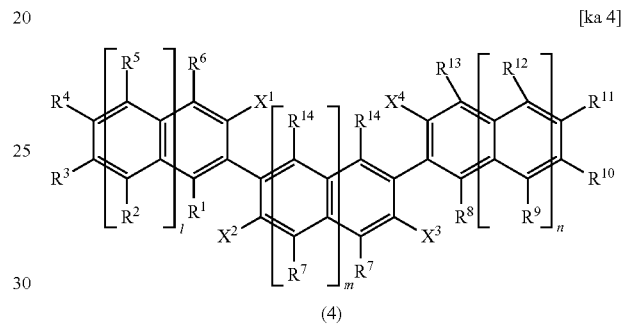

(4)

wherein the substituents $R^1$ to $R^{14}$ and $X^1$ to $X^4$ and the symbols l, m, and n in the formula (3) and the formula (4) represent the same meanings as the substituents and the symbols represented in the formula (2).

8. The process for producing the terphenylene derivative according to claim 7, wherein the lithiating agent is an alkyllithium.

9. The process for producing the terphenylene derivative according to claim 7, wherein the lithiating agent is used in an amount of 3 to 20 equivalents to the tetrahaloterphenyl derivative represented by the formula (2).

* * * * *